US008444983B2

(12) United States Patent
Feinstein

(10) Patent No.: US 8,444,983 B2
(45) Date of Patent: May 21, 2013

(54) COMPOSITION OF ANTI-ENDO180 ANTIBODIES AND METHODS OF USE FOR THE TREATMENT OF CANCER AND FIBROTIC DISEASES

(75) Inventor: Elena Feinstein, Rehovot (IL)

(73) Assignee: Quark Pharmaceuticals, Inc., Fremont, CA (US)

( * ) Notice: Subject to any disclaimer, the term of this patent is extended or adjusted under 35 U.S.C. 154(b) by 16 days.

(21) Appl. No.: 13/255,214

(22) PCT Filed: Mar. 23, 2010

(86) PCT No.: PCT/US2010/028200

§ 371 (c)(1),
(2), (4) Date: Sep. 7, 2011

(87) PCT Pub. No.: WO2010/111198

PCT Pub. Date: Sep. 30, 2010

(65) Prior Publication Data

US 2012/0114704 A1 May 10, 2012

Related U.S. Application Data

(60) Provisional application No. 61/162,348, filed on Mar. 23, 2009.

(51) Int. Cl.
*A61K 51/10* (2006.01)
*A61K 49/16* (2006.01)
*A61K 39/395* (2006.01)
*A61K 39/44* (2006.01)

(52) U.S. Cl.
USPC .................. 424/143.1; 424/133.1; 424/152.1

(58) Field of Classification Search
None
See application file for complete search history.

(56) References Cited

U.S. PATENT DOCUMENTS 4,816,567 A 3/1989 Cabilly et al.
5,225,539 A 7/1993 Winter
5,574,142 A 11/1996 Meyer et al.
5,580,859 A 12/1996 Felgner et al.
5,585,089 A 12/1996 Queen et al.
5,693,761 A 12/1997 Queen et al.
5,898,031 A 4/1999 Crooke
6,077,508 A 6/2000 Rabanni et al.
6,107,094 A 8/2000 Crooke
6,117,977 A 9/2000 Lasky et al.
6,153,737 A 11/2000 Manoharan et al.
6,180,370 B1 1/2001 Queen et al.
6,235,886 B1 5/2001 Manoharan et al.
6,331,415 B1 12/2001 Cabilly et al.
6,395,713 B1 5/2002 Beigelman et al.
6,548,640 B1 4/2003 Winter
6,602,858 B2 8/2003 Beigelman
6,838,254 B1 1/2005 Hamers et al.
6,982,321 B2 1/2006 Winter
7,022,500 B1 4/2006 Queen et al.
7,399,468 B2 7/2008 Luther et al.
7,452,987 B2 11/2008 Giese et al.
2003/0027783 A1 2/2003 Zernicka-Goetz et al.
2003/0108923 A1 6/2003 Tuschl et al.
2004/0038921 A1 2/2004 Kreutzer et al.
2004/0203145 A1 10/2004 Zamore et al.
2004/0241248 A1 12/2004 Margalit et al.
2004/0259247 A1 12/2004 Tuschl et al.
2004/0265839 A1 12/2004 Mello et al.
2005/0042647 A1 2/2005 Baker et al.
2005/0119202 A1 6/2005 Kreutzer et al.
2005/0255487 A1 11/2005 Khvorova et al.
2007/0031844 A1 2/2007 Khvorova et al.
2007/0042982 A1 2/2007 Bentwich
2007/0072244 A1* 3/2007 Mor et al. ...................... 435/7.2
2008/0248092 A1 10/2008 Margalit et al.
2008/0311040 A1* 12/2008 Berry et al. .................... 424/9.1
2009/0022656 A1 1/2009 Margalit et al.
2009/0192104 A1 7/2009 McSwiggen et al.
2009/0202566 A1 8/2009 Mor et al.
2011/0008422 A1* 1/2011 Dekel et al. .................. 424/450
2011/0112168 A1 5/2011 Feinstein et al.

FOREIGN PATENT DOCUMENTS

WO WO 97/40154 10/1997
WO WO 00/58473 A2 10/2000
WO WO 00/58473 A3 10/2000
WO WO 2004/045543 A2 6/2004
WO WO 2004/045543 A3 6/2004
WO WO 2004/100759 A2 11/2004

(Continued)

OTHER PUBLICATIONS

ElBayoumi et Al., Tumor-Targeted Nanomedicines:Enhanced Anti-tumor Efficacy in vivo of Dosorubicin-Loaded, Long-Circulating Liposomes Modified with Cancer-Specific Monoclonal Antibody, Mar. 10, 2009, Clinical Cancer Research, vol. 15, p. 1973-1980.*
Greenspan et Al., Defining epitopes: It's not as easy as it seems, 1999, Nature Biotechnology, vol. 7, p. 936-937.*
Aboul-Fadl (2005). Antisense Oligonucleotides: The State of the Art. *Curr Med Chem*, 12(19), 2193-214.
Amarzguioui et al. (2003). Tolerance for Mutations and Chemical Modifications in a siRNA. *Nucleic Acids Research*, 31(2), 589-595.
Arruebo et al. (2009). Antibody-Conjugated Nanoparticles for Bio-medical Applications. *J Nanomaterials*, Article ID 439389.
Barik (2005). Silence of the Transcripts: RNA Interference in Medicine. *J Mol Med*, 83, 764-773.
Bass (2000). Double-Stranded RNA as a Template for Gene Silencing. *Cell*, 101, 235-238.

(Continued)

*Primary Examiner* — Misook Yu
*Assistant Examiner* — Michael D Allen
(74) *Attorney, Agent, or Firm* — John P. White; Cooper & Dunham LLP

(57) ABSTRACT

The present invention provides antibodies or antigen-binding fragments thereof that specifically bind the ENDO180 polypeptide and are internalized thereby, to conjugates comprising the molecules, to compositions comprising the antibodies and conjugates and to methods of using the same for delivery of therapeutic agents to cells that express the ENDO180 polypeptide on the surface of the cell for treating cell proliferative diseases or disorders and fibrosis, and for controlling (modulating) tumor progression.

15 Claims, 9 Drawing Sheets

FOREIGN PATENT DOCUMENTS

| | | | |
|---|---|---|---|
| WO | WO 2004/100759 | A3 | 11/2004 |
| WO | WO 2006/023491 | A2 | 3/2006 |
| WO | WO 2006/023491 | A3 | 3/2006 |
| WO | WO 2008/020435 | A2 | 2/2008 |
| WO | WO 2008/020435 | A3 | 2/2008 |
| WO | WO 2008/050329 | A2 | 5/2008 |
| WO | WO 2008/050329 | A3 | 5/2008 |
| WO | WO 2008/104978 | A2 | 9/2008 |
| WO | WO 2008/104978 | A3 | 9/2008 |
| WO | WO 2009/044392 | A2 | 4/2009 |
| WO | WO 2009/044392 | A3 | 4/2009 |
| WO | WO 2011/066475 | | 6/2011 |

OTHER PUBLICATIONS

Behrendt (2004). The Urokinase Receptor (uPAR) and the uPAR-Associated Protein (uPARAP/Endo180): Membrane Proteins Engaged in Matrix Turnover During Tissue Remodeling. *Biol Chem*, 385(2), 103-136.

Behrendt et al. (2000). A Urokinase Receptor-Associated Protein with Specific Collagen Binding Properties. *J Blot Chem*, 275(3), 1993-2002.

Bernstein et al. (2001). The Rest is Silence. *RNA*, 7(11), 1509-1521.

Bird et al. (1988). Single-Chain Antigen-Binding Proteins. *Science*, 242, 423-426.

Braasch et al. (2003). RNA Interference in Mammalian Cells by Chemically-Modified RNA. *Biochemistry*, 42(26), 7967-7975.

Caplen et al. (2001). Specific Inhibition of Gene Expression by Small Double-Stranded RNAs in Invertebrate and Vertebrate Systems. *PNAS*, 98(17), 9742-9747.

Chakraborty (2007). Potentiality of Small Interfering RNAs (siRNA) as Recent Therapeutic Targets for Gene-Silencing. *Current Drug Targets*, 8(3), 469-482.

Chalk et al. (2004). Improved and Automated Prediction of Effective siRNA. *BBRC*, 319(1), 264-274.

Chiu et al. (2003). siRNA Function in RNAi: a Chemical Modification Analysis. *RNA*, 9(9), 1034-1048.

Czauderna et al. (2003). Structural Variations and Stabilising Modifications of Synthetic siRNAs in Mammalian Cells. *Nucleic Acids Res*, 31(11), 2705-2716.

Elbashir et al. (2001). Duplexes of 21-Nucleotide RNAs Mediate RNA Interference in Cultured Mammalian Cells. *Nature*, 411, 494-498.

Elbashir et al. (2001). Functional Anatomy of siRNAs for Mediating Efficient RNAi in *Drosophila melanogaster* Embryo Lysate. *EMBO J*, 20(23), 6877-6888.

Elbashir et al. (2001). RNA Interference is Mediated by 21- and 22-Nucleotide RNAs. *Genes & Dev*, 15, 188-200.

Fire et al. (1998). Potent and Specific Genetic Interference by Double-Stranded RNA in *Caenorhabditis elegans*. *Nature*, 391, 806-811.

Hammond et al. (2000). An RNA-Directed Nuclease Mediates Post-Transcriptional Gene Silencing in *Drosophila* Cells. *Nature*, 404, 293-296.

Howard et al. (2002). The C-type Lectin Receptor Endo180 Displays Internalization and Recycling Properties Distinct from Other Members of the Mannose Receptor Family. *J Biol Chem*, 277(35), 32320-32331.

Kjøller (Feb. 1, 2004). uPARAP/endo180 Directs Lysosomal Delivery and Degradation of Collagen IV. *Exp Cell Res*, 293(1), 106-116.

Levenkova et al. (2004). Gene Specific siRNA Selector. *Bioinformatics*, 20(3), 430-432.

Liu (2007). Exploring Cell Type-Specific Internalizing Antibodies for Targeted Delivery of siRNA. *Briefings in Functional Genomics and Proteomics*, 6(2), 112-119.

Madsen et al. (2005). Blocking Cellular Collagen Degradation with Monoclonal Antibodies Against uPARAP/Endo180. *Thromb Haemostasis. 10th International Workshop on Molecular and Cellular Biology of Plasminogen Activation*, 93(4), A22.

McManus et al. (2002). Gene Silencing Using Micro-RNA Designed Hairpins. *RNA*, 8, 842-850.

McManus and Sharp (2002). Gene Silencing in Mammals by Small Interfering RNAs. *Nature Rev Genet*, 3, 737-747.

Noonberg et al. (1994). In Vivo Generation of Highly Abundant Sequence-Specific Oligonucleotides for Antisense and Triplex Gene Regulation. *Nucleic Acid Res*, 22(14), 2830-2836.

Paddison et al. (2003). siRNAs and siRNAs: Skeleton Keys to the Human Genome. *Curr Opin Mol Ther*, 5(3), 217-224.

Prakash et al. (2005). Positional Effect of Chemical Modifications on Short Interference RNA Activity in Mammalian Cells. *J Med Chem*, 48, 4247-4253.

Seela et al. (1987). Oligodeoxyribonucleotides Containing 1,3-propanediol as Nucleoside Substitute. *Nucleic Acids Res*, 15(7), 3113-3129.

Sharp (1999). RNAi and Double-Strand RNA. *Genes & Dev*, 13, 139-141.

Sheikh et al. (2000). Endo180, an Endocytic Cecycling Glycoprotein Related to the Macrophage Mannose Receptor is Expressed on Fibroblasts, Endothelial Cells and Macrophages and Functions as a Lectin Receptor. *Journal of Cell Science*, 113, 1021-1032.

Sioud (2005). Antibodies Guide the Way. *Gene Therapy*, 1-2.

Song et al. (2005). Antibody Mediated in Vivo Delivery of Small Interfering RNAs via Cell-Surface Receptors. *Nature Biotechnology*, 23(6), 709-717.

Sulek et al. (2007). Increased Expression of the Collagen Internalization Receptor UPARAP/Endo180 in the Stroma of Head and Neck Cancer. *J Histo Cyto*, 55(4), 347-353.

Ui-Tei et al. (2004). Guidelines for the Selection of Highly Effective siRNA Sequences for Mammalian and Chick RNA Interference. *Nucleic Acids Research*, 32(3), 936-948.

Ui-Tei et al. (2006). Essential Notes Regarding the Design of Functional siRNAs for Efficient Mammalian RNAi. *J Biomed Biotechnol*, Article ID 65052.

Wienke et al. (2007). The Collagen Receptor Endo180 (CD280) is Expressed on Basal-like Breast Tumor Cells and Promotes Tumor Growth in Vivo. *Cancer Res*, 67(21), 10230-10240.

Zamore et al. (2000). RNAi: Double-Stranded RNA Directs the ATP-Dependent Cleavage of mRNA at 21 to 23 Nucleotide Intervals. *Cell*, 101, 25-33.

Zvaritch et al. (1996). Endocytic Properties of the M-type 180-kDa Receptor for Secretory Phospholipases $A_2$. *J Biol Chem*, 271(1), 250-257.

Notification of Transmittal of the International Search Report and the Written Opinion of the International Searching Authority, or the Declaration, including an International Search Report and Written Opinion of the International Searching Authority, mailed Feb. 26, 2008 in connection with PCT International Application No. PCT/IL04/00423, filed May 18, 2004.

International Search Report, mailed Jul. 22, 2010 in connection with PCT International Application No. PCT/US2010/028200, filed Mar. 23, 2010.

International Preliminary Report on Patentability, including Written Opinion of the International Searching Authority (ISA/EP), issued Sep. 27, 2011 in connection with PCT International Application No. PCT/US2010/028200, filed Mar. 23, 2010.

* cited by examiner

FIGURE 1A

```
   1 CGGAGGAGGA CGCGAGCCCC UUGCGGGCGG UCAUCACAGC CCAGCCUCGG GGCUGCCACA
  61 GCGCGUUGCG CCUGUGCGCC CUCGGUCCCC GCGUCCACUG AGCGCCGCGC UCGGGGAUGG
 121 GGCCCGGCCG GCCGGCCCCC GCGCCCUGGC CUCGUCACCU GCUGCGCUGC GUCCUGCUCC
 181 UCGGGUGCCU GCACCUCGGC CGUCCCGGCG CCCCUGGGGA CGCCGCCCUC CCGGAACCCA
 241 ACGUCUUCCU CAUCUUCAGC CAUGGACUGC AGGGCUGCCU GGAGGCCCAG GGCGGGCAGG
 301 UCAGAGUCAC CCCGGCUUGC AAUACCAGCC UCCCUGCCCA GCGCUGGAAG UGGGUCUCCC
 361 GAAACCGGCU AUUCAACCUG GGUACCAUGC AGUGCCUGGG CACAGGCUGG CCAGGCACCA
 421 ACACCACGGC CUCCCUGGGC AUGUAUGAGU GUGACCGGGA AGCACUGAAU CUUCGCUGGC
 481 AUUGUCGUAC ACUGGGUGAC CAGCUGUCCU UGCUCCUGGG GGCCCGCACC AGCAACAUAU
 541 CCAAGCCUGG CACCCUUGAG CGUGGUGACC AGACCCGCAG UGGCCAGUGG CGCAUCUACG
 601 GCAGCGAGGA GGACCUAUGU GCUCUGCCCU ACCACGAGGU CUACACCAUC CAGGGAAACU
 661 CCCACGGAAA GCCGUGCACC AUCCCCUUCA AAUAUGACAA CCAGUGGUUC CACGGCUGCA
 721 CCAGCACGGG CCGCGAGGAU GGUCACCUGU GGUGUGCCAC CACCCAGGAC UACGGCAAAG
 781 ACGAGCGCUG GGGCUUCUGC CCCAUCAAGA GUAACGACUG CGAGACCUUC UGGGACAAGG
 841 ACCAGCUGAC UGACAGCUGC UACCAGUUUA ACUUCCAGUC CACGCUGUCG UGGAGGGAGG
 901 CCUGGGCCAG CUGCGAGCAG CAGGGUGCGG AUCUGCUGAG CAUCACGGAG AUCCACGAGC
 961 AGACCUACAU CAACGGCCUC CUCACUGGGU ACAGCUCCAC CCUGUGGAUC GGCUUGAAUG
1021 ACUUGGACAC GAGCGGAGGC UGGCAGUGGU CGGACAACUC GCCCCUCAAG UACCUCAACU
1081 GGGAGAGUGA CCAGCCGGAC AACCCCAGUG AGGAGAACUG UGGAGUGAUC CGCACUGAGU
1141 CCUCGGGCGG CUGGCAGAAC CGUGACUGCA GCAUCGCGCU GCCCUAUGUG UGCAAGAAGA
1201 AGCCCAACGC CACGGCCGAG CCCACCCCUC CAGACAGGUG GGCCAAUGUG AAGGUGGAGU
1261 GCGAGCCGAG CUGGCAGCCC UUCCAGGGCC ACUGCUACCG CCUGCAGGCC GAGAAGCGCA
1321 GCUGGCAGGA GUCCAAGAAG GCAUGUCUAC GGGGCGGUGG CGACCUGGUC AGCAUCCACA
1381 GCAUGGCGGA GCUGGAAUUC AUCACCAAGC AGAUCAAGCA AGAGGUGGAG GAGCUGUGGA
1441 UCGGCCUCAA CGAUUUGAAA CUGCAGAUGA AUUUUGAGUG GUCUGACGGG AGCCUUGUGA
1501 GCUUCACCCA CUGGCACCCC UUUGAGCCCA ACAACUUCCG GGACAGUCUG GAGGACUGUG
1561 UCACCAUCUG GGGCCCGGAA GGCCGCUGGA ACGACAGUCC CUGUAACCAG UCCUUGCCAU
1621 CCAUCUGCAA GAAGGCAGGC CAGCUGAGCC AGGGGGCCGC CGAGGAGGAC CAUGGCUGCC
1681 GGAAGGGUUG GACGUGGCAC AGCCCAUCCU GCUACUGGCU GGGAGAAGAC CAAGUGACCU
1741 ACAGUGAGGC CCGGCGCCUG UGCACUGACC AUGGCUCUCA GCUGGUCACC AUCACCAACA
1801 GGUUCGAGCA GGCCUUCGUC AGCAGCCUCA UCUACAACUG GGAGGGCGAG UACUUCUGGA
1861 CGGCCCUGCA GGACCUCAAC AGCACCGGCU CCUUCUUCUG GCUCAGUGGG GAUGAAGUCA
1921 UGUACACCCA CUGGAACCGG GACCAGCCCG GGUACAGCCG UGGGGGCUGC GUGGCGCUGG
1981 CCACUGGCAG CGCCAUGGGG CUGUGGGAGG UGAAGAACUG UACCUCGUUC CGGGCCCGCU
2041 ACAUCUGCCG GCAGAGCCUG GGCACUCCAG UGACGCCGGA GCUGCCGGGG CCAGAUCCCA
2101 CGCCCAGCCU CACUGGCUCC UGUCCCCAGG GCUGGGCCUC GGACACCAAA CUCCGGUAUU
2161 GCUAUAAGGU GUUCAGCUCA GAGCGGCUGC AGGACAAGAA GAGCUGGGUC CAGGCCCAGG
2221 GGGCCUGCCA GGAGCUGGGG GCCCAGCUGC UGAGCCUGGC CAGCUACGAG GAGGAGCACU
```

FIGURE 1A cont.

2281 UUGUGGCCAA CAUGCUCAAC AAGAUCUUCG GUGAAUCAGA ACCCGAGAUC CACGAGCAGC

2341 ACUGGUUCUG GAUCGGCCUG AACCGUCGGG AUCCCAGAGG GGGUCAGAGU UGGCGCUGGA

2401 GCGACGGCGU AGGGUUCUCU UACCACAAUU UCGACCGGAG CCGGCACGAC GACGACGACA

2461 UCCGAGGCUG UGCGGUGCUG GACCUGGCCU CCCUGCAGUG GGUGGCCAUG CAGUGCGACA

2521 CACAGCUGGA CUGGAUCUGC AAGAUCCCCA GAGGUACGGA CGUGCGGGAG CCCGACGACA

2581 GCCCUCAAGG CCGACGGGAA UGGCUGCGCU UCCAGGAGGC CGAGUACAAG UUCUUUGAGC

2641 ACCACUCCAC GUGGGCGCAG GCGCAGCGCA UCUGCACGUG GUUCCAGGCC GAGCUGACCU

2701 CCGUGCACAG CCAGGCAGAG CUAGACUUCC UGAGCCACAA CUUGCAGAAG UUCUCCCGGG

2761 CCCAGGAGCA GCACUGGUGG AUCGGCCUGC ACACCUCUGA GAGCGAUGGG CGCUUCAGAU

2821 GGACAGAUGG UUCCAUUAUA AACUUCAUCU CCUGGGCACC AGGCAAACCU CGGCCUGUCG

2881 GCAAGGACAA GAAGUGCGUG UACAUGACAG CCAGCCGAGA GGACUGGGGG GACCAGAGGU

2941 GCCUGACAGC CUUGCCCUAC AUCUGCAAGC GCAGCAACGU CACCAAAGAA ACGCAGCCCC

3001 CAGACCUGCC AACUACAGCC CUGGGGGGCU GCCCCUCUGA CUGGAUCCAG UUCCUCAACA

3061 AGUGUUUUCA GGUCCAGGGC CAGGAACCCC AGAGCCGGGU GAAGUGGUCA GAGGCACAGU

3121 UCUCCUGUGA ACAGCAAGAG GCCCAGCUGG UCACCAUCAC AAACCCCUUA GAGCAAGCAU

3181 UCAUCACAGC CAGCCUCCCC AAUGUGACCU UUCACCUUUG GAUUGCCCUC CAUGCCUCGC

3241 AGAGGGACUU CCAGUGGGUG GAGCAGGAGC CUUUGAUGUA UGCCAACUGG GCACCUGGGG

3301 AGCCCUCUGG CCCUAGCCCU GCUCCCAGUG GCAACAAACC GACCAGCUGU GCGGUGGUCC

3361 UGCACAGCCC CUCAGCCCAC UUCACUGGCC GCUGGGACGA UCGGAGCUGC ACGGAGGAGA

3421 CCCAUGGCUU CAUCUGCCAG AAGGGCACGG ACCCCUCCCU GAGCCCGUCC CCAGCAGCGC

3481 UGCCCCCCGC CCCGGGCACU GAGCUCUCCU ACCUCAACGG CACCUUCCGG CUGCUUCAGA

3541 AGCCGCUGCG CUGGCACGAU GCCCUCCUGC UGUGUGAGAG CCACAAUGCC AGCCUGGCCU

3601 ACGUGCCCGA CCCCUACACC CAGGCCUUCC UCACGCAGGC UGCCCGAGGG CUGCGCACGC

3661 CGCUCUGGAU UGGGCUGGCU GGCGAGGAGG GCUCUCGGCG GUACUCCUGG GUCUCAGAGG

3721 AGCCGCUGAA CUACGUGGGC UGGCAGGACG GGGAGCCGCA GCAGCCGGGG GGCUGUACCU

3781 ACGUAGAUGU GGACGGGGCC UGGCGCACCA CCAGCUGUGA CACCAAGCUG CAGGGGGCUG

3841 UGUGUGGGGU UAGCAGUGGG CCCCCUCCUC CCCGAAGAAU AAGCUACCAU GGCAGCUGUC

3901 CCCAGGGACU GGCAGACUCC GCGUGGAUUC CCUUCCGGGA GCACUGCUAU UCUUUCCACA

3961 UGGAGCUGCU GCUGGGCCAC AAGGAGGCGC GACAGCGCUG CCAGAGAGCG GGUGGGGCCG

4021 UCCUGUCUAU CCUGGAUGAG AUGGAGAAUG UGUUUGUCUG GGAGCACCUG CAGAGCUAUG

4081 AGGGCCAGAG UCGGGGCGCC UGGCUGGGCA UGAACUUCAA CCCCAAAGGA GGCACUCUGG

4141 UCUGGCAGGA CAACACAGCU GUGAACUACU CCAACUGGGG GCCCCCGGGC UUGGGCCCCA

4201 GCAUGCUGAG CCACAACAGC UGCUACUGGA UUCAGAGCAA CAGCGGGCUA UGGCGCCCCG

4261 GCGCUUGCAC CAACAUCACC AUGGGUGUCG UCUGCAAGCU UCCUCGUGCU GAGCAGAGCA

4321 GCUUCUCCCC AUCAGCGCUU CCAGAGAACC CAGCGGCCCU GGUGGUGGUG CUGAUGGCGG

4381 UGCUGCUGCU CCUGGCCUUG CUGACCGCAG CCCUCAUCCU UUACCGGAGG CGCCAGAGCA

4441 UCGAGCGCGG GGCCUUUGAG GGUGCCCGCU ACAGCCGCAG CAGCUCCAGC CCCACCGAGG

4501 CCACUGAGAA GAACAUCCUG GUGUCAGACA UGGAAAUGAA UGAGCAACAA GAAUAGAGCC

FIGURE 1A cont.

```
4561 AGGCGCGUGG GCAGGGCCAG GGCGGGAGGA GCUGGGGAGC UGGGGCCCUG GGUCAGUCUG
4621 GCCCCCCACC AGCUGCCUGU CCAGUUGGCC UAUGGAAGGG UGCCCUUGGG AGUCGCUGUU
4681 GGGAGCCGGA GCUGGGCAGA GCCUGGGCUG GUGGGGUGCC ACCCUCCCAC AAGGGCUGGG
4741 CUGAGACCCA GCUGAGUGCA GCGUGGCGUU UCCCUUUCUG GGGGGGCCUG AGGUCUUGUC
4801 ACCUGGUCCU GUGCCCCCAC AGGAACCAGA GGUAGGAUGG GAGGGGGAAC GAGAGCCUCU
4861 UUCUCCCCAG AGCCCCCGGC CCAGGCCUGU UGAUCCGCGC CCCAGGACCC CCUUCUUUGC
4921 AGAGCCCGAG GAGCCUCCCC UGUCCCCUCG GGCAGAUCUG UUGUGUCUCU CUUCCCACCU
4981 GGCAGCCUCA GCUCUGUGCC CCUCACCCUG CUCCCUCUCG CCCCUUCUCU CCCACCCCUU
5041 CCUUCUGAGC CGGGCCCUGG GGAUUGGGGA GCCCUCUUGU UCCUGAUGAG GGUCAGCUGA
5101 GGGGGCUGAG CAUCCAUCAC UCCUGUGCCU GCUGGGGUGG CUGUGGGGCG UGGCAGGAGG
5161 GGCCUAGGUG GGUUGGGCCU GAGAACCAGG GCACGGGUGU GGUGUCUGCU GGGCUGGAGA
5221 UAAGACUGGG GAGAGACACC CCAACCUCCC AGGGUGGGAG CUGGGCCGGG CUGGGAUGUC
5281 AUCUCCUGCC GGGCGGGGGA GGGCUCUGCC CCUGGAAGAG UCCCCUGUGG GGACCAAAAU
5341 AAGUUCCCUA ACAUCUCCAG CUCCUGGCUC UGGUUUGGAG CAAGGGGAAG GGUUGCCAGA
5401 GUCCUGGGGG CCCCAGAGGA GCAGGAGUCU GGGAGGGCCC AGAGUUCACC CUCUAGUGGA
5461 UCCAGGAGGA GCAGCACCCG AGCCCUGGAG UGGCCCAGUA CCCUUCCAAG AGGCCACAGU
5521 CCCAGCCAGG ACAAAGUAUG CGGCCCAUCC UGGUGCGACA GCGUGGGACA AUGUGAACAU
5581 GGACUCGAAG ACAUGGCCCU UUCUCUGUAG UUGAUUUUUU AAAUGUGCCA UUAUUGUUUU
5641 U
```

FIGURE 1B

```
  1 MGPGRPAPAP WPRHLLRCVL LLGCLHLGRP GAPGDAALPE PNVFLIFSHG LQGCLEAQGG
 61 QVRVTPACNT SLPAQRWKWV SRNRLFNLGT MQCLGTGWPG TNTTASLGMY ECDREALNLR
121 WHCRTLGDQL SLLLGARTSN ISKPGTLERG DQTRSGQWRI YGSEEDLCAL PYHEVYTIQG
181 NSHGKPCTIP FKYDNQWFHG CTSTGREDGH LWCATTQDYG KDERWGFCPI KSNDCETFWD
241 KDQLTDSCYQ FNFQSTLSWR EAWASCEQQG ADLLSITEIH EQTYINGLLT GYSSTLWIGL
301 NDLDTSGGWQ WSDNSPLKYL NWESDQPDNP SEENCGVIRT ESSGGWQNRD CSIALPYVCK
361 KKPNATAEPT PPDRWANVKV ECEPSWQPFQ GHCYRLQAEK RSWQESKKAC LRGGGDLVSI
421 HSMAELEFIT KQIKQEVEEL WIGLNDLKLQ MNFEWSDGSL VSFTHWHPFE PNNFRDSLED
481 CVTIWGPEGR WNDSPCNQSL PSICKKAGQL SQGAAEEDHG CRKGWTWHSP SCYWLGEDQV
541 TYSEARRLCT DHGSQLVTIT NRFEQAFVSS LIYNWEGEYF WTALQDLNST GSFFWLSGDE
601 VMYTHWNRDQ PGYSRGGCVA LATGSAMGLW EVKNCTSFRA RYICRQSLGT PVTPELPGPD
661 PTPSLTGSCP QGWASDTKLR YCYKVFSSER LQDKKSWVQA QGACQELGAQ LLSLASYEEE
721 HFVANMLNKI FGESEPEIHE QHWFWIGLNR RDPRGGQSWR WSDGVGFSYH NFDRSRHDDD
781 DIRGCAVLDL ASLQWVAMQC DTQLDWICKI PRGTDVREPD DSPQGRREWL RFQEAEYKFF
841 EHHSTWAQAQ RICTWFQAEL TSVHSQAELD FLSHNLQKFS RAQEQHWWIG LHTSESDGRF
901 RWTDGSIINF ISWAPGKPRP VGKDKKCVYM TASREDWGDQ RCLTALPYIC KRSNVTKETQ
961 PPDLPTTALG GCPSDWIQFL NKCFQVQGQE PQSRVKWSEA QFSCEQQEAQ LVTITNPLEQ
```

FIGURE 1B cont

```
1021 AFITASLPNV TFDLWIGLHA SQRDFQWVEQ EPLMYANWAP GEPSGPSPAP SGNKPTSCAV
1081 VLHSPSAHFT GRWDDRSCTE ETHGFICQKG TDPSLSPSPA ALPPAPGTEL SYLNGTFRLL
1141 QKPLRWHDAL LLCESHNASL AYVPDPYTQA FLTQAARGLR TPLWIGLAGE EGSRRYSWVS
1201 EEPLNYVGWQ DGEPQQPGGC TYVDVDGAWR TTSCDTKLQG AVCGVSSGPP PPRRISYHGS
1261 CPQGLADSAW IPFREHCYSF HMELLLGHKE ARQRCQRAGG AVLSILDEME NVFVWEHLQS
1321 YEGQSRGAWL GMNFNPKGGT LVWQDNTAVN YSNWGPPGLG PSMLSHNSCY WIQSNSGLWR
1381 PGACTNITMG VVCKLPRAEQ SSFSPSALPE NPAALVVVLM AVLLLLALLT AALILYRRRQ
1441 SIERGAFEGA RYSRSSSSPT EATEKNILVS DMEMNEQQE
```

FIGURE 1C

```
ATGGGGCCCGGCCGGCCGGCCCCCGCGCCCTGGCCTCGTCACCTGCTGCGCTGCGTCCTG
CTCCTCGGGTGCCTGCACCTCGGCCGTCCCGGCGCCCCTGGGGACGCCGCCCTCCCGGAA
CCCAACGTCTTCCTCATCTTCAGCCATGGACTGCAGGGCTGCCTGGAGGCCCAGGGCGGG
CAGGTCAGAGTCACCCCGGCTTGCAATACCAGCCTCCCTGCCCAGCGCTGGAAGTGGGTC
TCCCGAAACCGGCTATTCAACCTGGGTACCATGCAGTGCCTGGGCACAGGCTGGCCAGGC
ACCAACACCACGGCCTCCCTGGGCATGTATGAGTGTGACCGGGAAGCACTGAATCTTCGC
TGGCATTGTCGTACACTGGGTGACCAGCTGTCCTTGCTCCTGGGGGCCCGCACCAGCAAC
ATATCCAAGCCTGGCACCCTTGAGCGTGGTGACCAGACCCGCAGTGGCCAGTGGCGCATC
TACGGCAGCGAGGAGGACCTATGTGCTCTGCCCTACCACGAGGTCTACACCATCCAGGGA
AACTCCCACGGAAAGCCGTGCACCATCCCCTTCAAATATGACAACCAGTGGTTCCACGGC
TGCACCAGCACGGGCCGCGAGGATGGTCACCTGTGGTGTGCCACCACCCAGGACTACGGC
AAAGACGAGCGCTGGGGCTTCTGCCCCATCAAGAGTAACGACTGCGAGACCTTCTGGGAC
AAGGACCAGCTGACTGACAGCTGCTACCAGTTTAACTTCCAGTCCACGCTGTCGTGGAGG
GAGGCCTGGGCCAGCTGCGAGCAGCAGGGTGCGGATCTGCTGAGCATCACGGAGATCCAC
GAGCAGACCTACATCAACGGCCTCCTCACTGGGTACAGCTCCACCCTGTGGATCGGCTTG
AATGACTTGGACACGAGCGGAGGCTGGCAGTGGTCGGACAACTCGCCCCTCAAGTACCTC
AACTGGGAGAGTGACCAGCCGGACAACCCCAGTGAGGAGAACTGTGGAGTGATCCGCACT
GAGTCCTCGGGCGGCTGGCAGAACCGTGACTGCAGCATCGCGCTGCCCTATGTGTGCAAG
AAGAAGCCCAACGCCACGGCCGAGCCCACCCCTCCAGACAGGTGGGCCAATGTGAAGGTG
GAGTGCGAGCCGAGCTGGCAGCCCTTCCAGGGCCACTGCTACCGCCTGCAGGCCGAGAAG
CGCAGCTGGCAGGAGTCCAAGAAGGCATGTCTACGGGGCGGTGGCGACCTGGTCAGCATC
CACAGCATGGCGGAGCTGGAATTCATCACCAAGCAGATCAAGCAAGAGGTGGAGGAGCTG
TGGATCGGCCTCAACGATTTGAAACTGCAGATGAATTTTGAGTGGTCTGACGGGAGCCTT
GTGAGCTTCACCCACTGGCACCCCTTTGAGCCCAACAACTTCCGGGACAGTCTGGAGGAC
TGTGTCACCATCTGGGGCCCGGAAGGCCGCTGGAACGACAGTCCCTGTAACCAGTCCTTG
CCATCCATCTGCAAGAAGGCAGGCCAGCTGAGCCAGGGGGCCGCCGAGGAGGACCATGGC
TGCCGGGATTACAAGGACGACGACGATAAGTGA
```

FIGURE 1D

```
MGPGRPAPAPWPRHLLRCVLLLGCLHLGRPGAPGDAALPEPNVFLIFSHGLQGCLEAQGG
QVRVTPACNTSLPAQRWKWVSRNRLFNLGTMQCLGTGWPGTNTTASLGMYECDREALNLR
WHCRTLGDQLSLLLGARTSNISKPGTLERGDQTRSGQWRIYGSEEDLCALPYHEVYTIQG
NSHGKPCTIPFKYDNQWFHGCTSTGREDGHLWCATTQDYGKDERWGFCPIKSNDCETFWD
KDQLTDSCYQFNFQSTLSWREAWASCEQQGADLLSITEIHEQTYINGLLTGYSSTLWIGL
NDLDTSGGWQWSDNSPLKYLNWESDQPDNPSEENCGVIRTESSGGWQNRDCSIALPYVCK
KKPNATAEPTPPDRWANVKVECEPSWQPFQGHCYRLQAEKRSWQESKKACLRGGGDLVSI
HSMAELEFITKQIKQEVEELWIGLNDLKLQMNFEWSDGSLVSFTHWHPFEPNNFRDSLED
CVTIWCPECRWNDSPCNQSLPSICKKAGQLSQCAAEEDHCCRDYKDDDDK
```

FIGURE 1E

TAATGTGAGTTAGCTACTCTTAGGCACCCCAGGCTTTACACTTTATGCTTCCGGCTCGTATGTTGTGTGG
AATTGTGAGCGGATAACAATTTCACACAGGAAACAGCTATGACCATGATTACGCCAAGCTTGCCAAATTC
TATTTCAAGGAGACAGTCATAATGAAATACCTATTGCCTACGGCAGCCGCTGGATTGTTATTACTCGCAG
CAAGCGGCGCGCATGCCCAGGTGCAGCTGGTGCAGTCTGGGGGAGGCCTGGTCAAGCCTGGGGGGTCCCT
GAGACTCTCCTGTGCAGCCTCTGGATTCACCTTCAGTAGCTATAGCATGAACTGGGTCCGCCAGGCTCCA
GGGAAGGGGCTGGAGTGGGTGGCCAACATAAAGCCAGATGGAAGTGAGAGACACTCTGTGGACTCTGTGA
AGGGCCGATTCACCATCTCCAGAGACAACTCCAAGAACTCACTGTATCTGCAAATGAACAGCCTGAGAGC
CGAGGACACGGCTGTTTATTACTGTGCGCGACCCGGGGCTGGGCGACTTGACTACTGGGGCCAGGGCACC
CTGGTCACCGTCTCCTCAGGTGGAGGCGGTTCAGGCGGAGGTGGCTCTGGCGGTGGCGGATCGAATTTTA
TGCTGACTCAGGACGCTGCTGTGTCTGTGGCCTTGGGACAGACAGTCAGGATCACATGCCAAGGAGACAG
CCTCAGAAGCTATTATGCAAGCTGGTACCAACAGAAGCCAGGACAGGCCCCTGTACTTGTCGTCTATGGT
AAAAACAACCGACCCTCAGGGATCCCAGACCGATTCTCTGGCTCCAGCTCAGGAAACACAGCTTCCTTGA
CCATCACTGGGGCTCAGGCGGAAGATGAGGCTGACTATTACTGTAACTCCCGGGACAGCAGTGGTAACCC
CTGGGCGTTCGGCGGAGGGACCAAGGTGACCGTCCTAGCTAGCGGCAAACCAATCCCAAACCCACTGCTG
GGCCTGGATAGTACTCACCATCACCATCACCATTAGGCGGCCGCTACTGTTGAAAGTTGTTTAGCAAAAC
CTCATACAGAAAATTCATTTACTAACGTCTGGAAAGACGACAAAACTTTAGATCGTTACGCTAACTATGA
GGGCTTG

CDR3-H CARPGAGRLDYW

FIGURE 1H

CDR3-L CNSRDSSGNPWAF

FIGURE 1J

MGPGRPAPAPWPRHLLRCVLLLGCLHLGRPGAPGDAALPEPNVFLIFSHGLQGCLEAQGG
QVRVTPACNTSLPAQRWKWVSRNRLFNLGTMQCLGTGWPGTNTTASLGMYECDREALNLR
WHCRTLGDQLSLLLGARTSNISKPGTLERGDQTRSGQWRIYGSEEDLCALPYHEVYTIQG
NSHGKPCTIPFKYDNQWFHGCTSTGREDGHLWCATTQDYGKDERWGFCPIKSNDCETFWD
KDQLTDSCYQFNFQSTLSWREAWASCEQQGADLLSITEIHEQTYINGLLTGYSSTLWIGL
NDLDTSGGWQWSDNSPLKYLNWESDQPDNPSEENCGVIRTESSGGWQNRDCSIALPYVCK
KKPNATAEPTPPDRWANVKVECEPSWQPFQGHCYRLQAEKRSWQESKKACLRGGGDLVSI
HSMAELEFITKQIKQEVEELWIGLNDLKLQMNFEWSDGSLVSFTHWHPFEPNNFRDSLED
CVTIWGPEGRWNDSPCNQSLPSICKKAGQLSQGAAEEDHGCR

FIGURE 3:

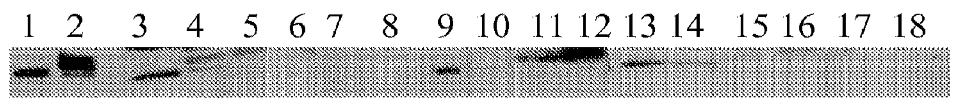

1. E3 8D8-Biotin
2. NMIgG-Biotin
3. Mouse #26 injected with E3 8D8-Biotin, UUO kidney
4. Mouse #26 injected with E3 8D8-Biotin, Contra-lateral kidney
5. Mouse #38injected with NMIgG-Biotin, UUO kidney
6. Mouse #38 injected with NMIgG-Biotin, Contra-lateral kidney
7. Mouse #50 injected with PBS, UUO kidney
8. Mouse #50 injected with PBS, Contra-lateral kidney
9. Mouse #33 injected with E3 8D8-Biotin, UUO kidney
10. Mouse #33 injected with E3 8D8-Biotin, Contra-lateral kidney
11. Mouse #40 injected with NMIgG-Biotin, UUO kidney
12. Mouse #40 injected with NMIgG-Biotin, Contra-lateral kidney
13. Mouse #27 injected with E3 8D8-Biotin, UUO kidney
14. Mouse #27 injected with E3 8D8-Biotin, Contra-lateral kidney
15. Mouse #36 injected with NMIgG-Biotin, UUO kidney
16. Mouse #36 injected with NMIgG-Biotin, Contra-lateral kidney
17. Mouse #37 injected with NMIgG-Biotin, UUO kidney
18. Mouse #37 injected with NMIgG-Biotin, Contra-lateral kidney

FIGURE 4A

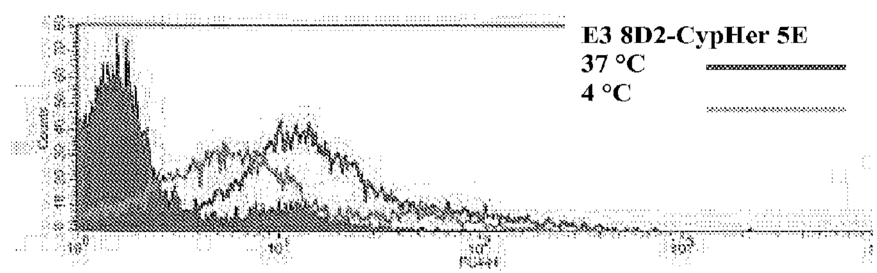

FIGURE 4B

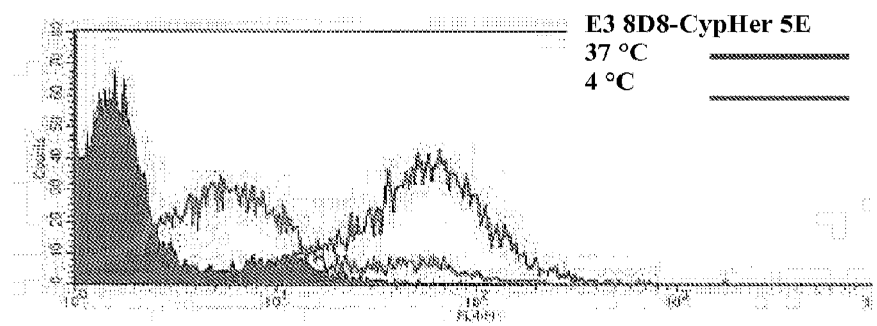

SEQUENCE LISTING

<160> NUMBER OF SEQ ID NOS: 9

<210> SEQ ID NO 1
<211> LENGTH: 5641
<212> TYPE: RNA
<213> ORGANISM: Homo sapiens

<400> SEQUENCE: 1

```
cggaggagga cgcgagcccc uugcgggcgg ucaucacagc ccagccucgg ggcugccaca      60

gcgcguugcg ccugugcgcc cucgguCccc gcguccacug agcgccgcgc ucggggaugg     120

ggcccggccg gccggccccc gcgcccuggc cucgucaccu gcugcgcugc guccugcucc     180

ucgggugccu gcaccucggc cgucccggcg ccccugggga cgccgcccuc ccggaaccca     240

acgucuuccu caucuucagc cauggacugc agggcugccu ggaggcccag ggcgggcagg     300

ucagagucac cccggcuugc aauaccagcc ucccugccca gcgcuggaag ugggucuccc     360

gaaaccggcu auucaaccug gguaccaugc agugccuggg cacaggcugg ccaggcacca     420

acaccacggc cucccugggc auguaugagu gugaccggga agcacugaau cuucgcuggc     480

auugucguac acugggugac cagcuguccu ugcuccuggg ggcccgcacc agcaacauau     540

ccaagccugg cacccuugag cguggugacc agacccgcag uggccagugg cgcaucuacg     600

gcagcgagga ggaccuaugu gcucugcccu accacgaggu cuacaccauc cagggaaacu     660

cccacggaaa gccgugcacc auccccuuca aauaugacaa ccagugguuc cacggcugca     720

ccagcacggg ccgcgaggau ggucaccugu ggugugccac cacccaggac uacggcaaag     780

acgagcgcug ggcuucugc cccaucaaga guaacgacug cgagaccuuc ugggacaagg     840
```

-continued accagcugac ugacagcugc uaccaguuua acuuccaguc cacgcugucg uggagggagg 900
ccugggccag cugcgagcag cagggugcgg aucugcugag caucacggag auccacgagc 960
agaccuacau caacggccuc cucacugggu acagcuccac ccuguggauc ggcuugaaug 1020
acuuggacac gagcggaggc uggcaguggu cggacaacuc gccccucaag uaccucaacu 1080
gggagaguga ccagccggac aaccccagug aggagaacug uggagugauc cgcacugagu 1140
ccucgggcgg cuggcagaac cgugacugca gcaucgcgcu gcccuaugug ugcaagaaga 1200
agcccaacgc cacggccgag cccaccccuc cagacaggug ggccaaugug aagguggagu 1260
gcgagccgag cuggcagccc uuccagggcc acugcuaccg ccugcaggcc gagaagcgca 1320
gcuggcagga guccaagaag gcaugucuac ggggcggugg cgaccugguc agcauccaca 1380
gcauggcgga gcuggaauuc aucaccaagc agaucaagca agagguggag gagcugugga 1440
ucggccucaa cgauuugaaa cugcagauga auuuugagug gucugacggg agccuuguga 1500
gcuucaccca cuggcacccc uuugagccca acaacuuccg ggacagucug gaggacugug 1560
ucaccaucug ggcccggaa ggccgcugga acgacagucc cuguaaccag uccuugccau 1620
ccaucugcaa gaaggcaggc cagcugagcc agggggccgc cgaggaggac cauggcugcc 1680
ggaaggguug gacguggcac agcccauccu gcuacuggcu gggagaagac caagugaccu 1740
acagugaggc ccggcgccug ugcacugacc auggcucuca gcuggucacc aucaccaaca 1800
gguucgagca ggccuucguc agcagccuca ucuacaacug ggagggcgag uacuucugga 1860
cggcccugca ggaccucaac agcaccggcu ccuucuucug gcucaguggg gaugaaguca 1920
uguacaccca cuggaaccgg gaccagcccg gguacagccg ugggggcugc guggcgcugg 1980
ccacuggcag cgccaugggg cugugggagg ugaagaacug uaccucguuc cgggcccgcu 2040
acaucugccg gcagagccug ggcacuccag ugacgccgga gcugccgggg ccagauccca 2100
cgcccagccu cacuggcucc uguccccagg gcugggccuc ggacaccaaa cuccgguauu 2160
gcuauaaggu guucagcuca gagcggcugc aggacaagaa gagcugggu caggcccagg 2220 gggccugcca ggagcugggg gcccagcugc ugagccuggc cagcuacgag gaggagcacu 2280
uuguggccaa caugcucaac aagaucuucg gugaaucaga acccgagauc cacgagcagc 2340
acugguucug gaucggccug aaccgucggg aucccagagg gggucagagu uggcgcugga 2400
gcgacggcgu aggguucucu uaccacaauu ucgaccggag ccggcacgac gacgacgaca 2460
uccgaggcug ugcggugcug gaccuggccu cccugcagug gguggccaug cagugcgaca 2520
cacagcugga cuggaucugc aagaucccca gagguacgga cgugcgggag cccgacgaca 2580
gcccucaagg ccgacgggaa uggcugcgcu uccaggaggc cgaguacaag uucuuugagc 2640
accacuccac gugggcgcag gcgcagcgca ucugcacgug guuccaggcc gagcugaccu 2700
ccgugcacag ccaggcagag cuagacuucc ugagccacaa cuugcagaag uucucccggg 2760
cccaggagca gcacuggugg aucggccugc acaccucuga gagcgauggg cgcuucagau 2820
ggacagaugg uuccauuaua aacuucaucu ccugggcacc aggcaaaccu cggccugucg 2880
gcaaggacaa gaagugcgug uacaugacag ccagccgaga ggacuggggg gaccagaggu 2940
gccugacagc cuugcccuac aucugcaagc gcagcaacgu caccaaagaa acgcagcccc 3000
cagaccugcc aacuacagcc cuggggggcu gccccucuga cuggauccag uuccucaaca 3060
aguguuuuca gguccagggc caggaacccc agagccgggu gaaguggucca gaggcacagu 3120 ucuccuguga acagcaagag gcccagcugg ucaccaucac aaaccccuua gagcaagcau 3180
ucaucacagc cagccugccc aaugugaccu uugaccuuug gauuggccuc caugccucgc 3240

```
agagggacuu ccagugggug gagcaggagc cuuugaugua ugccaacugg gcaccugggg 3300

agcccucugg cccuagcccu gcucccagug gcaacaaacc gaccagcugu gcgguggucc 3360

ugcacagccc cucagcccac uucacuggcc gcugggacga ucggagcugc acggaggaga 3420

cccauggcuu caucugccag aagggcacgg accccucccu gagcccgucc ccagcagcgc 3480

ugcccccgc cccgggcacu gagcucuccu accucaacgg caccuuccgg cugcuucaga 3540

agccgcugcg cuggcacgau gcccuccugc ugugugagag ccacaaugcc agccuggccu 3600

acgugcccga ccccuacacc caggccuucc ucacgcaggc ugcccgaggg cugcgcacgc 3660

cgcucuggau ugggcuggcu ggcgaggagg gcucucggcg guacuccugg gucucagagg 3720

agccgcugaa cuacgugggc uggcaggacg gggagccgca gcagccgggg ggcuguaccu 3780

acguagaugu ggacggggcc uggcgcacca ccagcuguga caccaagcug cagggggcug 3840

ugugugggu uagcaguggg cccccucuc cccgaagaau aagcuaccau ggcagcuguc 3900

cccagggacu ggcagacucc gcguggauuc ccuuccggga gcacugcuau ucuuuccaca 3960

uggagcugcu gcugggccac aaggaggcgc gacagcgcug ccagagagcg ggugggggccg 4020

uccugucuau ccuggaugag auggagaaug uguuugucug ggagcaccug cagagcuaug 4080

agggccagag ucggggcgcc uggcugggca ugaacuucaa ccccaaagga ggcacucugg 4140

ucuggcagga caacacagcu gugaacuacu ccaacugggg gcccccgggc uugggcccca 4200

gcaugcugag ccacaacagc ugcuacugga uucagagcaa cagcgggcua uggcgccccg 4260

gcgcuugcac caacaucacc augggugucg ucugcaagcu uccucgugcu gagcagagca 4320

gcuucucccc aucagcgcuu ccagagaacc cagcggcccu gguggugug cugauggcgg 4380

ugcugcugcu ccuggccuug cugaccgcag cccucauccu uuaccggagg cgccagagca 4440

ucgagcgcgg ggccuuugag ggugcccgcu acagccgcag cagcuccagc cccaccgagg 4500

ccacugagaa gaacauccug gugucagaca uggaaaugaa ugagcaacaa gaauagagcc 4560

aggcgcgugg gcagggccag ggcgggagga gcuggggagc uggggcccug ggucagucug 4620

gcccccacc agcugccugu ccaguuggcc uauggaaggg ugcccuuggg agucgcuguu 4680

gggagccgga gcugggcaga gccugggcug guggggugcc acccucccac aagggcuggg 4740

cugagaccca gcugagugca gcguggcguu ucccuuucug ggggggccug aggucuuguc 4800

accugguccu gugcccccac aggaaccaga gguaggaugg gaggggggaac gagagccucu 4860

uucuccccag agccccggc ccaggccugu ugauccgcgc cccaggaccc ccuucuuugc 4920

agagcccgag gagccucccc uguccccucg ggcagaucug uugugucucu cuucccaccu 4980

ggcagccuca gcucugugcc ccucacccug cucccucucg ccccuucucu cccaccccuu 5040

ccuucugagc cgggcccugg ggauugggga gcccucuugu uccugaugag ggucagcuga 5100

gggggcugag cauccaucac uccugugccu gcuggggugg cugugggcg uggcaggagg 5160

ggccuaggug gguugggccu gagaaccagg gcacgggugu ggugucugcu gggcuggaga 5220

uaagacuggg gagagacacc ccaaccuccc agggugggag cugggccggg cugggauguc 5280

aucuccugcc gggcgggga gggcucugcc ccuggaagag uccccugugg ggaccaaaau 5340

aaguucccua acaucuccag cuccuggcuc ugguuuggag caaggggaag gguugccaga 5400

guccuggggg ccccagagga gcaggagucu gggagggccc agaguucacc cucuagugga 5460

uccaggagga gcagcacccg agcccuggag uggcccagua cccuuccaag aggccacagu 5520

cccagccagg acaaaguaug cggcccaucc uggugcgaca gcgugggaca augugaacau 5580

ggacucgaag acauggcccu uucucuguag uugauuuuuu aaaugugcca uuauuguuuu 5640
```

u 5641

<210> SEQ ID NO 2
<211> LENGTH: 1479
<212> TYPE: PRT
<213> ORGANISM: Homo sapiens

<400> SEQUENCE: 2

```
Met Gly Pro Gly Arg Pro Ala Pro Ala Pro Trp Pro Arg His Leu Leu
1               5                   10                  15

Arg Cys Val Leu Leu Leu Gly Cys Leu His Leu Gly Arg Pro Gly Ala
            20                  25                  30

Pro Gly Asp Ala Ala Leu Pro Glu Pro Asn Val Phe Leu Ile Phe Ser
        35                  40                  45

His Gly Leu Gln Gly Cys Leu Glu Ala Gln Gly Gly Gln Val Arg Val
    50                  55                  60

Thr Pro Ala Cys Asn Thr Ser Leu Pro Ala Gln Arg Trp Lys Trp Val
65                  70                  75                  80

Ser Arg Asn Arg Leu Phe Asn Leu Gly Thr Met Gln Cys Leu Gly Thr
                85                  90                  95

Gly Trp Pro Gly Thr Asn Thr Thr Ala Ser Leu Gly Met Tyr Glu Cys
            100                 105                 110

Asp Arg Glu Ala Leu Asn Leu Arg Trp His Cys Arg Thr Leu Gly Asp
        115                 120                 125

Gln Leu Ser Leu Leu Leu Gly Ala Arg Thr Ser Asn Ile Ser Lys Pro
    130                 135                 140

Gly Thr Leu Glu Arg Gly Asp Gln Thr Arg Ser Gly Gln Trp Arg Ile
145                 150                 155                 160

Tyr Gly Ser Glu Glu Asp Leu Cys Ala Leu Pro Tyr His Glu Val Tyr
                165                 170                 175

Thr Ile Gln Gly Asn Ser His Gly Lys Pro Cys Thr Ile Pro Phe Lys
            180                 185                 190

Tyr Asp Asn Gln Trp Phe His Gly Cys Thr Ser Thr Gly Arg Glu Asp
        195                 200                 205

Gly His Leu Trp Cys Ala Thr Thr Gln Asp Tyr Gly Lys Asp Glu Arg
    210                 215                 220

Trp Gly Phe Cys Pro Ile Lys Ser Asn Asp Cys Glu Thr Phe Trp Asp
225                 230                 235                 240

Lys Asp Gln Leu Thr Asp Ser Cys Tyr Gln Phe Asn Phe Gln Ser Thr
                245                 250                 255

Leu Ser Trp Arg Glu Ala Trp Ala Ser Cys Glu Gln Gln Gly Ala Asp
            260                 265                 270

Leu Leu Ser Ile Thr Glu Ile His Glu Gln Thr Tyr Ile Asn Gly Leu
        275                 280                 285

Leu Thr Gly Tyr Ser Ser Thr Leu Trp Ile Gly Leu Asn Asp Leu Asp
    290                 295                 300

Thr Ser Gly Gly Trp Gln Trp Ser Asp Asn Ser Pro Leu Lys Tyr Leu
305                 310                 315                 320

Asn Trp Glu Ser Asp Gln Pro Asp Asn Pro Ser Glu Glu Asn Cys Gly
                325                 330                 335

Val Ile Arg Thr Glu Ser Ser Gly Gly Trp Gln Asn Arg Asp Cys Ser
            340                 345                 350

Ile Ala Leu Pro Tyr Val Cys Lys Lys Lys Pro Asn Ala Thr Ala Glu
        355                 360                 365
```

```
Pro Thr Pro Pro Asp Arg Trp Ala Asn Val Lys Val Glu Cys Glu Pro
    370                 375                 380

Ser Trp Gln Pro Phe Gln Gly His Cys Tyr Arg Leu Gln Ala Glu Lys
385                 390                 395                 400

Arg Ser Trp Gln Glu Ser Lys Lys Ala Cys Leu Arg Gly Gly Gly Asp
                405                 410                 415

Leu Val Ser Ile His Ser Met Ala Glu Leu Glu Phe Ile Thr Lys Gln
            420                 425                 430

Ile Lys Gln Glu Val Glu Glu Leu Trp Ile Gly Leu Asn Asp Leu Lys
        435                 440                 445

Leu Gln Met Asn Phe Glu Trp Ser Asp Gly Ser Leu Val Ser Phe Thr
    450                 455                 460

His Trp His Pro Phe Glu Pro Asn Asn Phe Arg Asp Ser Leu Glu Asp
465                 470                 475                 480

Cys Val Thr Ile Trp Gly Pro Glu Gly Arg Trp Asn Asp Ser Pro Cys
                485                 490                 495

Asn Gln Ser Leu Pro Ser Ile Cys Lys Lys Ala Gly Gln Leu Ser Gln
            500                 505                 510

Gly Ala Ala Glu Glu Asp His Gly Cys Arg Lys Gly Trp Thr Trp His
        515                 520                 525

Ser Pro Ser Cys Tyr Trp Leu Gly Glu Asp Gln Val Thr Tyr Ser Glu
    530                 535                 540

Ala Arg Arg Leu Cys Thr Asp His Gly Ser Gln Leu Val Thr Ile Thr
545                 550                 555                 560

Asn Arg Phe Glu Gln Ala Phe Val Ser Ser Leu Ile Tyr Asn Trp Glu
                565                 570                 575

Gly Glu Tyr Phe Trp Thr Ala Leu Gln Asp Leu Asn Ser Thr Gly Ser
            580                 585                 590

Phe Phe Trp Leu Ser Gly Asp Glu Val Met Tyr Thr His Trp Asn Arg
        595                 600                 605

Asp Gln Pro Gly Tyr Ser Arg Gly Gly Cys Val Ala Leu Ala Thr Gly
    610                 615                 620

Ser Ala Met Gly Leu Trp Glu Val Lys Asn Cys Thr Ser Phe Arg Ala
625                 630                 635                 640

Arg Tyr Ile Cys Arg Gln Ser Leu Gly Thr Pro Val Thr Pro Glu Leu
                645                 650                 655

Pro Gly Pro Asp Pro Thr Pro Ser Leu Thr Gly Ser Cys Pro Gln Gly
            660                 665                 670

Trp Ala Ser Asp Thr Lys Leu Arg Tyr Cys Tyr Lys Val Phe Ser Ser
        675                 680                 685

Glu Arg Leu Gln Asp Lys Lys Ser Trp Val Gln Ala Gln Gly Ala Cys
    690                 695                 700

Gln Glu Leu Gly Ala Gln Leu Leu Ser Leu Ala Ser Tyr Glu Glu Glu
705                 710                 715                 720

His Phe Val Ala Asn Met Leu Asn Lys Ile Phe Gly Glu Ser Glu Pro
                725                 730                 735

Glu Ile His Glu Gln His Trp Phe Trp Ile Gly Leu Asn Arg Arg Asp
            740                 745                 750

Pro Arg Gly Gly Gln Ser Trp Arg Trp Ser Asp Gly Val Gly Phe Ser
        755                 760                 765

Tyr His Asn Phe Asp Arg Ser Arg His Asp Asp Asp Asp Ile Arg Gly
    770                 775                 780

Cys Ala Val Leu Asp Leu Ala Ser Leu Gln Trp Val Ala Met Gln Cys
785                 790                 795                 800
```

```
Asp Thr Gln Leu Asp Trp Ile Cys Lys Ile Pro Arg Gly Thr Asp Val
                805                 810                 815

Arg Glu Pro Asp Asp Ser Pro Gln Gly Arg Arg Glu Trp Leu Arg Phe
            820                 825                 830

Gln Glu Ala Glu Tyr Lys Phe Phe Glu His His Ser Thr Trp Ala Gln
        835                 840                 845

Ala Gln Arg Ile Cys Thr Trp Phe Gln Ala Glu Leu Thr Ser Val His
    850                 855                 860

Ser Gln Ala Glu Leu Asp Phe Leu Ser His Asn Leu Gln Lys Phe Ser
865                 870                 875                 880

Arg Ala Gln Glu Gln His Trp Trp Ile Gly Leu His Thr Ser Glu Ser
                885                 890                 895

Asp Gly Arg Phe Arg Trp Thr Asp Gly Ser Ile Ile Asn Phe Ile Ser
            900                 905                 910

Trp Ala Pro Gly Lys Pro Arg Pro Val Gly Lys Asp Lys Lys Cys Val
        915                 920                 925

Tyr Met Thr Ala Ser Arg Glu Asp Trp Gly Asp Gln Arg Cys Leu Thr
    930                 935                 940

Ala Leu Pro Tyr Ile Cys Lys Arg Ser Asn Val Thr Lys Glu Thr Gln
945                 950                 955                 960

Pro Pro Asp Leu Pro Thr Thr Ala Leu Gly Gly Cys Pro Ser Asp Trp
                965                 970                 975

Ile Gln Phe Leu Asn Lys Cys Phe Gln Val Gln Gly Gln Glu Pro Gln
            980                 985                 990

Ser Arg Val Lys Trp Ser Glu Ala  Gln Phe Ser Cys Glu  Gln Gln Glu
        995                 1000                1005

Ala Gln  Leu Val Thr Ile Thr  Asn Pro Leu Glu Gln  Ala Phe Ile
    1010                1015                1020

Thr Ala  Ser Leu Pro Asn Val  Thr Phe Asp Leu Trp  Ile Gly Leu
    1025                1030                1035

His Ala  Ser Gln Arg Asp Phe  Gln Trp Val Glu Gln  Glu Pro Leu
    1040                1045                1050

Met Tyr  Ala Asn Trp Ala Pro  Gly Glu Pro Ser Gly  Pro Ser Pro
    1055                1060                1065

Ala Pro  Ser Gly Asn Lys Pro  Thr Ser Cys Ala Val  Val Leu His
    1070                1075                1080

Ser Pro  Ser Ala His Phe Thr  Gly Arg Trp Asp Asp  Arg Ser Cys
    1085                1090                1095

Thr Glu  Glu Thr His Gly Phe  Ile Cys Gln Lys Gly  Thr Asp Pro
    1100                1105                1110

Ser Leu  Ser Pro Ser Pro Ala  Ala Leu Pro Pro Ala  Pro Gly Thr
    1115                1120                1125

Glu Leu  Ser Tyr Leu Asn Gly  Thr Phe Arg Leu Leu  Gln Lys Pro
    1130                1135                1140

Leu Arg  Trp His Asp Ala Leu  Leu Leu Cys Glu Ser  His Asn Ala
    1145                1150                1155

Ser Leu  Ala Tyr Val Pro Asp  Pro Tyr Thr Gln Ala  Phe Leu Thr
    1160                1165                1170

Gln Ala  Ala Arg Gly Leu Arg  Thr Pro Leu Trp Ile  Gly Leu Ala
    1175                1180                1185

Gly Glu  Glu Gly Ser Arg Arg  Tyr Ser Trp Val Ser  Glu Glu Pro
    1190                1195                1200

Leu Asn  Tyr Val Gly Trp Gln  Asp Gly Glu Pro Gln  Gln Pro Gly
```

```
    1205                1210                1215

Gly Cys  Thr Tyr Val Asp Val  Asp Gly Ala Trp Arg  Thr Thr Ser
    1220                1225                1230

Cys Asp  Thr Lys Leu Gln Gly  Ala Val Cys Gly Val  Ser Ser Gly
    1235                1240                1245

Pro Pro  Pro Pro Arg Arg Ile  Ser Tyr His Gly Ser  Cys Pro Gln
    1250                1255                1260

Gly Leu  Ala Asp Ser Ala Trp  Ile Pro Phe Arg Glu  His Cys Tyr
    1265                1270                1275

Ser Phe  His Met Glu Leu Leu  Leu Gly His Lys Glu  Ala Arg Gln
    1280                1285                1290

Arg Cys  Gln Arg Ala Gly Gly  Ala Val Leu Ser Ile  Leu Asp Glu
    1295                1300                1305

Met Glu  Asn Val Phe Val Trp  Glu His Leu Gln Ser  Tyr Glu Gly
    1310                1315                1320

Gln Ser  Arg Gly Ala Trp Leu  Gly Met Asn Phe Asn  Pro Lys Gly
    1325                1330                1335

Gly Thr  Leu Val Trp Gln Asp  Asn Thr Ala Val Asn  Tyr Ser Asn
    1340                1345                1350

Trp Gly  Pro Pro Gly Leu Gly  Pro Ser Met Leu Ser  His Asn Ser
    1355                1360                1365

Cys Tyr  Trp Ile Gln Ser Asn  Ser Gly Leu Trp Arg  Pro Gly Ala
    1370                1375                1380

Cys Thr  Asn Ile Thr Met Gly  Val Val Cys Lys Leu  Pro Arg Ala
    1385                1390                1395

Glu Gln  Ser Ser Phe Ser Pro  Ser Ala Leu Pro Glu  Asn Pro Ala
    1400                1405                1410

Ala Leu  Val Val Val Leu Met  Ala Val Leu Leu Leu  Leu Ala Leu
    1415                1420                1425

Leu Thr  Ala Ala Leu Ile Leu  Tyr Arg Arg Arg Gln  Ser Ile Glu
    1430                1435                1440

Arg Gly  Ala Phe Glu Gly Ala  Arg Tyr Ser Arg Ser  Ser Ser Ser
    1445                1450                1455

Pro Thr  Glu Ala Thr Glu Lys  Asn Ile Leu Val Ser  Asp Met Glu
    1460                1465                1470

Met Asn  Glu Gln Gln Glu
    1475


<210> SEQ ID NO 3
<211> LENGTH: 1593
<212> TYPE: DNA
<213> ORGANISM: Homo sapiens

<400> SEQUENCE: 3

atggggcccg gccggccggc cccgcgcccc tggcctcgtc acctgctgcg ctgcgtcctg      60

ctcctcgggt gcctgcacct cggccgtccc ggcgcccctg gggacgccgc cctcccggaa     120

cccaacgtct tcctcatctt cagccatgga ctgcagggct gcctggaggc ccagggcggg     180

caggtcagag tcaccccggc ttgcaatacc agcctccctg cccagcgctg gaagtgggtc     240

tcccgaaacc ggctattcaa cctgggtacc atgcagtgcc tgggcacagg ctggccaggc     300

accaacacca cggcctccct gggcatgtat gagtgtgacc gggaagcact gaatcttcgc     360

tggcattgtc gtacactggg tgaccagctg tccttgctcc tgggggcccg caccagcaac     420

atatccaagc ctggcaccct tgagcgtggt gaccagaccc gcagtggcca gtggcgcatc     480
```

```
tacggcagcg aggaggacct atgtgctctg ccctaccacg aggtctacac catccaggga     540

aactcccacg gaaagccgtg caccatcccc ttcaaatatg acaaccagtg gttccacggc     600

tgcaccagca cgggccgcga ggatggtcac ctgtggtgtg ccaccaccca ggactacggc     660

aaagacgagc gctggggctt ctgccccatc aagagtaacg actgcgagac cttctgggac     720

aaggaccagc tgactgacag ctgctaccag tttaacttcc agtccacgct gtcgtggagg     780

gaggcctggg ccagctgcga gcagcagggt gcggatctgc tgagcatcac ggagatccac     840

gagcagacct acatcaacgg cctcctcact gggtacagct ccaccctgtg gatcggcttg     900

aatgacttgg acacgagcgg aggctggcag tggtcggaca actcgcccct caagtacctc     960

aactgggaga gtgaccagcc ggacaacccc agtgaggaga actgtggagt gatccgcact    1020

gagtcctcgg gcggctggca gaaccgtgac tgcagcatcg cgctgcccta tgtgtgcaag    1080

aagaagccca acgccacggc cgagcccacc cctccagaca ggtgggccaa tgtgaaggtg    1140

gagtgcgagc cgagctggca gcccttccag ggccactgct accgcctgca ggccgagaag    1200

cgcagctggc aggagtccaa gaaggcatgt ctacggggcg gtggcgacct ggtcagcatc    1260

cacagcatgg cggagctgga attcatcacc aagcagatca agcaagaggt ggaggagctg    1320

tggatcggcc tcaacgattt gaaactgcag atgaatttg agtggtctga cgggagcctt    1380

gtgagcttca cccactggca ccccttttgag cccaacaact tccgggacag tctggaggac    1440

tgtgtcacca tctggggccc ggaaggccgc tggaacgaca gtccctgtaa ccagtccttg    1500

ccatccatct gcaagaaggc aggccagctg agccaggggg ccgccgagga ggaccatggc    1560

tgccgggatt acaaggacga cgacgataag tga                                 1593
```

```
<210> SEQ ID NO 4
<211> LENGTH: 530
<212> TYPE: PRT
<213> ORGANISM: Homo sapiens

<400> SEQUENCE: 4

Met Gly Pro Gly Arg Pro Ala Pro Ala Pro Trp Pro Arg His Leu Leu
1               5                   10                  15

Arg Cys Val Leu Leu Leu Gly Cys Leu His Leu Gly Arg Pro Gly Ala
            20                  25                  30

Pro Gly Asp Ala Ala Leu Pro Glu Pro Asn Val Phe Leu Ile Phe Ser
        35                  40                  45

His Gly Leu Gln Gly Cys Leu Glu Ala Gln Gly Gly Gln Val Arg Val
    50                  55                  60

Thr Pro Ala Cys Asn Thr Ser Leu Pro Ala Gln Arg Trp Lys Trp Val
65                  70                  75                  80

Ser Arg Asn Arg Leu Phe Asn Leu Gly Thr Met Gln Cys Leu Gly Thr
                85                  90                  95

Gly Trp Pro Gly Thr Asn Thr Thr Ala Ser Leu Gly Met Tyr Glu Cys
            100                 105                 110

Asp Arg Glu Ala Leu Asn Leu Arg Trp His Cys Arg Thr Leu Gly Asp
        115                 120                 125

Gln Leu Ser Leu Leu Leu Gly Ala Arg Thr Ser Asn Ile Ser Lys Pro
    130                 135                 140

Gly Thr Leu Glu Arg Gly Asp Gln Thr Arg Ser Gly Gln Trp Arg Ile
145                 150                 155                 160

Tyr Gly Ser Glu Glu Asp Leu Cys Ala Leu Pro Tyr His Glu Val Tyr
                165                 170                 175

Thr Ile Gln Gly Asn Ser His Gly Lys Pro Cys Thr Ile Pro Phe Lys
```

```
            180                 185                 190

Tyr Asp Asn Gln Trp Phe His Gly Cys Thr Ser Thr Gly Arg Glu Asp
        195                 200                 205

Gly His Leu Trp Cys Ala Thr Thr Gln Asp Tyr Gly Lys Asp Glu Arg
    210                 215                 220

Trp Gly Phe Cys Pro Ile Lys Ser Asn Asp Cys Glu Thr Phe Trp Asp
225                 230                 235                 240

Lys Asp Gln Leu Thr Asp Ser Cys Tyr Gln Phe Asn Phe Gln Ser Thr
                245                 250                 255

Leu Ser Trp Arg Glu Ala Trp Ala Ser Cys Glu Gln Gln Gly Ala Asp
            260                 265                 270

Leu Leu Ser Ile Thr Glu Ile His Glu Gln Thr Tyr Ile Asn Gly Leu
        275                 280                 285

Leu Thr Gly Tyr Ser Ser Thr Leu Trp Ile Gly Leu Asn Asp Leu Asp
    290                 295                 300

Thr Ser Gly Gly Trp Gln Trp Ser Asp Asn Ser Pro Leu Lys Tyr Leu
305                 310                 315                 320

Asn Trp Glu Ser Asp Gln Pro Asp Asn Pro Ser Glu Glu Asn Cys Gly
                325                 330                 335

Val Ile Arg Thr Glu Ser Ser Gly Gly Trp Gln Asn Arg Asp Cys Ser
            340                 345                 350

Ile Ala Leu Pro Tyr Val Cys Lys Lys Lys Pro Asn Ala Thr Ala Glu
        355                 360                 365

Pro Thr Pro Pro Asp Arg Trp Ala Asn Val Lys Val Glu Cys Glu Pro
    370                 375                 380

Ser Trp Gln Pro Phe Gln Gly His Cys Tyr Arg Leu Gln Ala Glu Lys
385                 390                 395                 400

Arg Ser Trp Gln Glu Ser Lys Lys Ala Cys Leu Arg Gly Gly Gly Asp
                405                 410                 415

Leu Val Ser Ile His Ser Met Ala Glu Leu Glu Phe Ile Thr Lys Gln
            420                 425                 430

Ile Lys Gln Glu Val Glu Glu Leu Trp Ile Gly Leu Asn Asp Leu Lys
        435                 440                 445

Leu Gln Met Asn Phe Glu Trp Ser Asp Gly Ser Leu Val Ser Phe Thr
    450                 455                 460

His Trp His Pro Phe Glu Pro Asn Asn Phe Arg Asp Ser Leu Glu Asp
465                 470                 475                 480

Cys Val Thr Ile Trp Gly Pro Glu Gly Arg Trp Asn Asp Ser Pro Cys
                485                 490                 495

Asn Gln Ser Leu Pro Ser Ile Cys Lys Lys Ala Gly Gln Leu Ser Gln
            500                 505                 510

Gly Ala Ala Glu Glu Asp His Gly Cys Arg Asp Tyr Lys Asp Asp Asp
        515                 520                 525

Asp Lys
    530

<210> SEQ ID NO 5
<211> LENGTH: 1127
<212> TYPE: DNA
<213> ORGANISM: Homo sapiens

<400> SEQUENCE: 5

taatgtgagt tagctactct taggcacccc aggctttaca ctttatgctt ccggctcgta      60

tgttgtgtgg aattgtgagc ggataacaat ttcacacagg aaacagctat gaccatgatt     120
```

-continued

```
acgccaagct tgccaaattc tatttcaagg agacagtcat aatgaaatac ctattgccta    180

cggcagccgc tggattgtta ttactcgcag caagcggcgc gcatgcccag gtgcagctgg    240

tgcagtctgg gggaggcctg gtcaagcctg gggggtccct gagactctcc tgtgcagcct    300

ctggattcac cttcagtagc tatagcatga actgggtccg ccaggctcca gggaaggggc    360

tggagtgggt ggccaacata aagccagatg gaagtgagag acactctgtg gactctgtga    420

agggccgatt caccatctcc agagacaact ccaagaactc actgtatctg caaatgaaca    480

gcctgagagc cgaggacacg gctgtttatt actgtgcgcg acccggggct gggcgacttg    540

actactgggg ccagggcacc ctggtcaccg tctcctcagg tggaggcggt tcaggcggag    600

gtggctctgg cggtggcgga tcgaatttta tgctgactca ggacgctgct gtgtctgtgg    660

ccttgggaca gacagtcagg atcacatgcc aaggagacag cctcagaagc tattatgcaa    720

gctggtacca acagaagcca ggacaggccc ctgtacttgt cgtctatggt aaaaacaacc    780

gaccctcagg gatcccagac cgattctctg gctccagctc aggaaacaca gcttccttga    840

ccatcactgg ggctcaggcg gaagatgagg ctgactatta ctgtaactcc cgggacagca    900

gtggtaaccc ctgggcgttc ggcggaggga ccaaggtgac cgtcctagct agcggcaaac    960

caatcccaaa cccactgctg ggcctggata gtactcacca tcaccatcac cattaggcgg   1020

ccgctactgt tgaaagttgt ttagcaaaac ctcatacaga aaattcattt actaacgtct   1080

ggaaagacga caaaacttta gatcgttacg ctaactatga gggcttg                 1127
```

<210> SEQ ID NO 6
<211> LENGTH: 284
<212> TYPE: PRT
<213> ORGANISM: Homo sapiens

<400> SEQUENCE: 6

```
Met Lys Tyr Leu Leu Pro Thr Ala Ala Ala Gly Leu Leu Leu Leu Ala
1               5                   10                  15

Ala Ser Gly Ala His Ala Gln Val Gln Leu Val Gln Ser Gly Gly Gly
            20                  25                  30

Leu Val Lys Pro Gly Gly Ser Leu Arg Leu Ser Cys Ala Ala Ser Gly
        35                  40                  45

Phe Thr Phe Ser Ser Tyr Ser Met Asn Trp Val Arg Gln Ala Pro Gly
    50                  55                  60

Lys Gly Leu Glu Trp Val Ala Asn Ile Lys Pro Asp Gly Ser Glu Arg
65                  70                  75                  80

His Ser Val Asp Ser Val Lys Gly Arg Phe Thr Ile Ser Arg Asp Asn
                85                  90                  95

Ser Lys Asn Ser Leu Tyr Leu Gln Met Asn Ser Leu Arg Ala Glu Asp
            100                 105                 110

Thr Ala Val Tyr Tyr Cys Ala Arg Pro Gly Ala Gly Arg Leu Asp Tyr
        115                 120                 125

Trp Gly Gln Gly Thr Leu Val Thr Val Ser Ser Gly Gly Gly Gly Ser
    130                 135                 140

Gly Gly Gly Gly Ser Gly Gly Gly Gly Ser Asn Phe Met Leu Thr Gln
145                 150                 155                 160

Asp Ala Ala Val Ser Val Ala Leu Gly Gln Thr Val Arg Ile Thr Cys
                165                 170                 175

Gln Gly Asp Ser Leu Arg Ser Tyr Tyr Ala Ser Trp Tyr Gln Gln Lys
            180                 185                 190

Pro Gly Gln Ala Pro Val Leu Val Val Tyr Gly Lys Asn Asn Arg Pro
        195                 200                 205
```

```
Ser Gly Ile Pro Asp Arg Phe Ser Gly Ser Ser Ser Gly Asn Thr Ala
    210                 215                 220

Ser Leu Thr Ile Thr Gly Ala Gln Ala Glu Asp Glu Ala Asp Tyr Tyr
225                 230                 235                 240

Cys Asn Ser Arg Asp Ser Ser Gly Asn Pro Trp Ala Phe Gly Gly Gly
                245                 250                 255

Thr Lys Val Thr Val Leu Ala Ser Gly Lys Pro Ile Pro Asn Pro Leu
            260                 265                 270

Leu Gly Leu Asp Ser Thr His His His His His His
        275                 280


<210> SEQ ID NO 7
<211> LENGTH: 12
<212> TYPE: PRT
<213> ORGANISM: Artificial
<220> FEATURE:
<223> OTHER INFORMATION: Chemically synthesized

<400> SEQUENCE: 7

Cys Ala Arg Pro Gly Ala Gly Arg Leu Asp Tyr Trp
1               5                   10


<210> SEQ ID NO 8
<211> LENGTH: 13
<212> TYPE: PRT
<213> ORGANISM: Artificial
<220> FEATURE:
<223> OTHER INFORMATION: Chemically synthesized

<400> SEQUENCE: 8

Cys Asn Ser Arg Asp Ser Ser Gly Asn Pro Trp Ala Phe
1               5                   10


<210> SEQ ID NO 9
<211> LENGTH: 522
<212> TYPE: PRT
<213> ORGANISM: Homo sapiens

<400> SEQUENCE: 9

Met Gly Pro Gly Arg Pro Ala Pro Ala Pro Trp Pro Arg His Leu Leu
1               5                   10                  15

Arg Cys Val Leu Leu Leu Gly Cys Leu His Leu Gly Arg Pro Gly Ala
            20                  25                  30

Pro Gly Asp Ala Ala Leu Pro Glu Pro Asn Val Phe Leu Ile Phe Ser
        35                  40                  45

His Gly Leu Gln Gly Cys Leu Glu Ala Gln Gly Gly Gln Val Arg Val
    50                  55                  60

Thr Pro Ala Cys Asn Thr Ser Leu Pro Ala Gln Arg Trp Lys Trp Val
65                  70                  75                  80

Ser Arg Asn Arg Leu Phe Asn Leu Gly Thr Met Gln Cys Leu Gly Thr
                85                  90                  95

Gly Trp Pro Gly Thr Asn Thr Thr Ala Ser Leu Gly Met Tyr Glu Cys
            100                 105                 110

Asp Arg Glu Ala Leu Asn Leu Arg Trp His Cys Arg Thr Leu Gly Asp
        115                 120                 125

Gln Leu Ser Leu Leu Leu Gly Ala Arg Thr Ser Asn Ile Ser Lys Pro
    130                 135                 140

Gly Thr Leu Glu Arg Gly Asp Gln Thr Arg Ser Gly Gln Trp Arg Ile
145                 150                 155                 160
```

-continued

```
Tyr Gly Ser Glu Glu Asp Leu Cys Ala Leu Pro Tyr His Glu Val Tyr
                165                 170                 175

Thr Ile Gln Gly Asn Ser His Gly Lys Pro Cys Thr Ile Pro Phe Lys
            180                 185                 190

Tyr Asp Asn Gln Trp Phe His Gly Cys Thr Ser Thr Gly Arg Glu Asp
        195                 200                 205

Gly His Leu Trp Cys Ala Thr Thr Gln Asp Tyr Gly Lys Asp Glu Arg
    210                 215                 220

Trp Gly Phe Cys Pro Ile Lys Ser Asn Asp Cys Glu Thr Phe Trp Asp
225                 230                 235                 240

Lys Asp Gln Leu Thr Asp Ser Cys Tyr Gln Phe Asn Phe Gln Ser Thr
                245                 250                 255

Leu Ser Trp Arg Glu Ala Trp Ala Ser Cys Glu Gln Gln Gly Ala Asp
            260                 265                 270

Leu Leu Ser Ile Thr Glu Ile His Glu Gln Thr Tyr Ile Asn Gly Leu
        275                 280                 285

Leu Thr Gly Tyr Ser Ser Thr Leu Trp Ile Gly Leu Asn Asp Leu Asp
    290                 295                 300

Thr Ser Gly Gly Trp Gln Trp Ser Asp Asn Ser Pro Leu Lys Tyr Leu
305                 310                 315                 320

Asn Trp Glu Ser Asp Gln Pro Asp Asn Pro Ser Glu Glu Asn Cys Gly
                325                 330                 335

Val Ile Arg Thr Glu Ser Ser Gly Gly Trp Gln Asn Arg Asp Cys Ser
            340                 345                 350

Ile Ala Leu Pro Tyr Val Cys Lys Lys Lys Pro Asn Ala Thr Ala Glu
        355                 360                 365

Pro Thr Pro Pro Asp Arg Trp Ala Asn Val Lys Val Glu Cys Glu Pro
    370                 375                 380

Ser Trp Gln Pro Phe Gln Gly His Cys Tyr Arg Leu Gln Ala Glu Lys
385                 390                 395                 400

Arg Ser Trp Gln Glu Ser Lys Lys Ala Cys Leu Arg Gly Gly Gly Asp
                405                 410                 415

Leu Val Ser Ile His Ser Met Ala Glu Leu Glu Phe Ile Thr Lys Gln
            420                 425                 430

Ile Lys Gln Glu Val Glu Glu Leu Trp Ile Gly Leu Asn Asp Leu Lys
        435                 440                 445

Leu Gln Met Asn Phe Glu Trp Ser Asp Gly Ser Leu Val Ser Phe Thr
    450                 455                 460

His Trp His Pro Phe Glu Pro Asn Asn Phe Arg Asp Ser Leu Glu Asp
465                 470                 475                 480

Cys Val Thr Ile Trp Gly Pro Glu Gly Arg Trp Asn Asp Ser Pro Cys
                485                 490                 495

Asn Gln Ser Leu Pro Ser Ile Cys Lys Lys Ala Gly Gln Leu Ser Gln
            500                 505                 510

Gly Ala Ala Glu Glu Asp His Gly Cys Arg
        515                 520
```

COMPOSITION OF ANTI-ENDO180 ANTIBODIES AND METHODS OF USE FOR THE TREATMENT OF CANCER AND FIBROTIC DISEASES

RELATED APPLICATIONS

This application is a §371 national stage of PCT International Application No. PCT/US2010/028200, filed Mar. 23, 2010, claiming the benefit of U.S. Provisional Patent Application No. 61/162,348, filed Mar. 23, 2009, the contents of each of which are hereby incorporated by reference into this application.

REFERENCE TO SEQUENCE LISTING

This application incorporates-by-reference nucleotide and/or amino acid sequences which are present in the file named "111228_2094_83185_Substitute_Sequence_Listing_GC.txt," which is 35.2 kilobytes in size, and which was created Dec. 28, 2011 in the IBM-PC machine format, having an operating system compatibility with MS-Windows, which is contained in the text file filed Dec. 28, 2011 as part of this application.

FIELD OF THE INVENTION

The present invention relates to molecules that target the ENDO180 polypeptide and are internalized thereby, to conjugates comprising the molecules, to compositions comprising the molecules and conjugates and to methods of using the same for delivery of therapeutic agents to cells that express an ENDO180 polypeptide on the surface of the cell for treating cell proliferative diseases or disorders and fibrosis, and for controlling (modulating) tumor progression.

BACKGROUND OF THE INVENTION

ENDO180 Receptor

ENDO180, also known as CD280, uPARAP (urokinase plasminogen activator receptor associated protein) and mannose receptor C type 2 (MRC2), is a recycling endocytic receptor that directs bound ligands to degradation in the endosomes. It is part of a triple complex with urokinase type plasmin activator (uPA) and urokinase-type plasmin activator receptor (uPAR), thus being involved in the production of plasmin from plasminogen. Plasmin, in turn, is known to play a role in both extracellular matrix (ECM) turnover and proteolytic conversion of latent TGF-beta into its active form.

In addition to its role in the production of plasmin, the triple complex was shown to be involved in the activation of matrix metalloproteinase (MMP) proenzymes, to act on fibrin to bind several collagens and in general turnover of extracellular matrix. This complex also takes part in cell adhesion and signal transduction (Bherendt et al, 2000. JBC 275:1993-2002).

ENDO180 is a recycling endocytic receptor that functions in cell motility and remodeling of the extracellular matrix by promoting cell migration and uptake of collagens for intracellular degradation (Niels. 2004 Biol Chem. 385(2):103-36; Kjoller et al, 2004 Exp Cell Res. 293(1):106-16; Wienke et al., 2007 Cancer Res. 67(21):10230-40). ENDO180 shares homology with the macrophage mannose receptor family: mannose receptor, phosphlipase $A_2$ and DEC-205/MR6 (Isacke et al., 1990 Mol. Cell. Biol. 10:2606-2618; Sheikh et al., 2000, J. Cell. Sci. 113: 1021-1032; Behrendt et al., 2000, J. Biol. Chem. 275: 1993-2002). This family grouping is based on an overall structural conservation: a large extracellular domain comprising an N-terminal signal sequence followed by a cysteine-rich domain, a fibronectin type II domain (FNII), and 8 or 10 C-type lectin-like domains (CTLDs) and small transmembrane and intracellular domains (~66 amino acids together). As a family, these receptors have two striking features: First, although they belong to the large C-type lectin superfamily, they uniquely contain multiple CTLDs within a single polypeptide backbone (Taylor M. E., 1997 Glycobiology 7: v-vii; McKay et al, 1998, Eur. J. Immunol. 28: 4071-4083; Howard and Isacke, 2002, supra). Second, they share the ability to be recycled between the plasma membrane and intercellular compartments of the cell (Isacke et al, 1990, supra; Zvaritch et al., 1996, J. Biol. Chem. 271: 250-257). ENDO180 is unusual in the family of mannose receptors in that it is targeted from the plasma membrane to the recycling endosomes rather than to a late endosome/lysosome compartment (Howard and Isacke, 2002 supra).

ENDO180 is localized on the cell surface, in clathrin coated pits (Isacke et al., 1990 Mol. Cell. Biol. 10: 2606-2618; Sheikh et al., 2000, J. Cell. Sci. 113: 1021-1032) and in endosomes. It is mainly expressed in fibroblasts, endothelial cells and macrophages. In situ hybridization showed its expression in highly vascularized organs. ENDO180 has also been found in bone-forming regions in mouse embryos (Wu et al., 1996, J. Biol. Chem. 271:21323-21330), and in osteoblasts and osteocytes at sites of endochondral and intramembraneous ossification during development (Engelholm et al., 2001, Trends Cardiovasc. Med. 11:7-13.

The following patent publications also relate to the ENDO180 receptor: U.S. Pat. No. 6,117,977; U.S. Pat. No. 7,399,468; WO 97/40154 and WO 00/58473. PCT Patent Publication No. WO 2004/100759 and US Patent Publication Nos. 2007/0072244 and 2009/0202566 to the assignee of the present invention and hereby incorporated by reference in their entirety relate to methods of identifying compounds capable of modulating human ENDO180 receptor activity.

Antibody Therapy

The search for new therapies to treat cancer and other diseases has resulted in the development of human and humanized antibodies capable of inhibiting receptor function. International patent publication WO 2006/023491 provides a method of RNA interference, which comprises contacting the cell with a fusion protein-double stranded RNA complex, the complex comprising the double stranded RNA segment containing a double stranded RNA of interest and a fusion protein which is an antibody Fab fragment-protamine fusion protein.

SUMMARY OF THE INVENTION

The present invention is based in part on the identification of isolated molecules that specifically bind the ENDO180 polypeptide on a cell surface. In some embodiments the molecules bind the extracellular domain of the ENDO180 polypeptide and are internalized into the cell by the polypeptide, thereby providing a vehicle useful for delivery of therapeutic and diagnostic cargo to a cell expressing the ENDO180 polypeptide. Accordingly, in some embodiments the present invention provides a conjugate comprising a molecule that specifically binds the ENDO180 polypeptide and a therapeutic agent useful for the delivery of the therapeutic agent into the cell. In some embodiments the ENDO180 polypeptide is substantially identical to an amino acid sequence set forth in SEQ ID NO:2, encoded by a polynucleotide substantially identical to a nucleic acid sequence set forth in SEQ ID NO:1.

In one aspect the present invention provides an anti-ENDO180 antibody which is produced by hybridoma cell line designated E3-8D8 (BCCM Accession Number LMBP 7203CB), or a fragment of the antibody, which binds to ENDO180 receptor on the surface of a cell. In some embodiments binding of the antibody to the receptor results in internalization of the antibody into the cell. Also provided is the E3-8D8 hybridoma cell line.

In some embodiments the antibody or fragment thereof is humanized or a chimeric antibody or fragment thereof.

The invention provides a composition comprising at least one anti-ENDO180 antibody or fragment thereof, the antibody produced by the E3-8D8 hybridoma or a humanized molecule thereof a chimeric antibody or fragment thereof, together with a carrier.

In some embodiments the isolated antibody is selected from the group consisting of a full IgG, a Fab fragment, a Fab' fragment, an F(ab')2 fragment, the variable portion of the heavy and/or light chains thereof, Fab miniantibodies, and a scFv. In some embodiments the antibody is a recombinant polypeptide comprising a heavy chain CDR3 domain having an amino acid sequence set forth in SEQ ID NO:7 or a variant thereof which retains the ability to specifically bind ENDO180. In some embodiments the antibody further comprises a light chain CDR3 domain having an amino acid sequence set forth in SEQ ID NO:8 or a variant thereof which retains the ability to specifically bind ENDO180.

In some embodiments the antibody is a scFv recombinant polypeptide comprising an amino acid sequence set forth in SEQ ID NO:6 or a variant thereof, which retains the ability to specifically bind ENDO180. In specific embodiments the antibody exhibiting binding affinity to ENDO180 receptor and comprising CDR3 domains set forth in SEQ ID NOS 7 and 8 is internalized by the receptor into the cell expressing ENDO180 upon contact of the antibody to the receptor.

The invention further provides a composition comprising at least one anti-ENDO180 antibody or fragment thereof, as described above, and a moiety including a radioisotope, a therapeutic agent, a cytotoxic agent, or a detectable label. In some embodiments the moiety is attached (or linked, or conjugated), either covalently, through a linker or a chemical bond, or noncovalently, through ionic, van der Waals, electrostatic, or hydrogen bonds, to the antibody.

In some embodiments provided is an anti-ENDO180 antibody or antigen-binding fragment thereof selected from a) the monoclonal antibody produced by the hybridoma cell line E3-8D8 (BCCM Accession Number LMBP 7203CB);
b) an antibody or fragment thereof that binds to the same epitope as the antibody in (a);
c) a humanized antibody of (a) or (b);
d) a fragment of an antibody comprising a polypeptide substantially similar to SEQ ID NO: 6; and
e) a recombinant polypeptide comprising CDR3 with an amino acid sequence substantially similar to amino acid sequences set forth in SEQ ID NO:7 and 8.

Further provided is a composition comprising an anti-ENDO180 antibody or antigen-binding fragment thereof selected from a) the monoclonal antibody produced by the hybridoma cell line E3-8D8 (BCCM Accession Number LMBP 7203CB);
b) an antibody or fragment thereof that binds to the same epitope as the antibody in (a);
c) a humanized antibody of (a) or (b);
d) a fragment of an antibody comprising a polypeptide substantially similar to SEQ ID NO: 6; and
e) a recombinant polypeptide comprising CDRs having an amino acid sequence substantially similar to amino acid sequences set forth in SEQ ID NO:7 and 8.

In some embodiments the composition further comprises a moiety including a radioisotope, a therapeutic agent, a cytotoxic agent, or a detectable label.

The present invention also provides a method of treating a subject afflicted with a proliferative disorder comprising administering to the subject a composition comprising an anti-ENDO180 antibody or antigen-binding fragment thereof selected from a) the monoclonal antibody produced by the hybridoma cell line E3-8D8 (BCCM Accession Number LMBP 7203CB);
b) an antibody or fragment thereof that binds to the same epitope as the antibody in (a);
c) a humanized antibody of (a) or (b);
d) a fragment of an antibody comprising a polypeptide substantially similar to SEQ ID NO: 6; and
e) a recombinant polypeptide comprising CDRs having an amino acid sequence substantially similar to amino acid sequences set forth in SEQ ID NO:7 and 8.

In some embodiments the proliferative disorder is selected from a solid tumor, a hematopoietic tumor, metastases, fibrosis and a macrophage associated disorder.

In some embodiments the tumor is an ovarian tumor, a breast tumor, osteoblastic/osteocytic cancer, prostate cancer, head and neck cancer, leukemia, renal cell carcinoma, or transitional cell carcinoma.

In some embodiments the fibrosis is liver fibrosis, myelofibrosis, kidney fibrosis for any reason (CKD including end-stage renal disease, ESRD); lung fibrosis (including interstitial lung fibrosis ILF); abnormal scarring (keloids) associated with all possible types of skin injury accidental and jatrogenic (operations); scleroderma; cardiofibrosis, failure of glaucoma filtering operation; intestinal adhesions.

In some embodiments the macrophage-associated disorder is inflammation or atherosclerosis.

In one aspect the present invention provides a conjugate comprising:

a) an antibody or an antigen binding portion thereof which specifically binds to the extracellular domain of the ENDO180 polypeptide on the surface of a cell;
b) a moiety including a radioisotope, a therapeutic agent, a cytotoxic agent, or a detectable label; and
c) optionally a linking moiety which links (a) to (b).

In some embodiments the moiety is a therapeutic agent selected from an oligonucleotide agent and a non-oligonucleotide agent. In some embodiments the therapeutic agent is an oligonucleotide therapeutic agent, including an inhibitory oligonucleotide. Accordingly, in various embodiments the therapeutic agent is selected from an antisense compound, a chemically modified siRNA compound, an unmodified siRNA compound, a chemically modified shRNA compound, an unmodified shRNA compound, a chemically modified miRNA compound, and an unmodified miRNA compound. In various preferred embodiments the therapeutic agent is chemically modified siRNA. In some embodiments the chemically modified siRNA compound inhibits expression of a target gene associated with cancer, fibrosis or macrophage associated disease. In some embodiments the target gene is selected from any one of the target genes set forth in Table A, hereinbelow.

In certain embodiments the therapeutic agent is attached to the antibody via a nucleotide or non-nucleotide linking moiety.

In yet another aspect the present invention provides a pharmaceutical composition comprising the conjugate of the present invention.

In yet another aspect the present invention provides a method of treating a subject suffering from a proliferative disease comprising administering to the subject a therapeutically effective amount of an antibody that specifically binds ENDO180 polypeptide and is internalized by the ENDO180 polypeptide, wherein the antibody is covalently or non-covalently bound to a therapeutic agent.

In some embodiments the proliferative disease is selected from malignant and benign proliferative disease. In some embodiments proliferative disease is cancer. In other embodiments proliferative disease is fibrosis. Non-limiting examples of diseases and disorders for use of the present invention include 1. soft tissue sarcomas in which ENDO180 is expressed in the tumor and tumor stroma cells (activated myofibroblasts, neovasculature and infiltrating cells of macrophage-monocyte lineage);
2. carcinomas in which ENDO180 is expressed in the tumor stroma cells (activated myofibroblasts, neovasculature and infiltrating cells of macrophage-monocyte lineage);
3. carcinoma that express ENDO180 and have undergone epithelial-mesenchymal transition thus acquiring high metastatic potential;
4. leukemia expressing ENDO180 for example, from macrophage-monocyte lineage;
5. fibrotic diseases, for example of kidney, lung and liver with activated myofibroblasts;
6. diseases and disorders associated with macrophage including atherosclerosis and chronic inflammation.

BRIEF DESCRIPTION OF THE FIGURES

FIG. 1A-1J provides polynucleotide and amino acid sequences of various compounds according to the present invention. FIG. 1A: human ENDO180 mRNA (SEQ ID NO:1);

FIG. 1B: human ENDO180 polypeptide (SEQ ID NO:2); FIG. 1C: SEQ ID NO:3 polynucleotide sequence of extracellular domain of human ENDO180 (amino acids 1-522) with FLAG sequence, FLAG domain underlined (pcDNA3-5' hendo180-FLAG construct, SEQ ID NO:3); FIG. 1D polypeptide sequence of SEQ ID NO:3 (SEQ ID NO:4); FIG. 1E: polynucleotide sequence of scFv clone G7V (SEQ ID NO:5); FIG. 1F: polypeptide sequence of scFv clone G7V (SEQ ID NO:6); FIG. 1G. heavy chain CDR3 of G7V (SEQ ID NO:7); FIG. 1H. light chain CDR3 of G7V (SEQ ID NO:8); FIG. 1J: polypeptide 1-522 of the extracellular domain of human ENDO180.

FIG. 3. Internalization of Biotin anti-ENDO180 mAbs to mice having Unilateral Ureter Obstructed kidney.

FIG. 4. Internalization of anti-ENDO180 mAbs conjugated to CypHer5E fluorophore into Myelo-Monocytoid human leukemia MonoMac cell line expressing ENDO180.

DETAILED DESCRIPTION OF THE INVENTION

Definitions

Figure 2A:
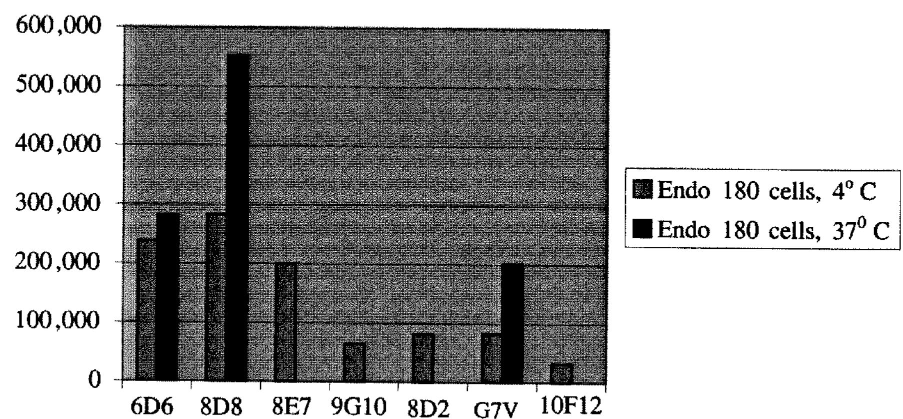
FIGS. 2A-2H. Internalization of CypHer5E fluorophore anti-ENDO180 mAbs to ENDO180 expressing cells.

For convenience certain terms employed in the specification, examples and claims are described herein.

It is to be noted that, as used herein, the singular forms "a", "an" and "the" include plural forms unless the content clearly dictates otherwise.

Where aspects or embodiments of the invention are described in terms of Markush groups or other grouping of alternatives, those skilled in the art will recognize that the invention is also thereby described in terms of any individual member or subgroup of members of the group.

An "inhibitor" is a compound, which is capable of reducing (partially or fully) the expression of a gene or the activity of the product of such gene to an extent sufficient to achieve a desired biological or physiological effect. The term "inhibitor" as used herein includes one or more of an oligonucleotide inhibitor, including siRNA, shRNA, synthetic shRNA; miRNA, antisense RNA and DNA and ribozymes. An "inhibitory oligonucleotide" includes an antisense compound, a chemically modified siRNA compound, an unmodified siRNA compound, a chemically modified shRNA compound, an unmodified shRNA compound, a chemically modified miRNA compound, and an unmodified miRNA compound.

A "siRNA inhibitor" is a compound which is capable of reducing the expression of a gene or the activity of the product of such gene to an extent sufficient to achieve a desired biological or physiological effect. The term "siRNA inhibitor" as used herein refers to one or more of a siRNA, shRNA, synthetic shRNA; miRNA. Inhibition may also be referred to as down-regulation or, for RNAi, silencing.

The term "inhibit" as used herein refers to reducing the expression of a gene or the activity of the product of such gene to an extent sufficient to achieve a desired biological or physiological effect. Inhibition may be complete or partial. As used herein, the term "ENDO180 gene" is defined as any homolog of the ENDO180 gene having preferably 90% homology, more preferably 95% homology, and even more preferably 98% homology to the amino acid encoding region of SEQ ID NO:1 or nucleic acid sequences which bind to the ENDO180 gene under conditions of highly stringent hybridization, which are well-known in the art (for example, see Ausubel et al., Current Protocols in Molecular Biology, John Wiley and Sons, Baltimore, Md. (1988), updated in 1995 and 1998).

As used herein, the term "ENDO180" or "ENDO180 polypeptide" or "ENDO180 receptor" is defined as any homolog of the ENDO180 polypeptide having preferably at least 90% homology, more preferably at least 95% homology, and even more preferably at least 98% homology or 100% identity to SEQ ID NO:2, as either full-length or a fragments or a domain thereof, as a mutant or the polypeptide encoded by a spliced variant nucleic acid sequence, as a chimera with other polypeptides, provided that any of the above has the same or substantially the same biological function as the ENDO180 receptor. ENDO180 polypeptide, or an ENDO180 polypeptide homolog, may be present in different forms, including but not limited to soluble protein, membrane-bound (either in purified membrane preparations or on a cell surface), bead-bound, or any other form presenting ENDO180 protein or fragments and polypeptides derived thereof. The term "inhibit" as used herein refers to reducing the expression of a gene or the activity of the product of such gene to an extent sufficient to achieve a desired biological or physiological effect. Inhibition is either complete or partial.

The terms "mRNA polynucleotide sequence", "mRNA sequence" and "mRNA" are used interchangeably.

As used herein, the terms "polynucleotide" and "nucleic acid" may be used interchangeably and refer to nucleotide sequences comprising deoxyribonucleic acid (DNA), and ribonucleic acid (RNA). The terms are to be understood to include, as equivalents, analogs of either RNA or DNA made from nucleotide analogs. Throughout this application, mRNA sequences are set forth as representing the corresponding genes.

"Oligonucleotide" or "oligomer" refers to a deoxyribonucleotide or ribonucleotide sequence from about 2 to about 50 nucleotides. Each DNA or RNA nucleotide may be independently natural or synthetic, and or modified or unmodified. Modifications include changes to the sugar moiety, the base moiety and or the linkages between nucleotides in the oligonucleotide. The compounds of the present invention encompass molecules comprising deoxyribonucleotides, ribonucleotides, modified deoxyribonucleotides, modified ribonucleotides and combinations thereof.

Substantially complementary refers to complementarity of greater than about 84%, to another sequence. For example in a duplex region consisting of 19 base pairs one mismatch results in 94.7% complementarity, two mismatches results in about 89.5% complementarity and 3 mismatches results in about 84.2% complementarity, rendering the duplex region substantially complementary. Accordingly substantially identical refers to identity of greater than about 84%, to another sequence.

The conjugate of the present invention comprises a) an antibody or fragment thereof, which specifically binds to an ENDO180 polypeptide on the surface of a cell, b) a nucleotide-based therapeutic agent selected from an antisense compound, a chemically modified siRNA compound, an unmodified siRNA compound, a chemically modified shRNA compound, an unmodified shRNA compound, a chemically modified miRNA compound, and an unmodified miRNA compound; and c) a linking moiety which links (a) to (b); wherein the nucleotide-based therapeutic agent inhibits expression of the target gene in the cell.

The "linker" according to the present invention is a nucleotide or non-nucleotide moiety which links the antibody to the therapeutic molecule. In some embodiments the linker is a cleavable moiety. Preferred cleavable groups include a disulfide bond, amide bond, thioamide, bond, ester bond, thioester bond, vicinal diol bond, or hemiacetal. Other cleavable bonds include enzymatically-cleavable bonds, such as peptide bonds (cleaved by peptidases), phosphate bonds (cleaved by phosphatases), nucleic acid bonds (cleaved by endonucleases), and sugar bonds (cleaved by glycosidases).

In some embodiments the linker is a non-nucleotide linker including a peptide linker. The choice of peptide sequence is critical to the success of the conjugate. In some embodiments the linker is stable to serum proteases, yet is cleaved by the lysosomal enzymes in the target cell. In a non-limiting example the linker is a peptide selected from a linker set forth in U.S. Pat. No. 5,574,142, protamine, a fragment of protamine, (Arg)9, biotin-avidin, biotin-streptavidin and antennapedia peptide. For example, a peptide linker is used to link the antibody to a nucleotide therapeutic agent. Other non-nucleotide linkers include alkyl or aryl chains of about 5 to about 100 atoms.

In some embodiments the linker is a nucleotide linker. In certain embodiments a nucleic acid linker has a length ranging from 2-100, preferably 2-50 or 2-30 nucleotides.

Oligonucleotide Chemical Modifications

"Nucleotide" is meant to encompass deoxyribonucleotides and ribonucleotides, which may be natural or synthetic, and or modified or unmodified. Modifications include changes to the sugar moiety, the base moiety and or the linkages between ribonucleotides in the oligoribonucleotide. As used herein, the term "ribonucleotide" encompasses natural and synthetic, unmodified and modified ribonucleotides. Modifications include changes to the sugar moiety, to the base moiety and/or to the linkages between ribonucleotides in the oligonucleotide.

The nucleotides useful in preparing a therapeutic agent include naturally occurring or synthetic modified bases. Naturally occurring bases include adenine, guanine, cytosine, thymine and uracil. Modified bases of nucleotides include inosine, xanthine, hypoxanthine, 2-aminoadenine, 6-methyl, 2-propyl and other alkyl adenines, 5-halo uracil, 5-halo cytosine, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other aza and deaza adenines, other aza and deaza guanines, 5-trifluoromethyl uracil and 5-trifluoro cytosine. In some embodiments one or more nucleotides in an oligomer is substituted with inosine.

According to some embodiments the present invention provides inhibitory oligonucleotide compounds comprising unmodified and modified nucleotides and or unconventional moieties. In certain embodiments the therapeutic agent is an oligonucleotide. In various preferred embodiments the therapeutic agent is a double stranded oligonucleotide and preferably siRNA.

The selection and synthesis of siRNA corresponding to known genes has been widely reported; (see for example Ui-Tei et al., 2006. J Biomed Biotechnol.; 2006:65052; Chalk et al., 2004. BBRC. 319(1): 264-74; Sioud & Leirdal, 2004. Met. Mol. Biol.; 252:457-69; Levenkova et al., 2004, Bioinform. 20(3):430-2; Ui-Tei et al., 2004. NAR 32(3):936-48).

For examples of the use of, and production of, modified siRNA see for example Braasch et al., 2003. Biochem., 42(26):7967-75; Chiu et al., 2003, RNA, 9(9):1034-48; PCT publications WO 2004/015107 (atugen AG) and WO 02/44321 (Tuschl et al). U.S. Pat. Nos. 5,898,031 and 6,107,094 teach chemically modified oligomers. U.S. Pat. No. 7,452,987 relates to oligomeric compounds having alternating unmodified and 2' sugar modified ribonucleotides. US patent publication No. 2005/0042647 describes dsRNA compounds having chemically modified internucleotide linkages.

Amarzguoui et al., (2003, NAR, 31(2):589-595) showed that siRNA activity depended on the positioning of the 2'-O-methyl modifications. Holen et al (2003, NAR, 31(9):2401-2407) report that an siRNA having small numbers of 2'-O-methyl modified nucleosides showed good activity compared to wild type but that the activity decreased as the numbers of 2'-O-methyl modified nucleosides was increased. Chiu and Rana (2003, RNA, 9:1034-1048) teach that incorporation of 2'-O-methyl modified nucleosides in the sense or antisense strand (fully modified strands) severely reduced siRNA activity relative to unmodified siRNA. The placement of a 2'-O-methyl group at the 5'-terminus on the antisense strand was reported to severely limit activity whereas placement at the 3'-terminus of the antisense and at both termini of the sense strand was tolerated (Czauderna et al., 2003, NAR, 31(11), 2705-2716).

PCT Patent Application Nos. PCT/IL2008/000248 and PCT/IL2008/001197, assigned to the assignee of the present invention and hereby incorporated by reference in their entirety disclose motifs useful in the preparation of chemically modified siRNA compounds. PCT Patent Publication No. WO 2008/020435 discloses inhibitors, including some siRNA compounds to the target genes set forth herein.

The compound comprises at least one modified nucleotide selected from the group consisting of a sugar modification, a base modification and an internucleotide linkage modification and may contain DNA, and modified nucleotides such as LNA (locked nucleic acid), ENA (ethylene-bridged nucleic acid), PNA (peptide nucleic acid), arabinoside, phosphonocarboxylate or phosphinocarboxylate nucleotide (PACE nucleotide), mirror nucleotide, or nucleotides with a 6 carbon sugar.

All analogs of, or modifications to, a nucleotide/oligonucleotide are employed with the present invention, provided that said analog or modification does not substantially adversely affect the function of the nucleotide/oligonucleotide. Acceptable modifications include modifications of the sugar moiety, modifications of the base moiety, modifications in the internucleotide linkages and combinations thereof.

A sugar modification includes a modification on the 2' moiety of the sugar residue and encompasses amino, fluoro, alkoxy e.g. methoxy, alkyl, amino, fluoro, chloro, bromo, CN, CF, imidazole, carboxylate, thioate, $C_1$ to $C_{10}$ lower alkyl, substituted lower alkyl, alkaryl or aralkyl, $OCF_3$, OCN, O—, S—, or N-alkyl; O-, S, or N-alkenyl; $SOCH_3$; $SO_2CH_3$; $ONO_2$; $NO_2$, $N_3$; heterozycloalkyl; heterozycloalkaryl; aminoalkylamino; polyalkylamino or substituted silyl, as, among others, described in European patents EP 0 586 520 B1 or EP 0 618 925 B1.

In one embodiment the siRNA compound comprises at least one ribonucleotide comprising a 2' modification on the sugar moiety ("2' sugar modification"). In certain embodiments the compound comprises 2'O-alkyl or 2'-fluoro or 2'O-allyl or any other 2' modification, optionally on alternate positions. Other stabilizing modifications are also possible (e.g. terminal modifications). In some embodiments a preferred 2'O-alkyl is 2'O-methyl(methoxy) sugar modification.

In some embodiments the backbone of the oligonucleotides is modified and comprises phosphate-D-ribose entities but may also contain thiophosphate-D-ribose entities, triester, thioate, 2'-5' bridged backbone (also may be referred to as 5'-2'), PACE and the like.

As used herein, the terms "non-pairing nucleotide analog" means a nucleotide analog which comprises a non-base pairing moiety including but not limited to: 6 des amino adenosine (Nebularine), 4-Me-indole, 3-nitropyrrole, 5-nitroindole, Ds, Pa, N3-Me ribo U, N3-Me riboT, N3-Me dC, N3-Me-dT, N1-Me-dG, N1-Me-dA, N3-ethyl-dC, N3-Me dC. In some embodiments the non-base pairing nucleotide analog is a ribonucleotide. In other embodiments it is a deoxyribonucleotide. In addition, analogs of polynucleotides may be prepared wherein the structure of one or more nucleotide is fundamentally altered and better suited as therapeutic or experimental reagents. An example of a nucleotide analog is a peptide nucleic acid (PNA) wherein the deoxyribose (or ribose) phosphate backbone in DNA (or RNA is replaced with a polyamide backbone which is similar to that found in peptides. PNA analogs have been shown to be resistant to enzymatic degradation and to have extended stability in vivo and in vitro. Other modifications that can be made to oligonucleotides include polymer backbones, cyclic backbones, acyclic backbones, thiophosphate-D-ribose backbones, triester backbones, thioate backbones, 2'-5' bridged backbone, artificial nucleic acids, morpholino nucleic acids, glycol nucleic acid (GNA), threose nucleic acid (TNA), arabinoside, and mirror nucleoside (for example, beta-L-deoxyribonucleoside instead of beta-D-deoxyribonucleoside). Examples of siRNA compounds comprising LNA nucleotides are disclosed in Elmen et al., (NAR 2005, 33(1):439-447).

The compounds of the present invention can be synthesized using one or more inverted nucleotides, for example inverted thymidine or inverted adenine (see, for example, Takei, et al., 2002, JBC 277(26):23800-06).

Other modifications include terminal modifications on the 5' and/or 3' part of the oligonucleotides and are also known as capping moieties. Such terminal modifications are selected from a nucleotide, a modified nucleotide, a lipid, a peptide, a sugar and inverted abasic moiety.

What is sometimes referred to in the present invention as an "abasic nucleotide" or "abasic nucleotide analog" is more properly referred to as a pseudo-nucleotide or an unconventional moiety. A nucleotide is a monomeric unit of nucleic acid, consisting of a ribose or deoxyribose sugar, a phosphate, and a base (adenine, guanine, thymine, or cytosine in DNA; adenine, guanine, uracil, or cytosine in RNA). A modified nucleotide comprises a modification in one or more of the sugar, phosphate and or base. The abasic pseudo-nucleotide lacks a base, and thus is not strictly a nucleotide.

In some embodiments the siRNA therapeutic agent comprises a capping moiety. The term "capping moiety" as used herein includes abasic ribose moiety, abasic deoxyribose moiety, modifications abasic ribose and abasic deoxyribose moieties including 2' O alkyl modifications; inverted abasic ribose and abasic deoxyribose moieties and modifications thereof; C6-imino-Pi; a mirror nucleotide including L-DNA and L-RNA; 5'O-Me nucleotide; and nucleotide analogs including 4',5'-methylene nucleotide; 1-(β-D-erythrofuranosyl)nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; alpha-nucleotide; threo-pentofuranosyl nucleotide; acyclic 3',4'-seco nucleotide; 3,4-dihydroxybutyl nucleotide; 3,5-dihydroxypentyl nucleotide, 5'-5'-inverted abasic moiety; 1,4-butanediol phosphate; 5'-amino; and bridging or non bridging methylphosphonate and 5'-mercapto moieties.

Certain preferred capping moieties are abasic ribose or abasic deoxyribose moieties; inverted abasic ribose or abasic deoxyribose moieties; C6-amino-Pi; a mirror nucleotide including L-DNA and L-RNA.

In some embodiments the therapeutic siRNA comprises a moiety other than a nucleotide. The term "unconventional moiety" as used herein refers to abasic ribose moiety, an abasic deoxyribose moiety, a deoxyribonucleotide, a modified deoxyribonucleotide, a mirror nucleotide, a non-base pairing nucleotide analog and a nucleotide joined to an adjacent nucleotide by a 2'-5' internucleotide phosphate bond; bridged nucleic acids including LNA and ethylene bridged nucleic acids.

Abasic deoxyribose moiety includes for example abasic deoxyribose-3'-phosphate; 1,2-dideoxy-D-ribofuranose-3-phosphate; 1,4-anhydro-2-deoxy-D-ribitol-3-phosphate. Inverted abasic deoxyribose moiety includes inverted deoxyriboabasic; 3',5' inverted deoxyabasic 5'-phosphate.

A "mirror" nucleotide is a nucleotide with reversed chirality to the naturally occurring or commonly employed nucleotide, i.e., a mirror image (L-nucleotide) of the naturally occurring (D-nucleotide), also referred to as L-RNA in the case of a mirror ribonucleotide, and "spiegelmer". The nucleotide can be a ribonucleotide or a deoxyribonucleotide and my further comprise at least one sugar, base and or backbone modification. See U.S. Pat. No. 6,586,238. Also, U.S. Pat. No. 6,602,858 discloses nucleic acid catalysts comprising at least one L-nucleotide substitution. Mirror nucleotide includes for example L-DNA (L-deoxyriboadenosine-3'-phosphate (mirror dA); L-deoxyribocytidine-3'-phosphate (mirror dC); L-deoxyriboguanosine-3'-phosphate (mirror dG); L-deoxyribothymidine-3'-phosphate (mirror image dT)) and L-RNA (L-riboadenosine-3'-phosphate (mirror rA); L-ribocytidine-3'-phosphate (mirror rC); L-riboguanosine-3'-phosphate (mirror rG); L-ribouracil-3'-phosphate (mirror dU).

Modified deoxyribonucleotide includes, for example 5' OMe DNA (5-methyl-deoxyriboguanosine-3'-phosphate) which may be useful as a nucleotide in the 5' terminal position (position number 1); PACE (deoxyriboadenine 3' phosphonoacetate, deoxyribocytidine 3' phosphonoacetate, deoxyriboguanosine 3' phosphonoacetate, deoxyribothymidine 3' phosphonoacetate.

Bridged nucleic acids include LNA (2'-0,4'-C-methylene bridged Nucleic Acid adenosine 3' monophosphate, 2'-0,4'-C-methylene bridged Nucleic Acid 5-methyl-cytidine 3' monophosphate, 2'-0,4'-C-methylene bridged Nucleic Acid guanosine 3' monophosphate, 5-methyl-uridine (or thymidine) 3' monophosphate); and ENA (2'-0,4'-C-ethylene bridged Nucleic Acid adenosine 3' monophosphate, 2'-0,4'-C-ethylene bridged Nucleic Acid 5-methyl-cytidine 3' monophosphate, 2'-0,4'-C-ethylene bridged Nucleic Acid guanosine 3' monophosphate, 5-methyl-uridine (or thymidine) 3' monophosphate).

In some embodiments of the present invention a preferred unconventional moiety is an abasic ribose moiety, an abasic deoxyribose moiety, a deoxyribonucleotide, a mirror nucleotide, and a nucleotide joined to an adjacent nucleotide by a 2'-5' internucleotide phosphate bond.

According to one aspect the present invention provides inhibitory oligonucleotide compounds comprising unmodified and modified nucleotides. The compound comprises at least one modified nucleotide selected from the group consisting of a sugar modification, a base modification and an internucleotide linkage modification and may contain DNA, and modified nucleotides such as LNA (locked nucleic acid) including ENA (ethylene-bridged nucleic acid; PNA (peptide nucleic acid); arabinoside; PACE (phosphonoacetate and derivatives thereof), mirror nucleotide, or nucleotides with a six-carbon sugar. In some embodiments the present invention provides methods and compositions for inhibiting expression of a target gene in vivo. In general, the method includes administering a delivery-therapeutic agent conjugate. In particular embodiments small interfering RNAs (i.e. siRNAs), that target an mRNA transcribed from the target gene in an amount sufficient to down-regulate expression (reduce mRNA, reduce protein levels) of a target gene by an RNA interference mechanism. In particular, the subject method can be used to inhibit expression of the target gene for treatment of a disease. In accordance with the present invention, the siRNA molecules or inhibitors of the target gene are used as drugs to treat various pathologies.

The synthesis of the nucleic acids described herein, is within the skills of the one of the art. Such synthesis is, among others, described in Beaucage S L and Iyer R P, 1992 Tetrahedron; 48: 2223-2311, Beaucage S, and Iyer R P, 1993 Tetrahedron; 49: 6123-6194 and Caruthers M H et. al., 1987 Methods Enzymol.; 154: 287-313, the synthesis of thioates is, among others, described in Eckstein F., 1985 Annu Rev. Biochem.; 54: 367-402, the synthesis of RNA molecules is described in Sproat B., in Humana Press 2005 Edited by Herdewijn P.; Kap. 2: 17-31 and respective downstream processes are, among others, described in Pingoud A. et. al., in IRL Press 1989 Edited by Oliver R. W. A.; Kap. 7: 183-208 and Sproat B., in Humana Press 2005 Edited by Herdewijn P.; Kap. 2: 17-31 (supra). siRNA for any one of the target genes is synthesized using methods known in the art as described above, based on the known sequence of the target gene mRNA and is stabilized to serum and/or cellular nucleases by various modifications as described herein.

Target Genes

The conjugates according to the present invention are useful for inhibiting expression of a gene associated with a disease or disorder selected from a proliferative disease a metastatic disease and fibrosis.

Target genes include anti-apoptotic genes, genes associated with basic cell division machinery, genes associated with cell cycle regulation/cell proliferation, genes associated with rate-limiting metabolism (nucleotide/nucleic acid synthesis, protein synthesis, energy metabolism), genes associated with protein trafficking (e.g., secretion); proinflammatory genes, cytokines, chemokines, NFkB, growth factors/receptors (TGFβ1 and 2, CTGF, IGF1, PDGF1, PDGF2, VEGF, EGFR, HER2, etc).

A non-limiting list of target genes is set forth in Table A, hereinbelow.

| Abbreviation | full name |
|---|---|
| AARSD1 | alanyl-tRNA synthetase domain containing 1 |
| ABCF1 | ATP-binding cassette, sub-family F (GCN20), member 1 |
| AKT1 | v-akt murine thymoma viral oncogene homolog 1 |
| AKT2 | -akt murine thymoma viral oncogene homolog 2 |
| AKT3 | v-akt murine thymoma viral oncogene homolog 3 (protein kinase B, |
| ANG | angiogenin, ribonuclease, RNase A family, 5 |
| BAD | BCL2-associated agonist of cell death |
| BAG1 | BCL2-associated athanogene |
| BAK1 | BCL2-antagonist/killer 1 |
| BAX | BCL2-associated X protein |
| BCL2 | B-cell CLL/lymphoma 2 |
| BCL2A1 | BCL2-related protein A1 |
| BCL2L1 | BCL2-like 1 |
| BCL2L11 | BCL2-like 11 (apoptosis facilitator) |
| BID | BH3 interacting domain death agonist |
| CALR | calreticulin |
| CASP3 | caspase 3, apoptosis-related cysteine peptidase |
| CASP9 | caspase 9, apoptosis-related cysteine peptidase |
| CASP9 | caspase 9, apoptosis-related cysteine peptidase |
| CCNB1 | cyclin B1 |
| CD40 | CD40 molecule, TNF receptor superfamily member 5 |
| CDC2 | cell division cycle 2, G1 to S and G2 to M |
| CDC73 | cell division cycle 73, Paf1/RNA polymerase II complex component, |
| CDH1 | cadherin 1, type 1, E-cadherin (epithelial) |
| CEBPB | CCAAT/enhancer binding protein (C/EBP), beta |
| CFLAR | CASP8 and FADD-like apoptosis regulator |
| CHEK1 | CHK1 checkpoint homolog (S. pombe) |
| CMPK1 | cytidine monophosphate (UMP-CMP) kinase 1, cytosolic |
| COL4A1 | collagen, type IV, alpha 1 |
| CTGF | connective tissue growth factor |
| DDIT4 | DNA-damage-inducible transcript 4 |
| DDIT4L | DNA-damage-inducible transcript 4 like |
| EEF2K | eukaryotic elongation factor-2 kinase |
| EGF | epidermal growth factor |
| EIF2AK4 | eukaryotic translation initiation factor 2 alpha kinase 4 |
| EPRS | glutamyl-prolyl-tRNA synthetase |
| ERBB2 | -erb-b2 erythroblastic leukemia viral oncogene homolog 2, |
| ERBB3 | v-erb-b2 erythroblastic leukemia viral oncogene homolog 3 |
| ESR1 | estrogen receptor 1 |
| F3 | coagulation factor III |
| FAS | Fas (TNF receptor superfamily, member 6) |
| FEN1 | flap structure-specific endonuclease 1 |
| GAPDH | glyceraldehyde-3-phosphate dehydrogenase |
| H19 | H19, imprinted maternally expressed transcript |
| HDAC1 | histone deacetylase 1 |
| HGF | hepatocyte growth factor (hepapoietin A; scatter factor) |
| HIF1A | hypoxia inducible factor 1, alpha subunit |
| HSF1 | heat shock transcription factor 1 |
| IER3 | immediate early response 3 |
| IGF1 | insulin-like growth factor 1 (somatomedin C) |
| IGF1R | insulin-like growth factor 1 receptor |
| IGFBP5 | insulin-like growth factor binding protein 5 |
| IL15 | interleukin 15 |
| IL8 | interleukin 8 |
| JUN | jun oncogene |

-continued

| Abbreviation | full name |
|---|---|
| MADD | MAP-kinase activating death domain |
| MAPK1 | mitogen-activated protein kinase 1 |
| MCL1 | myeloid cell leukemia |
| MDM2 | Mdm2 p53 binding protein homolog (mouse) |
| MIF | macrophage migration inhibitory factor (glycosylation-inhibiting) |
| MMP3 | matrix metallopeptidase 3 (stromelysin 1, progelatinase) |
| MYC | v-myc myelocytomatosis viral oncogene homolog (avian) |
| c-MYC | myelocytomatosis viral oncogene homolog (avian) |
| NFKB1 | nuclear factor of kappa light polypeptide gene enhancer in B-cells 1 |
| NOS2 | nitric oxide synthase 2, inducible |
| NOTCH1 | Notch homolog 1, translocation-associated (Drosophila) |
| NOX1 | NADPH oxidase 1 |
| NOX2 | cytochrome b-245, beta polypeptide (CYBB) |
| NOX3 | NADPH oxidase 3 |
| NOX4 | NADPH oxidase 4 |
| NOX5 | NADPH oxidase 5 |
| NOXA1 | NADPH oxidase activator 1 |
| NOXO1 | NADPH oxidase organizer 1 |
| NRF2 | nuclear factor (erythroid-derived 2)-like 2 |
| NR4A1 | nuclear receptor subfamily 4, group A, member 1 |
| OAS1 | 2',5'-oligoadenylate synthetase 1, 40/46 kDa |
| OAS2 | 2'-5'-oligoadenylate synthetase 2, 69/71 kDa |
| OAS3 | 2'-5'-oligoadenylate synthetase 3, 100 kDa |
| ODC1 | ornithine decarboxylase 1 |
| PARP1 | poly (ADP-ribose) polymerase 1 |
| PCNA | proliferating cell nuclear antigen |
| PDGFA | platelet-derived growth factor alpha polypeptide |
| PIK3R1 | phosphoinositide-3-kinase, regulatory subunit 1 |
| PLAU | plasminogen activator, urokinase |
| PLK1 | polo-like kinase 1 |
| POLA1 | polymerase (DNA directed), alpha 1, catalytic subunit |
| POLD1 | polymerase (DNA directed), delta 1, catalytic subunit 125 kDa |
| POLE | polymerase (DNA directed), epsilon |
| PPARD | peroxisome proliferator-activated receptor delta |
| PRKAR1A | protein kinase, cAMP-dependent, regulatory, type I, alpha (tissue |
| PRKDC | protein kinase, DNA-activated, catalytic polypeptide |
| PROK2 | prokineticin 2 |
| PTK2 | PTK2 protein tyrosine kinase 2 |
| PTK2B | PTK2B protein tyrosine kinase 2 beta |
| RAC1 | ras-related C3 botulinum toxin substrate 1 (rho family, small GTP |
| RASSF1 | Ras association (RalGDS/AF-6) domain family member 1 |
| REG1A | regenerating islet-derived 1 alpha |
| RFC3 | replication factor C (activator 1) 3, 38 kDa |
| RHOA | ras homolog gene family, member A |
| RPA1 | replication protein A1, 70 kDa |
| SIPA1 | signal-induced proliferation-associated 1 |
| SOD1 | superoxide dismutase 1, soluble |
| SRC | v-src sarcoma (Schmidt-Ruppin A-2) viral oncogene homolog (avian) |
| STAT3 | signal transducer and activator of transcription 3 |
| STAT6 | signal transducer and activator of transcription 6, interleukin-4 |
| TCF7L2 | transcription factor 7-like 2 |
| TEK | TEK tyrosine kinase, endothelial |
| TFAP2B | transcription factor AP-2 beta |
| TGFβ1 | transforming growth factor, beta 1 |
| TIAF1 | TGFB1-induced anti-apoptotic factor 1 |
| TIMP1 | TIMP metallopeptidase inhibitor 1 |
| TNF | tumor necrosis factor |
| TNFRSF1B | tumor necrosis factor receptor superfamily, member 1B |
| TP53 | tumor protein p53 |
| TRAF1 | TNF receptor-associated factor 1 |
| TYMS | thymidylate synthetase |
| VEGFA | vascular endothelial growth factor A |
| XIAP | X-linked inhibitor of apoptosis |

Sense and antisense sequences useful in the synthesis of siRNA are selected according to proprietary and publicly available methods and algorithms.

The chemical modifications provided above are useful in synthesizing nucleotide therapeutics that exhibit inter alia, serum stability, activity, reduced immune response, reduced off target effect.

Antibodies

The term “antibody” refers to IgG, IgM, IgD, IgA, and IgE antibody, inter alia. The definition includes polyclonal antibodies or monoclonal antibodies. This term refers to whole antibodies or fragments of antibodies comprising an antigen-binding domain, e.g. antibodies without the Fc portion, single chain antibodies, miniantibodies, fragments consisting of essentially only the variable, antigen-binding domain of the antibody, etc. The term “antibody” may also refer to antibodies against polynucleotide sequences obtained by cDNA vaccination. The term also encompasses antibody fragments which retain the ability to selectively bind with their antigen or receptor and are exemplified as follows, inter alia:

(1) Fab, the fragment which contains a monovalent antigen-binding fragment of an antibody molecule which can be produced by digestion of whole antibody with the enzyme papain to yield a light chain and a portion of the heavy chain;

(2) $(Fab')_2$, the fragment of the antibody that can be obtained by treating whole antibody with the enzyme pepsin without subsequent reduction; F(ab'2) is a dimer of two Fab fragments held together by two disulfide bonds;

(3) Fv, defined as a genetically engineered fragment containing the variable region of the light chain and the variable region of the heavy chain expressed as two chains; and (4) Single chain antibody (SCA), defined as a genetically engineered molecule containing the variable region of the light chain and the variable region of the heavy chain linked by a suitable polypeptide linker as a genetically fused single chain molecule, including a scFv.

CDR grafting may be performed to alter certain properties of the antibody molecule including affinity or specificity. A non-limiting example of CDR grafting is disclosed in U.S. Pat. No. 5,225,539.

Single-domain antibodies are isolated from the unique heavy-chain antibodies of immunized Camelidae, including camels and llamas. The small antibodies are very robust and bind the antigen with high affinity in a monomeric state. U.S. Pat. No. 6,838,254 describes the production of antibodies or fragments thereof derived from heavy chain immunoglobulins of Camelidae.

A monoclonal antibody (mAb) is a substantially homogeneous population of antibodies to a specific antigen. Monoclonal antibodies (mAbs) are obtained by methods known to those skilled in the art. See, for example Kohler et al (1975); U.S. Pat. No. 4,376,110; Ausubel et al (1987-1999); Harlow et al (1988); and Colligan et al (1993), the contents of which are incorporated entirely herein by reference. The mAbs of the present invention may be of any immunoglobulin class including IgG, IgM, IgE, IgA, and any subclass thereof. A hybridoma producing a mAb may be cultivated in vitro or in vivo. High titers of mAbs are obtained in vivo for example wherein cells from the individual hybridomas are injected intraperitoneally into pristine-primed Balb/c mice to produce ascites fluid containing high concentrations of the desired mAbs. mAbs of isotype IgM or IgG may be purified from such ascites fluid, or from culture supernatants, using column chromatography methods well known to those of skill in the art.

By “specific binding affinity” is meant that the antibody binds to an ENDO180 polypeptide or fragment thereof with greater affinity than it binds to another polypeptide under similar conditions.

The term "epitope" is meant to refer to that portion of a molecule capable of being bound by an antibody which can also be recognized by that antibody. An "antigen" is a molecule or a portion of a molecule capable of being bound by an antibody which is additionally capable of inducing an animal to produce antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

Epitopes or antigenic determinants usually consist of chemically active surface groupings of molecules such as amino acids or sugar side chains and have specific three-dimensional structural characteristics as well as specific charge characteristics.

In one embodiment, the antibody is a monoclonal antibody. In one embodiment, the monoclonal antibody is an IgG, IgM, IgD, IgA, or IgE monoclonal antibody. IgG subclasses are also well known to those in the art and include but are not limited to human IgG1, IgG2, IgG3 and IgG4. In one embodiment the monoclonal antibody is and IgG monoclonal antibody. In one embodiment, the monoclonal antibody is a human, humanized, or chimeric, antibody. In one embodiment, the portion of the antibody is a Fab fragment of the antibody. In one embodiment, the portion of the antibody comprises the variable domain of the antibody. In one embodiment, the portion of the antibody comprises a CDR portion of the antibody. In other embodiments the antibody is a scFv molecule. The antibodies of the present invention may be produced recombinantly (see generally Marshak et al., 1996 "Strategies for Protein Purification and Characterization. A laboratory course manual." Plainview, N.Y.: Cold Spring Harbor Laboratory Press, 1996) and analogs may be produced by post-translational processing. Differences in glycosylation can provide polypeptide analogs.

The antibody may be a human or nonhuman antibody. A nonhuman antibody may be humanized by recombinant methods to reduce its immunogenicity in man. Methods for humanizing antibodies are known to those skilled in the art.

This application provides humanized forms of the above antibodies. As used herein, "humanized" describes antibodies wherein some, most or all of the amino acids outside the CDR regions are replaced with corresponding amino acids derived from human immunoglobulin molecules, e.g. the human framework regions replace the non-human regions. In one embodiment of the humanized forms of the antibodies, some, most or all of the amino acids outside the CDR regions have been replaced with amino acids from human immunoglobulin molecules but where some, most or all amino acids within one or more CDR regions remain unchanged. Small additions, deletions, insertions, substitutions or modifications of amino acids are permissible as long as they would not abrogate the ability of the antibody to bind the antigen, ENDO180.

A "humanized" antibody would retain a similar antigenic specificity as the original antibody, i.e. the ability to bind ENDO180, specifically human ENDO180 receptor and would similarly be internalized by the receptor.

One skilled in the art would know how to produce the humanized antibodies of the subject invention. Various publications, several of which are hereby incorporated by reference into this application, describe how to make humanized antibodies.

For example, the methods described in U.S. Pat. Nos. 4,816,567 and 6,331,415 comprise the production of chimeric antibodies having a variable region of one antibody and a constant region of another antibody.

U.S. Pat. No. 5,225,539; U.S. Pat. No. 6,548,640 and U.S. Pat. No. 6,982,321 describes the use of recombinant DNA technology to produce a humanized antibody wherein the CDRs of one immunoglobulin are replaced with the CDRs from an immunoglobulin with a different specificity such that the humanized antibody would recognize the target antigen but would not illicit an immune response. Specifically, site directed mutagenesis is used to introduce the CDRs onto the framework region.

Other approaches for humanizing an antibody are described in WO 90/07861 and corresponding patents including U.S. Pat. Nos. 5,585,089; 5,693,761; 6,180,370 and 7,022,500. These patents describe a method to increase the affinity of an antibody for the desired antigen by combining the CDRs of a mouse monoclonal antibody with human immunoglobulin framework and constant regions. Human framework regions can be chosen to maximize homology with the mouse sequence. Computer modeling can be used to identify amino acids in the framework region which are likely to interact with the CDRs or the specific antigen and then mouse amino acids can be used at these positions to create the humanized antibody.

The above methods are merely illustrative of some of the methods that one skilled in the art could employ to make humanized antibodies.

The monoclonal antibody E3-8D8 represents a suitable anti-ENDO180 antibody for use in the methods of the present invention. The hybridoma cell E3-8D8 was deposited with the Belgian Co-ordinated Collections of Micro-Organisms (BCCM), under the terms of the Budapest Treaty and given Accession Number LMBP 7203CB.

Epitope Mapping

Epitope mapping studies identify the residues that are important for antibody binding. Various methods are known in the art for epitope mapping and are readily performed by one skilled in the art. Certain methods are described in Epitope Mapping: A Practical Approach (0. M. R. Westwood, F. C. Hay; Oxford University Press, 2000), incorporated herein by reference.

One example of an epitope mapping techniques is Synthetic Labeled Peptides Epitope Mapping whereby a set of overlapping synthetic peptides is synthesized, each corresponding to a small segment of the linear sequence of the protein antigen, i.e. extracellular domain of ENDO180, and arrayed on a solid phase. The panel of peptides is then probed with the test antibody, and bound antibody is detected using an enzyme-labeled secondary antibody.

Other techniques include fragmentation or cleavage and gel separation of the protein antigen, transfer to a membrane, probing by test antibody and bound antibody is detected using an enzyme-labeled secondary antibody.

Antibody Drug Development

In general monoclonal antibodies need to be designed to preserve binding properties (selectivity, internalization etc) and to reduce an immune response in the recipient. Specifically, the monoclonal antibody secreted from hybridoma 3E-8D8 may be optimized for human therapeutics by one of several methods known to those with skill in the art. In one method the variable heavy chain ($V_H$) and variable light chain ($V_L$) of the monoclonal antibody are sequenced. Once the amino acid sequence is known, the complementarity determining regions (CDR), heavy chain and light chain CDR3 are identified and degenerate oligonucleotides are used to clone synthetic CDR3 into a vector to produce a recombinant vector or construct. The construct may be for example a Fab fragment, a F(ab')2 fragment, a Fv fragment, a single chain fragment or a full IgG molecule. The construct(s) is expressed and a polypeptide is isolated. In some embodiments the monoclonal antibody may be further optimized by mutagenesis optimized by site directed mutagenesis to generate a CDR3 domain having substantial identity to the original CDR3.

Therapeutic Agents

The therapeutic agent or active agents according to the present invention includes nucleotide and non-nucleotide agents, including oligonucleotides such as antisense (AS), miRNA and unmodified and chemically modified siRNA compounds. A preferred therapeutic agent is a siRNA compound.

In some embodiments the siRNA targets and reduces expression of a target gene by RNA interference.

The therapeutic oligonucleotides of the present invention are synthesized by any method known in the art for ribonucleic or deoxyribonucleic nucleotides. For example, a commercial polynucleotide synthesizer (e.g. Applied Biosystems 380B DNA synthesizer) can be used. When fragments are used, two or more such sequences can be synthesized and linked together for use in the present invention. Although a siRNA is the preferred therapeutic agent according to the present invention, the present invention encompasses a conjugate or mixture wherein the therapeutic agent is selected from alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analog topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogs); podophyllotoxin; podophyllinic acid; teniposide; cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Agnew, Chem. Intl. Ed. Engl., 1994. 33: 183-186); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; a platinum analog such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); a retinoid such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN®) combined with 5-FU and leucovovin.

Also included in this definition are anti-hormonal agents that act to regulate, reduce, block, or inhibit the effects of hormones that can promote the growth of cancer, and are often administered as systemic, or whole-body treatment. They may be hormones themselves. Examples include anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LY117018, onapristone, and toremifene (FARESTON®); anti-progesterones; estrogen receptor down-regulators (ERDs); agents that function to suppress or shut down the ovaries, for example, leutinizing hormone-releasing hormone (LHRH) agonists such as leuprolide acetate (LUPRON® and ELIGARD®), goserelin acetate, buserelin acetate and tripterelin; other anti-androgens such as flutamide, nilutamide and bicalutamide; and aromatase inhibitors such as, for example, 4(5)-imidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX®). In addition, bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); as well as troxacitabine (a 1,3-dioxolane nucleoside cytosine analog); siRNA, ribozyme and antisense oligonucleotides, particularly those that inhibit expression of genes in signaling pathways implicated in aberrant cell proliferation; vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); lapatinib ditosylate (an ErbB-2 and EGFR dual tyrosine kinase small-molecule inhibitor also known as GW572016); COX-2 inhibitors such as celecoxib (CELEBREX®; 4-(5-(4-methylphenyl)-3-(trifluoromethyl)-1H-pyrazol-1-yl)benzenesulfonamide; and pharmaceutically acceptable salts, acids or derivatives of any of the above.

As used herein, the term "polypeptide" refers to, in addition to a polypeptide, a peptide and a full protein and includes isolated and recombinant polypeptides. As used herein, "biological function" refers to the biological property of the molecule and in this context means an in vivo effector or antigenic function or activity that is directly or indirectly performed by a naturally occurring polypeptide or nucleic acid molecule. Biological functions include but are not limited to receptor binding, any enzymatic activity or enzyme modulatory activity, any carrier binding activity, any hormonal activity, any activity in internalizing molecules or translocation from one compartment to another, any activity in promoting or inhibiting adhesion of cells to extracellular matrix or cell surface molecules, or any structural role, as well as having the nucleic acid sequence encode functional protein and be expressible. The antigenic functions essentially mean the possession of an epitope or an antigenic site that is capable of cross-reacting with antibodies raised against a naturally occurring protein. Biologically active analogs share an effector function of the native polypeptide that may, but need not, in addition possess an antigenic function.

Measurement of the level of the ENDO180 polypeptide may be determined by a method selected from the group consisting of immunohistochemistry, western blotting, ELISA, antibody microarray hybridization and targeted molecular imaging. Such methods are well-known in the art, for example immunohistochemistry, western blotting, antibody microarray hybridization, and targeted molecular imaging.

Measurement of the level of ENDO180 polynucleotide may be determined by a method selected for example from: RT-PCR analysis, in-situ hybridization, polynucleotide microarray and Northern blotting. Such methods are well known in the art.

Antisense Molecules

In some embodiments the therapeutic agent is an antisense oligonucleotide. By the term "antisense" (AS) or "antisense fragment" is meant a polynucleotide fragment (comprising either deoxyribonucleotides, ribonucleotides or a mixture of both) having inhibitory antisense activity, said activity causing a decrease in the expression of the endogenous genomic copy of the corresponding gene. An AS polynucleotide is a polynucleotide which comprises consecutive nucleotides having a sequence of sufficient length and homology to a sequence present within the sequence of the target gene to permit hybridization of the AS to the gene. Many reviews have covered the main aspects of antisense (AS) technology and its therapeutic potential (Aboul-Fadl T., Curr Med Chem. 2005, 12(19):2193-214; Crooke S T, Curr Mol Med. 2004, 4(5):465-87; Crooke S T, Ann Rev Med. 2004, 55:61-95; Vacek M et al, Cell Mol Life Sci. 2003, 60(5):825-33; Cho-Chung Y S, Arch Pharm Res. 2003, 26(3): 183-91. There are further reviews on the chemical (Crooke et al., Hematol Pathol. 1995, 9(2):59-72), cellular (Wagner, Nature. 1994, 372(6504):333-5) and therapeutic (Scanlon, et al, FASEB J. 1995, 9(13): 1288-96) aspects of AS technology. Antisense intervention in the expression of specific genes can be achieved by the use of modified AS oligonucleotide sequences (for recent reports see Lefebvre-d'Hellencourt et al, 1995; Agrawal, 1996; LevLehman et al, 1997).

AS oligonucleotide sequences may be short sequences of DNA, typically 15-30 mer but may be as small as 7-mer (Wagner et al, Nat. Biotech. 1996, 14(7):840-4), designed to complement a target mRNA of interest and form an RNA:AS duplex. This duplex formation can prevent processing, splicing, transport or translation of the relevant mRNA.

Moreover, certain AS nucleotide sequences can elicit cellular RNase H activity when hybridized with their target mRNA, resulting in mRNA degradation (Calabretta et al, Semin Oncol. 1996, 23(1):78-87). In that case, RNaseH will cleave the RNA component of the duplex and can potentially release the AS to further hybridize with additional molecules of the target RNA. An additional mode of action results from the interaction of AS with genomic DNA to form a triple helix, which can be transcriptionally inactive.

The sequence target segment for the antisense oligonucleotide is selected such that the sequence exhibits suitable energy related characteristics important for oligonucleotide duplex formation with their complementary templates, and shows a low potential for self-dimerization or self-complementation (Anazodo et al, 1996, BBRC. 229:305-309). For example, the computer program OLIGO (Primer Analysis Software, Version 3.4), can be used to determine antisense sequence melting temperature, free energy properties, and to estimate potential self-dimer formation and self-complimentary properties. The program allows the determination of a qualitative estimation of these two parameters (potential self-dimer formation and self-complimentary) and provides an indication of "no potential" or "some potential" or "essentially complete potential". Using this program target segments are generally selected that have estimates of no potential in these parameters. However, segments can be used that have "some potential" in one of the categories. A balance of the parameters is used in the selection as is known in the art. Further, the oligonucleotides are also selected as needed so that analog substitution does not substantially affect function.

Phosphorothioate antisense oligonucleotides do not normally show significant toxicity at concentrations that are effective and exhibit sufficient pharmacodynamic half-lives in animals (Agrawal, et al., PNAS USA. 1997, 94(6):2620-5) and are nuclease resistant. Antisense oligonucleotide inhibition of basic fibroblast growth factor (bFGF), having mitogenic and angiogenic properties, suppressed 80% of growth in glioma cells (Morrison, J Biol Chem. 1991 266(2):728-34) in a saturable and specific manner. Being hydrophobic, antisense oligonucleotides interact well with phospholipid membranes (Akhter et al., NAR. 1991, 19:5551-5559). Following their interaction with the cellular plasma membrane, they are actively (or passively) transported into living cells (Loke et al., PNAS 1989, 86(10):3474-8), in a saturable mechanism predicted to involve specific receptors (Yakubov et al., PNAS, 1989 86(17):6454-58)

Ribozymes

A "ribozyme" is an RNA molecule that possesses RNA catalytic ability (see Cech for review) and cleaves a specific site in a target RNA. In accordance with the present invention, ribozymes which cleave mRNA may be utilized as a therapeutic agent. This may be necessary in cases where antisense therapy is limited by stoichiometric considerations (Sarver et al., 1990, Gene Regulation and Aids, pp. 305-325). Ribozymes can then be used that will target the a gene associated with a bone marrow disease. The number of RNA molecules that are cleaved by a ribozyme is greater than the number predicted by stoichiometry. (Hampel and Tritz, Biochem. 1989, 28(12):4929-33; Uhlenbeck, Nature. 1987. 328 (6131):596-600). Ribozymes catalyze the phosphodiester bond cleavage of RNA. Several ribozyme structural families have been identified including Group I nitrons, RNase P, the hepatitis delta virus ribozyme, hammerhead ribozymes and the hairpin ribozyme originally derived from the negative strand of the tobacco ringspot virus satellite RNA (sTRSV) (U.S. Pat. No. 5,225,347). The latter two families are derived from viroids and virusoids, in which the ribozyme is believed to separate monomers from oligomers created during rolling circle replication (Symons, 1989 and 1992). Hammerhead and hairpin ribozyme motifs are most commonly adapted for trans-cleavage of mRNAs for gene therapy (Sullivan, 1994). In general the ribozyme has a length of from about 30-100 nucleotides. Delivery of ribozymes is similar to that of AS fragments and/or siRNA molecules.

siRNA and RNA Interference

RNA interference (RNAi) is a phenomenon involving double-stranded (ds) RNA-dependent gene-specific posttranscriptional silencing. Initial attempts to study this phenomenon and to manipulate mammalian cells experimentally were frustrated by an active, non-specific antiviral defense mechanism which was activated in response to long dsRNA molecules (Gil et al., Apoptosis, 2000. 5:107-114). Later, it was discovered that synthetic duplexes of 21 nucleotide RNAs could mediate gene specific RNAi in mammalian cells, without stimulating the generic antiviral defense mechanisms Elbashir et al. Nature 2001, 411:494-498 and Caplen et al. PNAS 2001, 98:9742-9747). As a result, small interfering RNAs (siRNAs), which are short double-stranded RNAs, have been widely used to inhibit gene expression and understand gene function.

RNA interference (RNAi) is mediated by small interfering RNAs (siRNAs) (Fire et al, Nature 1998, 391:806) or microRNAs (miRNAs) (Ambros V. Nature 2004, 431:350-355); and Bartel D P. Cell. 2004 116(2):281-97). The corresponding process is commonly referred to as specific post-transcriptional gene silencing when observed in plants and as quelling when observed in fungi.

A siRNA is a double-stranded RNA which down-regulates or silences (i.e. fully or partially inhibits) the expression of an endogenous or exogenous gene/mRNA. RNA interference is based on the ability of certain dsRNA species to enter a specific protein complex, where they are then targeted to complementary cellular RNA (i.e. mRNA), which they specifically degrade or cleave. Thus, the RNA interference response features an endonuclease complex containing siRNA, commonly referred to as an RNA-induced silencing complex (RISC), which mediates cleavage of single-stranded RNA having a sequence complementary to the antisense strand of the siRNA duplex. Cleavage of the target RNA may take place in the middle of the region complementary to the antisense strand of the siRNA duplex (Elbashir, et al., Genes Dev., 2001, 15:188). In more detail, longer dsRNAs are digested into short (17-29 bp) dsRNA fragments (also referred to as short inhibitory RNAs or "siRNAs") by type III RNAses (DICER, DROSHA, etc., (see Bernstein et al., Nature, 2001, 409:363-6 and Lee et al., Nature, 2003, 425: 415-9). The RISC protein complex recognizes these fragments and complementary mRNA. The whole process is culminated by endonuclease cleavage of target mRNA (McManus and Sharp, Nature Rev Genet, 2002, 3:737-47; Paddison and Hannon, Curr Opin Mol Ther. 2003, 5(3): 217-24). (For additional information on these terms and proposed mechanisms, see for example, Bernstein, et al., RNA. 2001, 7(11):1509-21; Nishikura, Cell. 2001, 107(4):415-8 and PCT Publication No. WO 01/36646).

Studies have revealed that siRNA can be effective in vivo in mammals including humans. Specifically, Bitko et al., showed that specific siRNAs directed against the respiratory syncytial virus (RSV) nucleocapsid N gene are effective in treating mice when administered intranasally (Nat. Med. 2005, 11(1):50-55). For reviews of therapeutic applications of siRNAs see for example Batik (Mol. Med 2005, 83: 764-773) and Chakraborty (Current Drug Targets 2007 8(3):469-82). In addition, clinical studies with short siRNAs that target the VEGFR1 receptor in order to treat age-related macular degeneration (AMD) have been conducted in human patients (Kaiser, Am J Ophthalmol. 2006 142(4):660-8). Further information on the use of siRNA as therapeutic agents may be found in Durcan, 2008. Mol. Pharma. 5(4):559-566; Kim and Rossi, 2008. BioTechniques 44:613-616; Grimm and Kay, 2007, JCI, 117(12):3633-41.

The siRNA according to the invention is unmodified, recombinant or chemically modified. Examples of chemical modifications useful in synthesizing siRNA are disclosed in PCT Patent Publication No. WO 2009/044392, assigned to the assignee of the present invention, and hereby incorporated by reference in its entirety.

Pharmaceutical Compositions

The present invention provides for a pharmaceutical composition comprising any one of the above compounds and a pharmaceutically acceptable excipient. In some embodiments the pharmaceutical composition according to the present invention comprises one of an anti-ENDO180 antibody or antigen-binding fragment thereof selected from a) the monoclonal antibody produced by the hybridoma cell line E3-8D8 (BCCM Accession Number LMBP 7203CB);
b) an antibody or fragment thereof that binds to the same epitope as the antibody of (a);
c) a humanized antibody of (a) or (b);
d) a recombinant polypeptide comprising amino acid sequences set forth in SEQ ID NO: 6 or a variant thereof; and
e) a recombinant polypeptide comprising CDR3 having amino acid sequences set forth in SEQ ID NO:7 and 8, or variants thereof;
f) a conjugate of any one of the above (a)-(e) conjugated to a moiety;

wherein upon contact with a cell expressing ENDO180 the antibody or antigen binding fragment thereof is internalized into the cell; and a pharmaceutically acceptable vehicle or carrier.

In some embodiments the carrier comprises a lipid particle or a lipidated glycosaminoglycan.

In another aspect the invention provides compounds including a) an anti-ENDO180 antibody or antigen binding fragment thereof; b) a moiety selected from a detectable label, a cytotoxic agent or a therapeutic agent, and c) a nanocarrier.

In various embodiments the nanocarrier is a polysaccharide-based nanoparticle. In various embodiments, tripartite compounds of the invention can be represented by one of the formulas:

A-X-Y

X-A-Y or

X Y A wherein A represents a detectable label, a cytotoxic agent or a therapeutic agent;

X represents a nanocarrier; and

Y represents an anti-ENDO180 antibody or antigen-binding fragment thereof.

The disclosed compounds are designed to target particular cells or tissues expressing the ENDO180 polypeptide, so that a detectable label, a cytotoxic agent or a therapeutic agent is delivered to the desired cell more effectively and with high specificity. For example, one embodiment of the disclosure includes compounds that target cancerous cell and/or tissues.

As such, certain examples of these compounds include a an anti-ENDO180 antibody or antigen binding fragment thereof that binds to an ENDO180 receptor that is present in a higher concentration on a cancer cell than on a normal cell. Embodiments of the disclosed compounds exploit the up-regulated expression of ENDO180 receptors in diseased cells and tissue to selectively deliver a therapeutic agent to such a cell.

In various embodiments the nanocarrier is a polysaccharide-based nanoparticle. In certain embodiments the polysaccharide is a glycosaminoglycan or a mucopolysaccharide. In various embodiments the glycosaminoglycan is selected from the group comprising, without being limited to, hyaluronic acid, chondroitin sulfate, dermatan sulfate, keratan sulfate, heparin, heparan sulfate and combinations thereof.

In certain embodiments the nanocarrier includes organic polymers, including, without being limited to, organic polymers that self assemble to form a self-assembled nanoparticle, which provides an effectively multivalent species. In such embodiments the self-assembled nanoparticles can include the same or different compounds. For example, the self-assembled nanoparticles include compounds having an anti-ENDO180 antibody or antigen-binding fragment thereof a moiety selected from a detectable label, a cytotoxic agent or a therapeutic agent; and the nanocarrier components.

Embodiments of the disclosed compounds include a plurality of therapeutic agents, detectable labels of cytotoxic agents. In such embodiments, the compounds include different therapeutic agents, imaging agents and cytotoxic agents. In certain embodiments compounds having two or more therapeutic agents have increased therapeutic efficiency due to multivalent effects The present invention further provides for a pharmaceutical composition comprising the disclosed compounds and conjugates, formulated for administration to a subject. An additional aspect of the present invention provides for methods of treating a subject having a proliferative disease including cancer, metastatic disease and fibrosis, using the disclosed compounds, and hence pharmaceutical compositions are provided herein for this purpose.

In preferred embodiments the therapeutic agent is a chemically modified siRNA compound that inhibits expression of a target gene set forth in Table A.

In some embodiments the compositions comprise a mixture of two or more different therapeutic agents including two or mores siRNA that target a single gene or multiple genes.

The invention further provides a pharmaceutical composition comprising at least one compound of the invention covalently or non-covalently bound to one or more compounds of the invention in an amount effective to inhibit target gene expression or activity; and a pharmaceutically acceptable carrier.

The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art. The compounds of the present invention can be administered by any of the conventional routes of administration. It should be noted that the compound can be administered as the compound or as pharmaceutically acceptable salt and can be administered alone or as an active ingredient in combination with pharmaceutically acceptable carriers, solvents, diluents, excipients, adjuvants and vehicles. The compounds can be administered orally, subcutaneously or parenterally including intravenous, intraarterial, intramuscular, intraperitoneally, and intranasal administration as well as intrathecal and infusion techniques. Implants of the compounds are also useful. Liquid forms may be prepared for injection, the term including subcutaneous, transdermal, intravenous, intramuscular, intrathecal, and other parental routes of administration. The liquid compositions include aqueous solutions, with and without organic cosolvents, aqueous or oil suspensions, emulsions with edible oils, as well as similar pharmaceutical vehicles. In addition, under certain circumstances the compositions for use in the novel treatments of the present invention may be formed as aerosols, for intranasal and like administration. The patient being treated is a warm-blooded animal and, in particular, mammals including man. The pharmaceutically acceptable carriers, solvents, diluents, excipients, adjuvants and vehicles as well as implant carriers generally refer to inert, non-toxic solid or liquid fillers, diluents or encapsulating material not reacting with the active ingredients of the invention and they include liposomes, lipidated glycosaminoglycans and microspheres. Examples of delivery systems useful in the present invention include U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

In general, the active dose of compound for humans is in the range of from 1 ng/kg to about 20-100 mg/kg body weight per day, preferably about 0.01 mg to about 2-10 mg/kg body weight per day, in a regimen of one dose per day or twice or three or more times per day for a period of 1-2 weeks or longer, preferably for 24- to 48 hrs or by continuous infusion during a period of 1-2 weeks or longer.

Additionally, the invention provides a method of inhibiting the expression of the genes of the present invention by at least 50% as compared to a control comprising contacting an mRNA transcript of the gene of the present invention with one or more of the compounds of the invention.

In one embodiment the therapeutic agent inhibits a target gene, whereby the inhibition is selected from the group comprising inhibition of gene function, inhibition of polypeptide and inhibition of mRNA expression.

The pharmaceutical composition is formulated to provide for a single dosage administration or a multi-dosage administration.

In various embodiments the pharmaceutical composition comprising a conjugate or mixture of the invention is administered intravenously, intramuscularly, locally, or subcutaneously to the subject.

The pharmaceutical composition according to the present invention can also be used in a method for preventing and/or treating a disease as disclosed herein, whereby the method comprises the administration of a conjugate according to the present invention, a mixture according to the present invention or a pharmaceutical composition or medicament according to the present invention for any of the diseases described herein.

Diagnostics

The compounds of the invention are useful in diagnosing ENDO180 expressing cells in biological samples.

Delivery

In some embodiments the antibodies, antigen-binding fragments and/or conjugates of the present invention are delivered to the target tissue by direct application of the naked molecules prepared with a carrier or a diluent.

The term "naked molecule" refers to antibodies, antigen-binding fragments or conjugates that are free from any delivery vehicle that acts to assist, promote or facilitate entry into the cell, including viral sequences, viral particles, lipid particles, liposome formulations, lipofectin or precipitating agents and the like. For example, siRNA in PBS is "naked siRNA". However, in some embodiments the antibodies, antigen-binding fragments or conjugates of the invention are delivered with lipid particles, polysaccharide particles or combinations thereof, liposome formulations, or lipofectin formulations and the like and can be prepared by methods well known to those skilled in the art. Such methods are described, for example, in U.S. Pat. Nos. 5,593,972, 5,589,466, and 5,580,859, which are herein incorporated by reference.

In other embodiments the antibodies, antigen-binding fragments or conjugates of the invention are attached to or are entrapped within a delivery particle. In some embodiments the ENDO180 binding domain of the conjugate molecule is exposed on the external surface of delivery particle. In some embodiments the delivery particle is a liposome. In specific preferred embodiment the delivery particle is a lipidated glycosaminoglycan particle. Such particles are described, for example in U.S. patent application Ser. No. 10/487,022 (Publication No. 20040241248), U.S. patent application Ser. No. 11/718,485 (Publication No. 20080248092), U.S. patent application Ser. No. 11/632,647 (Publication No. 20090022656), which are herein incorporated by reference Without wishing to be bound to theory, the antibody or antigen-binding fragment thereof is exposed on the surface of the delivery particle and homes in on or targets the target cell expressing an ENDO180 polypeptide on its surface.

The pharmaceutically acceptable carriers, solvents, diluents, excipients, adjuvants and vehicles as well as implant carriers generally refer to inert, non-toxic solid or liquid fillers, diluents or encapsulating material not reacting with the active ingredients of the invention and they include liposomes and microspheres. Examples of delivery systems useful in the present invention include U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art. In one specific embodiment of this invention topical and transdermal formulations may be selected. The siRNAs or pharmaceutical compositions of the present invention are administered and dosed in accordance with good medical practice, taking into account the clinical condition of the individual patient, the disease to be treated, the site and method of administration, scheduling of administration, patient age, sex, body weight and other factors known to medical practitioners.

The "therapeutically effective dose" for purposes herein is thus determined by such considerations as are known in the art. The dose must be effective to achieve improvement including but not limited to improved survival rate or more rapid recovery, or improvement or elimination of symptoms and other indicators as are selected as appropriate measures by those skilled in the art.

In general, the active dose of compound for humans is in the range of from 1 ng/kg to about 20-100 mg/kg body weight per day, preferably about 0.01 mg to about 2-10 mg/kg body weight per day, in a regimen of one dose per day or twice or three or more times per day for a period of 1-4 weeks or longer.

The compounds of the present invention can be administered by any of the conventional routes of administration. It should be noted that the compound can be administered as the compound or as pharmaceutically acceptable salt and can be administered alone or as an active ingredient in combination with pharmaceutically acceptable carriers, solvents, diluents, excipients, adjuvants and vehicles. The compounds can be administered orally, subcutaneously or parenterally including intravenous, intraarterial, intramuscular, intraperitoneally, and intranasal, inhalation, transtympanic administration as well as intrathecal and infusion techniques. Implants of the compounds are also useful. Liquid forms may be prepared for injection, the term including subcutaneous, transdermal, intravenous, intramuscular, intrathecal, intranasal and other parental routes of administration. The liquid compositions include aqueous solutions, with and without organic co-solvents, aqueous or oil suspensions, emulsions with edible oils, as well as similar pharmaceutical vehicles. In a particular embodiment, the administration comprises intravenous administration. In another embodiment the administration comprises topical or local administration. In addition, in certain embodiments the compositions for use in the novel treatments of the present invention may be formed as aerosols, for example for intranasal administration.

In certain embodiments, oral compositions (such as tablets, suspensions, solutions) may be effective for local delivery to the oral cavity such as oral composition suitable for mouthwash for the treatment of oral mucositis.

Liquid forms are prepared for drops or spray. The liquid compositions include aqueous solutions, with and without organic co-solvents, aqueous or oil suspensions, emulsions with oils, as well as similar pharmaceutical vehicles. In some embodiments administration comprises topical or local administration.

These compounds are administered to humans and other animals for therapy by any suitable route of administration to the eye, as by, for example, a spray or drops, and topically, as by ointments, suspensions or drops.

In preferred embodiments the subject being treated is a warm-blooded animal and, in particular, mammals including human.

Suitable methods for delivery of the compounds of present invention include, among others, systemic delivery, transfection, lipofection, and electroporation. In a further aspect the present invention is related to a pharmaceutical composition comprising a delivery molecule-therapeutic agent conjugate or an anti-ENDO180 antibody or anti-ENDO180 antibody-therapeutic agent mixture according to the present invention and, a pharmaceutically acceptable carrier, diluent or adjuvants or other vehicle(s).

Preferably, such carrier, diluents, adjuvants and vehicles are inert, and non-toxic. The pharmaceutical composition is in its various embodiments adapted for administration in various ways. Such administration comprises systemic and local administration as well as oral, subcutaneous, parenteral, intravenous, intraarterial, intramuscular, intraperitoneal, intranasal, intrathecal, transtympanic and intraocular.

In some embodiments the vehicle is selected from a lipid particle, a polysaccharide particle or a combination thereof and a lipidated glycosaminoglycan particle (gagomer). In various embodiments the delivery molecule-therapeutic agent conjugate or antibody-therapeutic mixture is at least partially exposed on the external surface of the lipid particle or the lipidated glycosaminoglycan particle.

It will be acknowledged by the one skilled in the art that the amount of the pharmaceutical composition and the respective siRNA depends on the clinical condition of the individual patient, the site and method of administration, scheduling of administration, patient age, sex, bodyweight and other factors known to medical practitioners. The pharmaceutically effective amount for purposes of prevention and/or treatment is thus determined by such considerations as are known in the medical arts. Preferably, the amount is effective to achieve improvement including but limited to improve the diseased condition or to provide for a more rapid recovery, improvement or elimination of symptoms and other indicators as are selected as appropriate measures by those skilled in the medical arts.

Combination Therapy

In various embodiments the present invention relates to combination therapy. In one embodiment, the co-administration of two or more therapeutic agents achieves a synergistic effect, i.e., a therapeutic affect that is greater than the sum of the therapeutic effects of the individual components of the combination. In another embodiment, the co-administration of two or more therapeutic agents achieves an additive effect.

The active ingredients that comprise a combination therapy may be administered together via a single dosage form or by separate administration of each active agent. In certain embodiments, the first and second therapeutic agents are administered in a single dosage form. The agents may be formulated into a single tablet, pill, capsule, or solution for parenteral administration and the like. Alternatively, the first therapeutic agent and the second therapeutic agents may be administered as separate compositions. The first active agent may be administered at the same time as the second active agent or the first active agent may be administered intermittently with the second active agent. The length of time between administration of the first and second therapeutic agent may be adjusted to achieve the desired therapeutic effect. For example, the second therapeutic agent may be administered only a few minutes (e.g., 1, 2, 5, 10, 30, or 60 min) or several hours (e.g., 2, 4, 6, 10, 12, 24, or 36 hr) after administration of the first therapeutic agent. In certain embodiments, it may be advantageous to administer more than one dosage of one of the therapeutic agents between administrations of the second therapeutic agent. For example, the second therapeutic agent may be administered at 2 hours and then again at 10 hours following administration of the first therapeutic agent. Alternatively, it may be advantageous to administer more than one dosage of the first therapeutic agent between administrations of the second therapeutic agent. Importantly, it is preferred that the therapeutic effects of each active ingredient overlap for at least a portion of the duration of each therapeutic agent so that the overall therapeutic effect of the combination therapy is attributable in part to the combined or synergistic effects of the combination therapy.

The present invention relates to compounds and the use of compounds, which down-regulate the expression of the genes of the invention particularly to conjugates comprising small interfering RNAs (siRNAs). Methods, molecules and compositions useful for inhibition of target genes are discussed herein at length, and any of said molecules and/or compositions may be beneficially employed in the treatment of a subject suffering from a proliferative or fibrotic disease.

Methods of Treatment

An additional aspect of the present invention provides for methods of treating a proliferative disease including cancer, metastatic disease and fibrosis. Methods for therapy of diseases or disorders associated with uncontrolled, pathological cell growth, e.g. cancer, psoriasis, autoimmune diseases, inter alia, and methods for therapy of diseases associated with ischemia and lack of proper blood flow, e.g. myocardial infarction (MI) and stroke, are provided. In particular, the compounds and compositions of the invention are useful in treating proliferative diseases in which ENDO180 is expressed in at least a portion of the diseased cells and or tissue.

"Cancer" or "Tumor" refers to an abnormal proliferation of cells. These terms include both primary tumors, which may be benign or malignant, as well as secondary tumors, or metastases which have spread to other sites in the body. Examples of proliferative diseases include, inter alia: carcinoma (e.g.: breast, colon and lung), leukemia such as B cell leukemia, lymphoma such as B-cell lymphoma, blastoma such as neuroblastoma and melanoma and sarcoma. It will be acknowledged that the pharmaceutical composition according to the present invention can be used for any disease which involves undesired development or growth of vasculature including angiogenesis, as well as any of the diseases and conditions described herein.

The present invention provides methods and compositions for treating a patient suffering from a cancerous proliferative disease, (e.g. lung cancer, breast cancer, cervical cancer, colon cancer, gastric cancer, kidney cancer, leukemia, liver cancer, lymphoma, ovarian cancer, pancreatic cancer, prostate cancer, rectal cancer, sarcoma, skin cancer, testicular cancer, and uterine cancer) which the cancer cell expresses ENDO180 polypeptide. In one particular embodiment, the cancer is renal cancer including RCC and TCC.

"Cancer and "cancerous disease" are used interchangeably and refer to a disease that is caused by or results in inappropriately high levels of cell division, inappropriately low levels of apoptosis, or both. Examples of cancerous diseases include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangio sarcoma, lymphangioendotheliosarcoma, synovioma, mesothelioma, Ewing's tumor, leiomyo sarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, crailiopharyngioma, ependymoma, pinealoma, hemangioblastoma, acoustic neuroma, oligodenroglioma, schwamioma, meningioma, melanoma, neuroblastoma, and retinoblastoma). Metastases of a primary cancer is included. In some preferred embodiments the compounds of the present invention are useful in treating renal cancer, breast cancer, ovarian cancer and metastases thereof in various organs including lung and bone.

As used herein, the term "proliferative disease" refers to any disease in which cellular proliferation, either malignant or benign, contributes to the pathology of the condition. Such unwanted proliferation is the hallmark of cancer and many chronic inflammatory diseases, thus examples of "proliferative disease" include the cancers listed supra and chronic inflammatory proliferative diseases such as psoriasis, inflammatory bowel disease and rheumatoid arthritis; proliferative cardiovascular diseases such as restenosis; proliferative ocular disorders such as diabetic retinopathy; and benign hyperproliferative diseases such as hemangiomas.

Fibrotic Disease

Fibrotic diseases are a group of chronic disease characterized by the excess production of a fibrous material called the extracellular matrix, which contributes to abnormal changes in tissue architecture and interferes with normal organ function. Millions of people worldwide suffer from these chronic diseases, that are often life threatening. Unfortunately, although fibrosis is widely prevalent, debilitating and often life threatening, there is no effective treatment currently available.

The human body responds to trauma and injury by scarring. Fibrosis, a type of disorder characterized by excessive scarring, occurs when the normal wound healing response is disturbed. During fibrosis, the wound healing response continues causing an excessive production and deposition of collagen.

Although fibrotic disorders can be acute or chronic, the disorders share a common characteristic of excessive collagen accumulation and an associated loss of function when normal tissue is replaced with scar tissue.

Fibrosis results from diverse causes, and may be established in various organs. Cirrhosis, pulmonary fibrosis, sarcoidosis, keloids, hypertension and kidney fibrosis, are all chronic diseases that induce a progressive fibrosis which causing a continuous loss of tissue function.

Acute fibrosis (usually with a sudden and severe onset and of short duration) occurs as a common response to various forms of trauma including accidental injuries (particularly injuries to the spine and central nervous system), infections, surgery (cardiac scarring following heart attack), burns, environmental pollutants, alcohol and other types of toxins, acute respiratory distress syndrome, radiation and chemotherapy treatments. All tissues damaged by trauma are prone to scar and become fibrotic, particularly if the damage is repeated. Deep organ fibrosis is often extremely serious because the progressive loss of organ function leads to morbidity, hospitalization, dialysis, disability and even death. Fibrotic diseases or diseases in which fibrosis is evident include pulmonary fibrosis, interstitial lung disease, human fibrotic lung disease, liver fibrosis, cardiac fibrosis, macular degeneration, retinal and vitreal retinopathy, myocardial fibrosis, Grave's ophthalmopathy, drug induced ergotism, cardiovascular disease, atherosclerosis/restenosis, keloids and hypertrophic scars, Hansen's disease and inflammatory bowel disease, including collagenous colitis.

Further information on different types of fibrosis may be found for example in Yu et al (2002), "Therapeutic strategies to halt renal fibrosis", Curr Opin Pharmacol. 2(2):177-81; Keane and Lyle (2003), "Recent advances in management of type 2 diabetes and nephropathy: lessons from the RENAAL study", Am J Kidney Dis. 41(3 Suppl 2): S22-5; Bohle et al (1989), "The pathogenesis of chronic renal failure", Pathol Res Pract. 185(4):421-40; Kikkawa et al (1997), "Mechanism of the progression of diabetic nephropathy to renal failure", Kidney Int Suppl. 62:S39-40; Bataller and Brenner (2001), "Hepatic stellate cells as a target for the treatment of liver fibrosis", Semin Liver Dis. 21(3):437-51; Gross and Hunninghake (2001) "Idiopathic pulmonary fibrosis", N Engl J Med. 345(7):517-25; Frohlich (2001) "Fibrosis and ischemia: the real risks in hypertensive heart disease", Am J Hypertens; 14(6 Pt 2):194S-199S.

Diabetic Nephropathy

Diabetic nephropathy, hallmarks of which are glomerulosclerosis and kidney fibrosis, is the single most prevalent cause of end-stage renal disease in the modern world, and diabetic patients constitute the largest population on dialysis. Such therapy is costly and far from optimal. Transplantation offers a better outcome but suffers from a severe shortage of donors. More targeted therapies against diabetic nephropathy (as well as against other types of kidney pathologies) are not developed, since molecular mechanisms underlying these pathologies are largely unknown. Identification of an essential functional target gene that is modulated in the disease and affects the severity of the outcome of diabetes nephropathy has a high diagnostic as well as therapeutic value.

It is known in the art that many pathological processes in the kidney eventually culminate in similar or identical morphological changes, namely glomerulosclerosis and fibrosis. Human kidney disease may evolve from various origins including glomerular nephritis, nephritis associated with systemic lupus, cancer, physical obstructions, toxins, metabolic disease and immunological diseases, all of which culminate in kidney fibrosis. The meaning of this phenomenon is that different types of insults converge on the same single genetic program resulting in two hallmarks of fibrosis: the proliferation of fibroblasts and overproduction by them of various protein components of connective tissue. In addition, thickening of the basal membrane in the glomeruli accompanies interstitial fibrosis and culminates in glomerulosclerosis. Genes encoding proteins that are involved in kidney fibrosis and glomerulosclerosis may be roughly divided into two groups:

1. Genes, the expression of which leads to the triggering of proliferation of fibroblasts and overproduction by them of various protein components of connective tissue. These may be specific to different pathological conditions; and
2. Genes, the expression of which leads to the execution of the "fibrotic or sclerotic programs". These may be common to all renal pathologies leading to fibrosis and glomerulosclerosis.

The identification of genes that belong to the second group should contribute to the understanding of molecular mechanisms that accompany fibroblast and mesangial cell proliferation and hypersecretion, and may constitute genetic targets for drug development, aimed at preventing renal failure. Application of such drugs is expected to suppress, retard, prevent, inhibit or attenuate progression of fibrosis and glomerulosclerosis.

Combination Therapy

The present invention provides for combination therapy for proliferative disease as disclosed herein and in particular cancer. In said combination therapy, one or more genes are targeted to ameliorate symptoms of the disease being treated. These genes are inhibited the antibody-nucleotide complex of the present invention.

Kits

Kits comprising at least one anti-ENDO180 monoclonal antibody of the invention are further provided. A "kit" refers to any manufacture (e.g., a package or a container) comprising at least one reagent, i.e., an antibody, for specific binding to ENDO180. The kit may be used for performing the methods of the present invention, including therapeutic treatment and diagnostics Additionally, the kit may contain a package insert describing the kit, its content and methods for use.

In one embodiment, a kit of the invention comprises at least composition comprising an anti-ENDO180 antibody or antigen binding fragment thereof selected from a) the monoclonal antibody produced by the hybridoma cell line E3-8D8 (BCCM Accession Number LMBP 7203CB);
b) an antibody or fragment thereof that binds to the same epitope as the antibody in (a);
c) a fragment of an antibody comprising a polypeptide substantially similar to SEQ ID NO: 6; and
d) a recombinant polypeptide comprising CDRs having an amino acid sequence substantially similar to amino acid sequences set forth in SEQ ID NO:7 and 8.

The invention has been described in an illustrative manner, and it is to be understood that the terminology which has been used is intended to be in the nature of words of description rather than of limitation.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

EXAMPLES

General Methods in Molecular Biology

Standard molecular biology techniques known in the art and not specifically described were generally followed as in Sambrook et al., Molecular Cloning: A Laboratory Manual, Cold Spring Harbor Laboratory Press, New York (1989), and in Ausubel et al., Current Protocols in Molecular Biology, John Wiley and Sons, Baltimore, Md. (1989) and in Perbal, A Practical Guide to Molecular Cloning, John Wiley & Sons, New York (1988), and in Watson et al., Recombinant DNA, Scientific American Books, New York and in Birren et al (eds) Genome Analysis: A Laboratory Manual Series, Vols. 1-4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out generally as in PCR Protocols: A Guide To Methods And Applications, Academic Press, San Diego, Calif. (1990). In situ (In cell) PCR in combination with Flow Cytometry can be used for detection of cells containing specific DNA and mRNA sequences (Testoni et al., 1996, Blood 87:3822.)

General methods in immunology: Standard methods in immunology known in the art and not specifically described are generally followed as in Stites et al (eds), Basic and Clinical Immunology (8th Edition), Appleton & Lange, Norwalk, Conn. (1994) and Mishell and Shiigi (eds), Selected Methods in Cellular Immunology, W.H. Freeman and Co., New York (1980).

Immunoassays: ELISA immunoassays are well known to those skilled in the art. Both polyclonal and monoclonal antibodies can be used in the assays. Where appropriate, other immunoassays such as radioimmunoassays (RIA) can be used as are known to those skilled in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al., Molecular Cloning: A Laboratory Manual, Cold Springs Harbor, N.Y., 1989.

Antibody Production

By the term “antibody” as used in the present invention is meant both polyclonal and monoclonal complete antibodies as well as fragments thereof, such as Fab, F(ab')2, scFv and Fv, which are capable of binding the epitope determinant. These antibody fragments retain the ability to selectively bind with its antigen or receptor and are exemplified as follows, inter alia:

A Fab, the fragment which contains a monovalent antigen-binding fragment of an antibody molecule can be produced by digestion of whole antibody with the enzyme papain to yield a light chain and a portion of the heavy chain;

A $(Fab')_2$, the fragment of the antibody that can be obtained by treating whole antibody with the enzyme pepsin without subsequent reduction; F(ab'2) is a dimer of two Fab fragments held together by two disulfide bonds;

A Fv, defined as a genetically engineered fragment containing the variable region of the light chain and the variable region of the heavy chain expressed as two chains; and A scFv fragment (i.e. a single chain antibody (“SCA”), defined as a genetically engineered molecule containing the variable region of the light chain and the variable region of the heavy chain linked by a suitable polypeptide linker as a genetically fused single chain molecule.

Such fragments having antibody functional activity can be prepared by methods known to those skilled in the art (Bird et al. (1988) Science 242:423-426)

Conveniently, antibodies may be prepared against an immunogen or portion thereof, for example, a synthetic peptide based on the sequence, or prepared recombinantly by cloning techniques or the natural gene product and/or portions thereof may be isolated and used as the immunogen. Immunogens can be used to produce antibodies by standard antibody production technology well known to those skilled in the art, as described generally in Harlow and Lane (1988), Antibodies: A Laboratory Manual, Cold Spring Harbor Laboratory, Cold Spring Harbor, N.Y., and Borrebaeck (1992), Antibody Engineering—A Practical Guide, W.H. Freeman and Co., NY.

For producing polyclonal antibodies a host, such as a rabbit or goat, is immunized with the immunogen or immunogen fragment, generally with an adjuvant and, if necessary, coupled to a carrier; antibodies to the immunogen are collected from the sera. Further, the polyclonal antibody can be absorbed such that it is monospecific; that is, the sera can be absorbed against related immunogens so that no cross-reactive antibodies remain in the sera, rendering it monospecific.

For producing monoclonal antibodies the technique involves hyperimmunization of an appropriate donor with the immunogen, generally a mouse, and isolation of splenic antibody-producing cells. These cells are fused to an immortal cell, such as a myeloma cell, to provide a fused cell hybrid that is immortal and secretes the required antibody. The cells are then cultured, in bulk, and the monoclonal antibodies harvested from the culture media for use.

For producing recombinant antibody see generally Huston et al. (1991) “Protein engineering of single-chain Fv analogs and fusion proteins” in Methods in Enzymology (J J Langone, ed., Academic Press, New York, N.Y.) 203:46-88; Johnson and Bird (1991) “Construction of single-chain Fvb derivatives of monoclonal antibodies and their production in *Escherichia coli* in Methods in Enzymology (J J Langone, ed.; Academic Press, New York, N.Y.) 203:88-99; Mernaugh and Mernaugh (1995) "An overview of phage-displayed recombinant antibodies" in Molecular Methods In Plant Pathology (R P Singh and US Singh, eds.; CRC Press Inc., Boca Raton, Fla.:359-365). Additionally, messenger RNAs from antibody-producing B-lymphocytes of animals, or hybridoma can be reverse-transcribed to obtain complementary DNAs (cDNAs). Antibody cDNA, which can be full or partial length, is amplified and cloned into a phage or a plasmid. The cDNA can be a partial length of heavy and light chain cDNA, separated or connected by a linker. The antibody, or antibody fragment, is expressed using a suitable expression system to obtain recombinant antibody. Antibody cDNA can also be obtained by screening pertinent expression libraries.

The antibody can be bound to a solid support substrate or conjugated with a detectable moiety or be both bound and conjugated as is well known in the art. (For a general discussion of conjugation of fluorescent or enzymatic moieties see Johnstone & Thorpe (1982), Immunochemistry in Practice, Blackwell Scientific Publications, Oxford). The binding of antibodies to a solid support substrate is also well known in the art (for a general discussion, see Harlow & Lane (1988) Antibodies: A Laboratory Manual, Cold Spring Harbor Laboratory Publications, New York; and Borrebaeck (1992), Antibody Engineering—A Practical Guide, W.H. Freeman and Co.). The detectable moieties or label contemplated with the present invention include, but are not limited to, fluorescent, metallic, enzymatic and radioactive markers such as biotin, gold, ferritin, alkaline phosphatase, β-galactosidase, peroxidase, urease, fluorescein, rhodamine, tritium, 14C and iodine.

Recombinant Protein Purification

For standard purification, see Marshak et al. (1996), "Strategies for Protein Purification and Characterization. A laboratory course manual." CSHL Press.

The polynucleotide sequence of human ENDO180 mRNA is set forth in accession number NM_006039: 5641 bases, of that the open reading frame (ORF) is 4439 bases (from 117-4441); the polypeptide sequence of 1479 amino acids (aa) is set forth in accession number NP_006030 with gene identifier number: GI:110624774. The mouse mRNA sequence is 5818 bases, accession number MMU56734 with ORF of 1479 aa.

ENDO180 comprises several protein domains, as follows: 1-31 aa SP (signal peptide); 41-161 aa cysteine rich N-terminal domain; 180-228 aa FNII (fibronectin type II) domain; 8 CDR (carbohydrate recognition domain) domains 1CRD-8CRD (235-360 aa 1CRD, 382-505 aa 2CRD, 521-645 aa 3CRD, 669-809 aa 4CRD, 825-951 aa 5CRD, 972-1108 aa 6CRD, 1161-1244 aa 7CRD, 1261-1394 aa 8CRD); 1413-1435 aa 1 TM (transmembrane domain), 1437-1479 aa-cytoplasmic domain.

Reference to Sequence Listing

The sequences described in the specification (SEQ ID NOS:1-9) are being submitted with this application via the USPTO electronic filing system (EFS) in a text file titled, "202-PCT1.5T25.txt" created on Mar. 23, 2010 file size 36 KB, and are hereby incorporated by reference herein in their entirety.

Example 1

Identification of ENDO180 Overexpression by Microarray Hybridization Study

In accordance with the present invention, the microarray hybridization approach was utilized in order to discover genes that are differentially regulated in diabetic nephropathy and kidney fibrosis.

Microarray-based analysis of gene expression was based on the analysis of human fibroblasts subject to selected stimuli resulting in changes in extracellular collagen accumulation and proliferation—the hallmarks of fibrosis. According to the present invention, a specific "Fibrosis" DNA chip was first prepared followed by a microarray hybridization experiments with 19 different types of probes. Analysis of the results was carried out by proprietary algorithms, and analysis of the selected set of genes was performed by the inventors using bioinformatics and the scientific literature.

Example 2

Production of Human Anti-ENDO180 Antibodies

The aim was to generate anti-ENDO180 antibodies that bind to the extracellular portion of ENDO180 and internalize an anti-ENDO180 antibody-cargo complex/conjugate.

Antigen production: The structural considerations in selecting an antigen for antibody production included the information that amino acids 1-522 (SEQ ID NO:9) spatially create the ligand binding structure.

Recombinant ENDO180 antigen was produced by cloning nucleotides 1-1566 of human ENDO180 polynucleotide into an expression vector comprising the FLAG epitope. The polynucleotide sequence of the recombinant clone is set forth in SEQ ID NO:3, the amino acid sequence is set forth in SEQ ID NO:4. The vectors were transfected into 293T cells and a clones expressing the 59 KD partial extracellular domain of human ENDO180 were identified. The ECDhENDO180-FLAG protein was isolated as follows: about 2.2 liters of conditioned medium were filtered through a 0.22 um filter. Medium was loaded on a pre-equilibrated (with TBS) M2 agarose (5 ml, Sigma) at a flow rate of 1 ml/min. Resin was washed with 10 column volumes using TBS and then 10 volumes with 50 mM Tris pH 7.5, 1M NaCl and finally with 10 volumes of TBS. Elution was done with 10 ml of 0.5 mg/ml FLAG peptide in TBS pH 7.5 (final pH). Resin was incubated for 20 min with elution buffer before starting the flow out of column. Sample was concentrated and depleted of FLAG peptide using VivaSpin™ (cut-off 10 Kd). Glycerol was added to 10% final and protein was flash frozen in liquid nitrogen.

Identification of minibodies: minibody antibodies were identified according to the methods disclosed in Di Niro et al, 2007. Construction of miniantibodies for the in vivo study of human autoimmune diseases in animal models. BMC Biotechnology 7:46.

Certain preferred antibodies according to the present invention are recombinant polypeptides comprising heavy chain and light chain CDR3 domains having amino acid sequences set forth in SEQ ID NO:7 and in SEQ ID NO:8.

Example 3

Anti-ENDO180 Monoclonal Antibodies

Methods and Summary:

1. Labeling of mAbs and MB with CypHer5e was performed according to manufacturer's directions. (GE Healthcare).
2. Labeled vs. unlabeled mAbs and MB were tested for binding to purified ENDO180 extra-cellular domain by standard ELISA.

Clones 6D6, 8D8, 8E7 and 9G10 displayed saturated binding to endo180DCTLD3-8-FLAG even after labeling with CypHer5E. In contrast, binding of clone 8D2 and MB (minibody) was significantly impaired upon labeling.

3. Internalization assays were performed according to methods to those skilled in the art.

After 1 hr at 37° C., ENDO180 expressing cells that were incubated with labeled mAbs 6D6, 8D8, 8E7 and 9G10, displayed some increase in fluorescence. Most notably, the same cells that were incubated with labeled MB, showed strong fluorescence. This increase in fluorescence was not seen in control cells or in ENDO180 cells at 40 C. In addition, control mAb (10F12) had no effect 4. Kinetics experiments Based on the results of previous experiments, mAb 6D6, 8D8 and MB were tested. In the 10 min-1 hr kinetics experiment, mAb 8D8 and MB showed the best internalization. All negative controls, control cells, (4° C.; shown as 4OC in some figures) and control mAb-were negative.

Details of Experiments and Results

Anti-ENDO180 monoclonal antibodies (mAb) were generated against the most N-terminal domain (1-522 aa) of human ENDO180 (SEQ ID NO:9) and were screened for internalization in an ENDO180-specific manner per se and conjugated to the fluorophore, CypHer5E.

mAbs production: About 8 liters of each hybridoma were grown in DMEM medium supplemented with 5% FBS IgG FREE, 1% Penstrep, 1% L-Glutamine, 50 μg/ml Gentamycin, 2.5 μg/ml Amphotricin B (Fungizone). About 60 ml was obtained from cell line flasks, with an antibody concentration of about 200 μg/ml. The duration of the growth was 1 month. The purification was done using Protein A Sepharose column followed by two cycles of sizing column.

The mAb 8D8 (E3-8D8), 6D6, 8E7, 9G10, 8D2 were selected for conjugation to labeling moieties.

The mAbs were covalently linked to CypHer5E (Cat #pA15405, Amersham) a red excited fluorescent pH sensitive cyanine dye according to manufacturer's instructions in a molar ratio of 20:1 CypHer5E:Antibody. The fluorophore is excited in acidic pH, as found within the endosome. Therefore, those antibodies that get internalized will be seen as fluorescent signals in cellular vesicles. The mAbs were covalently linked to biotin using EZ-Sulfo-NHS-biotin (Pierce, Cat #21217, Lot #CE49927). Biotinylation was performed according to manufacturer's instructions using a molar ratio of 20:1 Biotin:Antibody at room temperature for 30 min. Following covalently binding of mAbs to CypHer5E or biotin, the antibody solution was dialyzed overnight at 4° C. against solution of PBS following additional two hours at room temperature against a fresh PBS solution. Labeling of mAbs and scFv (SEQ ID NO. 6, also referred to as "minibody") with CypHer5E was performed according to manufacture's instructions (GE Healthcare).

Internalization of the conjugated receptor was performed in the absence of collagen (ligand independent internalization). The following clones were shown to secrete antibodies that bind specifically to ENDO180: Clones 6D6, 8D8, 8E7 and 9G10 displayed saturated binding to endo180DCTLD3-8-FLAG per se and when labeled with CypHer5E. Clone 8D2 showed limited uptake into cells following labeling while clone 10F12 exhibited significant and saturated binding to endo180DCTLD3-8-FLAG which was diminished after labeling.

Figure 2B:
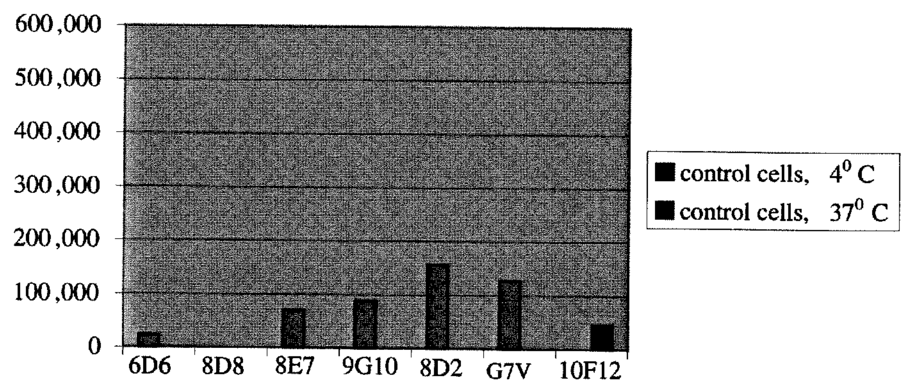

Cells expressing ENDO180 (NRK52E-ENDO180) and control cells (NRK52E) were incubated at 37° C. with the indicated anti-ENDO180 mAbs or control mAbs, covalently linked to CypHer5E. The mAbs were also incubated at 4° C. with ENDO180 cells. The cells were plated in a 96-well plate and fluorescence was measured by Analyst AD &HT, Biosystems (excitation 530 nm, emission 590 nm, dichroic 560 nm). A steady increase in fluorescence at 37° C. in ENDO180 cells was seen with one mAb (E3-8D8). In contrast, fluorescence was not seen in control cells, at 4° C. or with control mAbs. Antibody binding and internalization was tested in ENDO180 expressing NRK52 cells at permissive (37° C.) and non-permissive (4° C.) temperature and tested after one hour. FIG. 2A shows level of fluorescence in ENDO180 expressing calls at permissive (37° C.) and non-permissive (4° C.). Clones 6D6 and 8D8 and the scFv (SEQ ID NO:6) show highest level of internalization. FIG. 2B shows that 8D8 exhibits no non-specific binding.

The ENDO180 receptor was shown to be an internalization and recycling receptor (Howard and Isacke, 2002, JBC 277, 35:32320-31) yet not all antibodies produced are internalized at the same rate or in the same amount. mAb 8D8 and the G7V scFv showed unexpected internalization. No mAb 10F2 was internalized, even after 8 hours.

Kinetics of internalization was studied: NRK52 cells stably expressing human ENDO180-FLAG or empty vector, were seeded in TC-grade black 96-well plates at a density of 6000 cells/well. At 24 or 48 hrs later, mAbs (5 ug/ml in growth medium) were added to the wells, 100 ul/well at either room temperature or on ice (for control plates). The plates were immediately incubated at 37° C. for various times. Control plates were kept on ice for the required times. At each time point, the plates were washed 3× in 200 ul ice-cold PBS. After last wash, 100 ul ice-cold PBS was added and plates read using Analyst at Ex 610 nm/Em 670 nm.

Figure 2C:
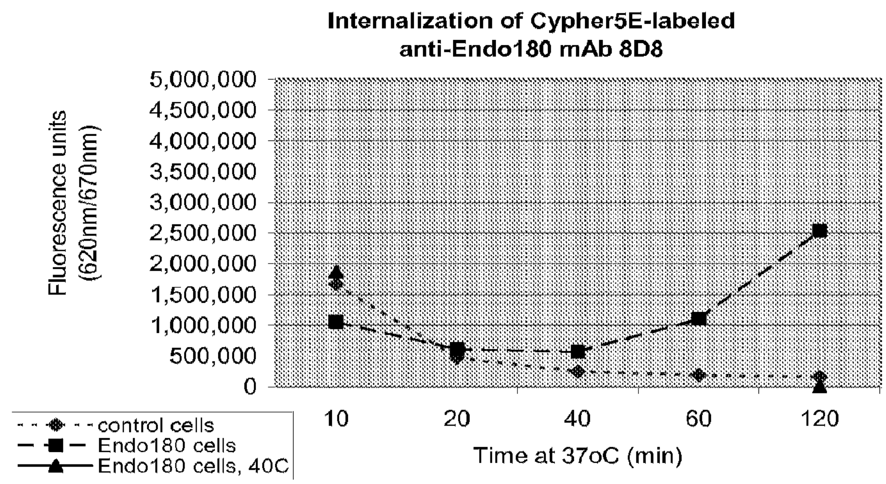
Figure 2D:
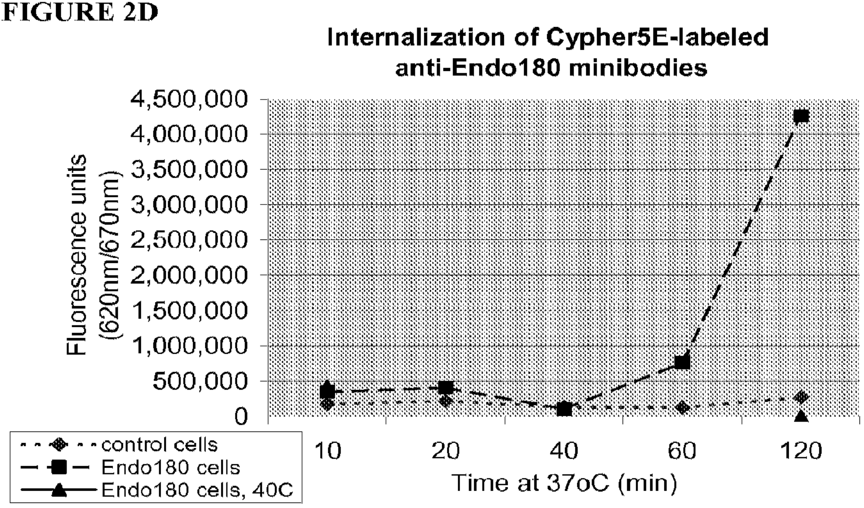
Figure 2E:
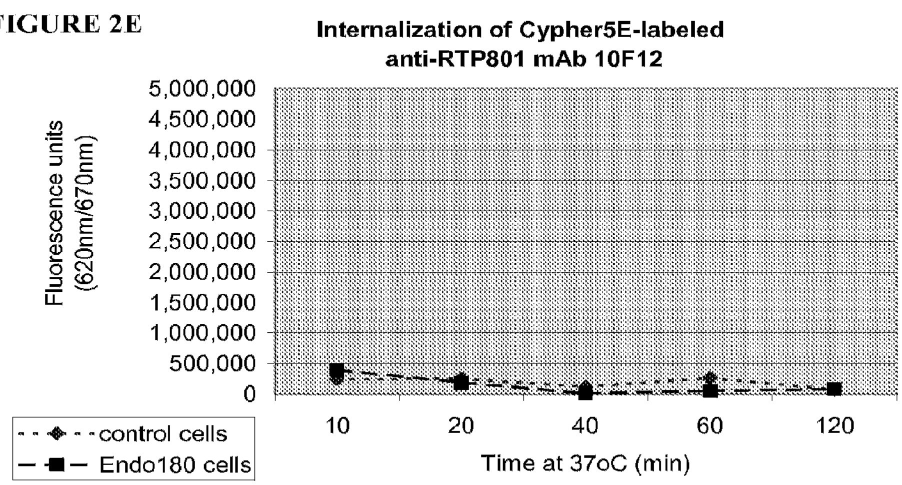

FIGS. 2C-2E show a 10-minute to 1-hour time course of internalization of anti-ENDO180-CypHer5E conjugates by ENDO180 expressing cells. FIG. 2C shows internalization of CypHer5E labeled 8D8. FIG. 2D shows internalization of CypHer5E labeled scFv G7V (SEQ ID NO:6). FIG. 2E shows internalization of CypHer5E labeled 10F2.

Figure 2F:
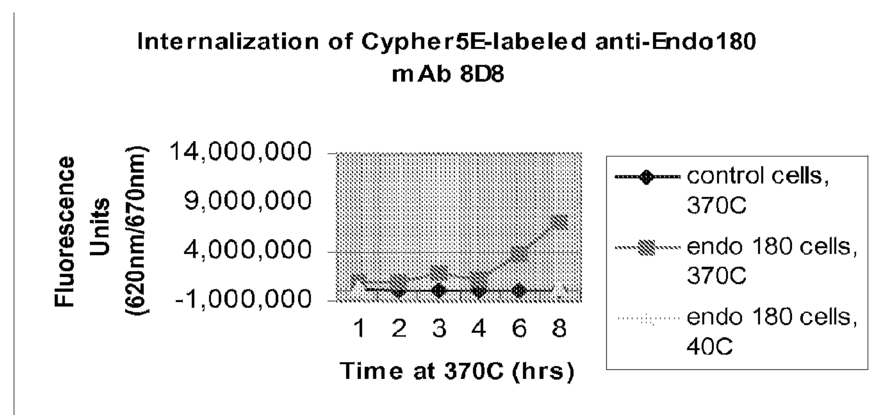
Figure 2G:
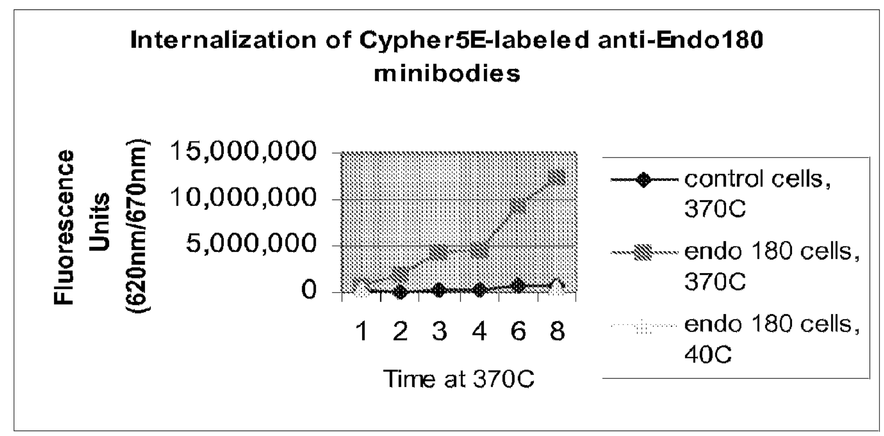
Figure 2H:
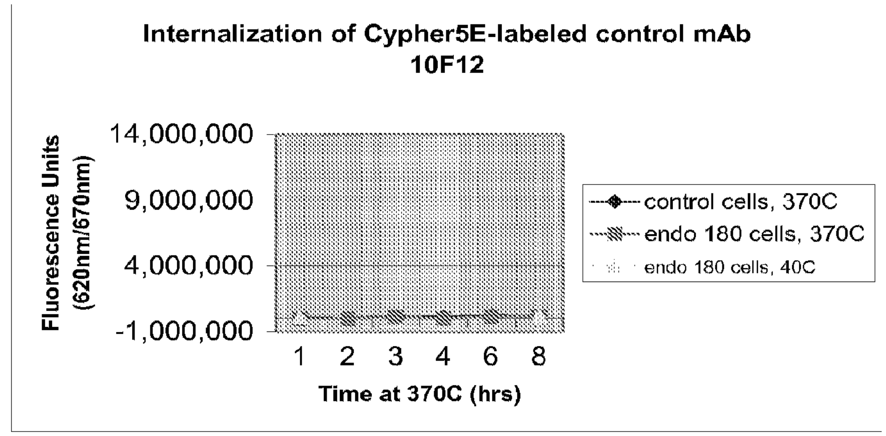

FIGS. 2F-2H shows a 1-hour to 8-hour time course of internalization of anti-ENDO180-CypHer5E conjugates by ENDO180 expressing cells. FIG. 2F shows internalization of CypHer5E labeled 8D8. FIG. 2G shows internalization of CypHer5E labeled scFv G7V (SEQ ID NO:6). FIG. 2E shows internalization of CypHer5E labeled 10F2.

The hybridoma cell line E3-8D8 that secretes monoclonal antibody E3-8D8, also referred to as 8D8, was deposited as per the Budapest Treaty in the Belgian Co-ordinated Collections of Mico-organisms (BCCM); Department of Biomedical Molecular Biology; Ghent University, Technologiepark 927, B-9052 GENT-Zwijnaarde, BELGIUM, with Accession Number LMBP 7203CB. The deposit was made on Mar. 9, 2010 and tested and shown to be viable on Mar. 18, 2010.

A composition for the systemic uptake of a drug across a mucosal membrane comprising a polyethylene glycol-chitosan conjugate, wherein the polyethylene glycol-chitosan conjugate comprises a chitosan or chitosan derivative moiety and a polyethylene glycol or a polyethylene glycol derivative moiety, and the composition is formulated for delivery to a mucosal membrane.

The general method of preparing a substrate-agent conjugate according to the invention involves covalently binding at least one therapeutic or diagnostic agent to a substrate. Certain cytotoxic drugs that are useful for anticancer therapy are relatively insoluble in serum. Some are also quite toxic in unconjugated form and their toxicity is considerably reduced by conversion to conjugates. Conversion of a relatively poorly soluble drug to a more soluble conjugate, e.g., a glucuronide, will improve its solubility in the aqueous phase of serum and its ability to pass through venous, arterial or capillary cell walls and reach the interstitial fluid bathing the tumor. In fact, conversion of certain toxic substances such as aromatic or alicyclic alcohols, thiols, phenols and amines to glucuronides in the liver is the body's method of detoxifying them and making them more easily excreted in the urine.

Example 4

In Vitro and In Vivo Internalization of Antibody Conjugates

FIG. 3 shows internalization of Biotin by anti-ENDO180 mAbs to mice Unilateral Ureter Obstructed kidney.

The following experiment was designed in order to assay ENDO180 antibody accumulation in ENDO180 expressing tissue. Unilateral ureter obstructed (UUO was performed in mice. The level of ENDO180 in kidneys at day 7 of UUO surgery, was higher than in the contra-lateral kidney (Data not shown).

Mice were injected with 3 mg/kg of E3-8D8-Biotin conjugate or NMIgG-Biotin conjugate at day 7 post UUO surgery, 24 hours later the kidney. The level of E3-8D8-Biotin conjugate and NMIgG-Biotin (normal mouse IgG control) conjugate uptake in the Unilateral ureter obstructed (UUO) kidney and Contra-lateral kidney was examined by Western blot (WB). The same amount of kidney total protein extract was examined by WB using Goat-anti-Biotin HRP (Cell signaling #7075).

FIG. 4 shows internalization of anti-ENDO180-CypHer5E conjugate in Myelo-Monocytoid human leukemia MonoMac cell line expressing ENDO180. MonoMac cells were incubated with E3 8D8-CypHer5E or E3 8D2-CypHer5E. Cells were washed twice with cold PBS and internalization was measured by FACS using FL-1 or FL-4 filter. E3 8D8 bound ENDO180 with higher affinity than E3-8D2 (Data not shown). 8D2 is a mAb that binds ENDO180 with lower affinity than 8D8.

Example 5

Linking Antibody to Therapeutic Agent a. MB: Full human protamine (~50 a.a) is cloned directly downstream to the constant region of the heavy chain. A similar strategy was taken using anti HIV-1gp 120 recombinant Fab fragment with a bicistronic vector expressing VH—CH1-protamine from one promoter and VKCK light chain from another (Chen et al., Gene Therapy (1995) 2, 116-123). This construct was shown to have in vivo anti-tumor activity (Song et al., Nature Biotech. 2005. 23(6), pg. 709-717). In another study, protamine was fused downstream to single chain antibody to ErbB (Li et al., Cancer Gene Therapy 8(8), 2001, pg. 555-565).
b. mAb: The CDR domains of the monoclonal antibody 8D8 are sequenced and cloned so that protamine can be engineered in fusion with it as with the MB.
c. Standard methods are used to link the antibody or antigen-binding fragment thereof (MB, isolated mAb, scFv, F' ab etc.) to the therapeutic agent using one or more of a peptide, nucleic acid, chemical or lipid linker

Example 6

In Situ Hybridization in Cancer Tissue Samples

Samples of human tissue from cancer patients were tested form expression of ENDO180 using in situ hybridization techniques. The tissue samples were analyzed by a skilled pathologist. The results showed the following expression patterns:

1. Renal Cell Carcinoma (RCC)
   - High level of ENDO180 mRNA expression appeared in cells in all five sarcomatoid areas studied, in two different renal cell carcinoma types—clear cell (four cases) and papillary (one case) carcinomas. Sarcomatoid carcinomas develop in all main types of renal cell carcinomas (clear cell, papillary, chromophobe and collecting duct carcinomas). They appear in approximately 1-1.5% of all adult renal tumors and are associated with an aggressive clinical course and poor prognosis.
   - ENDO180 mRNA expression appears also in intratumoral stromal cells, in non tumoral stromal cells and in glomerular cells, with some sample to sample variation of the amount of cells, and signal intensity.
2. Ovarian Cancer:
   - In most borderline serous papillary tumors that are represented in this study (7 out of 8), ENDO180 expression appeared in subsets of tumor cells, in various intensities.
   - ENDO180 mRNA expression in ovarian cancer cells appears in 8 out of 21 cases with some sample-to-sample variation of both amount and signal intensity of expressing cells.
   - High intensity signals of ENDO180 mRNA expression appeared in subsets of peritumor stromal cells and in subsets of ovarian stromal cells (94% and 100%). ENDO180 mRNA expression was also detected in single cells in normal epithelium.
3. Transitional Cell Carcinoma (TCC):
   - In most primary transitional cell (urothelial) carcinoma of bladder (18 out of 27 cases), and 4 cases of metastatic (in lymph nodes) tumors, that are represented in this study, ENDO180 expression was weak. High intensity signals of ENDO180 mRNA expression appeared in subsets of peritumor stromal cells.
4. Breast Cancer:
   - Expression of ENDO180 mRNA was seen in the peritumoral cells in most of the cases of invasive carcinoma (84%). No consistent expression pattern in epithelial cells.

Example 7

Animal Models for Testing Compounds in Treatment of Fibrosis

The following animal models are presented as non-limiting examples for use in testing exemplary molecules and conjugates of the present invention for efficacy in treating a subject suffering from fibrosis and fibrotic diseases. Other animal models are also considered.

A useful way to assess the development of renal diseases involving fibrosis and glomerulosclerosis is to characterize gene expression in established animal models of kidney diseases. Examples of such models include without limitation: (i) fa/fa rats—animals genetically deficient in leptin receptor that develop insulin resistant diabetes (type II diabetes) with progressive diabetic nephropathy, and (ii) GK rats—which are genetically manipulated, NIDDM phenotype rats. Another animal model in which mainly kidney fibrosis is evident, but without a background of diabetes, is unilateral ureteral obstruction (UUO) in which interstitial fibrosis is rapid and occurs within days following the obstruction. 5/6 nephrectomy is another useful animal model for chronic renal insufficiency (CRI) in which fibrosis is evident.

Additional aspects of research may be based on an in vitro model system involving culture of human fibroblasts in vitro under conditions mimicking various parameters of the cell microenvironment existing in CRI and fibrosis. These include treatment with high concentrations of glucose (modeling hyperglycemia), low concentrations of glucose, hypoxia (both modeling ischemic conditions that develop in the kidney following fibrosis and glomerulosclerosis), and TGF-b—one of the recognized pathogenic factors in fibrosis. Such in vitro model systems may complement the animal models in several important aspects: First, the system is fibroblast-specific; accordingly, none of the interferences often found in complex tissues that contain many cell types are present. Second, the cells are of human origin, unlike the animal models. Furthermore, the insults are specific and of various concentrations and duration, thus enabling the investigation of both acute and chronic responses.

Example 8

Animal Models for Testing the Compounds in Cancer Therapy

The following animal models are presented as non-limiting examples for use in testing exemplary molecules and conjugates of the present invention for efficacy in treating a subject suffering from cancer and other proliferative and metastatic diseases. Other animal models are also considered.

Transplantation in Immunodeficient Mice

The NOD/SCID mouse is defective in both lymphoid and myeloid function and readily accepts the long-term survival of human hematopoietic cells. Transplantation of human bone marrow into NOD/SCID mice to human/mouse chimeras, is well documented.

The NOD/SCID mice were used by Bertolini et al (2000. Blood 96-282) as a model high-grade non-Hodgkin lymphoma. The Namalwa cell line was used, which is derived from an Epstein-Barr virus-positive Burkitt non-Hodgkin lymphoma. The cells ($10\times10^6$) were injected intraperitoneally into 6-8 weeks old mice. Intraperitoneal tumors were formed in the injection site which could be measured by calipers. The formula: "width 2×length×0.52" was applied to approximate the volume of a spheroid. (see Bohem et al (1997) for further reference).

The model used in the following studies is based on transgenic SCID mice expressing human GM-CSF. The expression of this cytokine enabled the successful grafting of relevant cells lines in the SCID mice. Miyakawa et al (1996) details the production of the hGM-CSF SCID transgenic mice. Fukuchi et al (1998) shows that a retinoic-acid resistant leukemia can be established in these transgenic mice. The model consisted of UF-1 cells, an RA-resistant APL cell line established in that laboratory, which are transplanted into these transgenic SCID mice and cause the appearance of subcutaneous tumors. Kinjo et al (2000) uses this model to test a specific treatment, arsenic trioxide, to be used in cases of RA resistant acute promyelocytic leukemia (APL).

Lewis et al (1998) used the more profoundly immunodeficient mouse strain NOD/SCID in which both T-cell and B-cells are functionally defective, and there is marked impairment of macrophage, natural killer cell, and hemolytic complement activity. These mice can be engrafted with cells taken from cancer patients leading to a relatively high success rate and thus form a good model for the disease.

What is claimed is:

1. An anti-ENDO180 antibody or an antigen-binding fragment selected from the group consisting of:

a. an isolated monoclonal antibody produced by the hybridoma cell line E3-8D8, deposited with the BCCM under Accession Number LMBP 7203CB, or an antigen-binding fragment of such isolated monoclonal antibody;

b. a humanized version of the antibody of (a) or an antigen-binding fragment of such humanized version of the antibody of (a); and c. a chimeric version of the antibody of (a) or an antigen-binding fragment of such chimeric version of the antibody of (a);

wherein upon contact with a cell expressing ENDO180, the antibody or the antigen-binding fragment binds to the ENDO180 on the surface of the cell and is internalized into the cell.

2. A composition comprising the anti-ENDO180 antibody or the antigen-binding fragment of claim 1, and a pharmaceutically acceptable carrier.

3. The composition of claim 2, further comprising a moiety selected from the group consisting of a detectable label, a cytotoxic agent, and a therapeutic agent.

4. The composition of claim 3, wherein the carrier comprises a lipid particle, a polysaccharide particle, or a combination thereof.

5. The composition of claim 4, wherein the carrier comprises a lipidated polysaccharide particle.

6. The composition of claim 5, wherein the lipidated polysaccharide particle comprises a lipidated glycosaminoglycan particle.

7. The composition of claim 4, wherein the anti-ENDO180 antibody or the antigen-binding fragment is immobilized on the particle.

8. The composition of claim 3 or 4, wherein the moiety is a therapeutic agent.

9. The composition of claim 4, wherein the moiety is encapsulated within the lipid particle.

10. A hybridoma cell line designated E3-8D8, deposited with the BCCM under Accession Number LMBP 7203CB.

11. The composition of claim 3, wherein the anti-ENDO180 antibody or the antigen-binding fragment is conjugated to said moiety directly or via a linker which links the anti-ENDO180 antibody or the antigen-binding fragment to said moiety.

12. The composition of claim 11, wherein the anti-ENDO180 antibody or the antigen-binding fragment is conjugated to said moiety via a linker attached at the carboxyl terminus of the anti-ENDO180 antibody or the antigen-binding fragment.

13. The composition of claim 12, wherein the linker is selected from the group consisting of a polypeptide linker, a peptide linker, and a lipid linker.

14. A method of treating a subject afflicted with cancer or fibrosis comprising administering to the subject a composition of claim 8 in an amount effective to treat the subject.

15. The anti-ENDO180 antibody or the antigen-binding fragment of claim 1, wherein the anti-ENDO180 antibody or the antigen-binding fragment is selected from the group consisting of a full IgG, a Fab fragment, a Fab' fragment, a F(ab')2 fragment, a Fab, a miniantibody, and a scFv.

* * * * *